(12) United States Patent
Moffat et al.

(10) Patent No.: US 7,932,246 B2
(45) Date of Patent: Apr. 26, 2011

(54) HISTONE DEACETYLASE INHIBITORS

(75) Inventors: David Festus Charles Moffat, Abingdon (GB); Sanjay Ratilal Patel, Abingdon (GB); Francesca Ann Mazzei, Abingdon (GB); Andrew James Belfield, Abingdon (GB); Sandra Van Meurs, Abingdon (GB)

(73) Assignee: Chroma Therapeutics Ltd. (GB)

( * ) Notice: Subject to any disclaimer, the term of this patent is extended or adjusted under 35 U.S.C. 154(b) by 254 days.

(21) Appl. No.: 11/918,237

(22) PCT Filed: May 15, 2006

(86) PCT No.: PCT/GB2006/001779
§ 371 (c)(1),
(2), (4) Date: Dec. 4, 2008

(87) PCT Pub. No.: WO2006/123121
PCT Pub. Date: Nov. 23, 2006

(65) Prior Publication Data
US 2010/0152155 A1  Jun. 17, 2010

(30) Foreign Application Priority Data
May 19, 2005  (GB) .................. 0510204.1

(51) Int. Cl.
*A01N 43/00* (2006.01)
*A61K 31/33* (2006.01)
(52) U.S. Cl. ............... 514/210.2; 514/235.2; 514/275; 544/332; 544/331; 544/122; 435/184
(58) Field of Classification Search ............ 514/50, 514/210, 275, 235.2; 540/350; 554/35; 544/332, 544/331, 122; 435/184
See application file for complete search history.

(56) References Cited

FOREIGN PATENT DOCUMENTS

| WO | WO 03/076401 A1 | 9/2003 |
| WO | WO 03/076422 A1 | 9/2003 |
| WO | WO 03/076430 A1 | 9/2003 |

OTHER PUBLICATIONS

Vippagunta, et al. Advanced Drug Delivery Reviews, 48, 2001, p. 18.*

* cited by examiner

*Primary Examiner* — Brandon J Fetterolf
*Assistant Examiner* — Jean Cornet
(74) *Attorney, Agent, or Firm* — Banner & Witcoff, Ltd.

(57) ABSTRACT

Compounds of formula: (I), and salts, N-oxides, hydrates and solvates thereof are histone deacetylase inhibitors and are useful in the treatment of cell proliferative diseases, including cancers: (I) wherein Q, V and W independently represent —N= or —C=; B is a divalent radical selected from: (IIA), (IIB), (IIC), (IID), and (IIE). Wherein the bond marked * is linked to the ring containing Q, V and W through -[Linker1]- and the bond marked ** is linked to A through -[Linker2]-; A is an optionally substituted mono-, bi- or tri-cyclic carbocyclic or heterocyclic ring system; and -[Linker1]- and -[Linker2]- independently represent a bond, or a divalent linker radical.

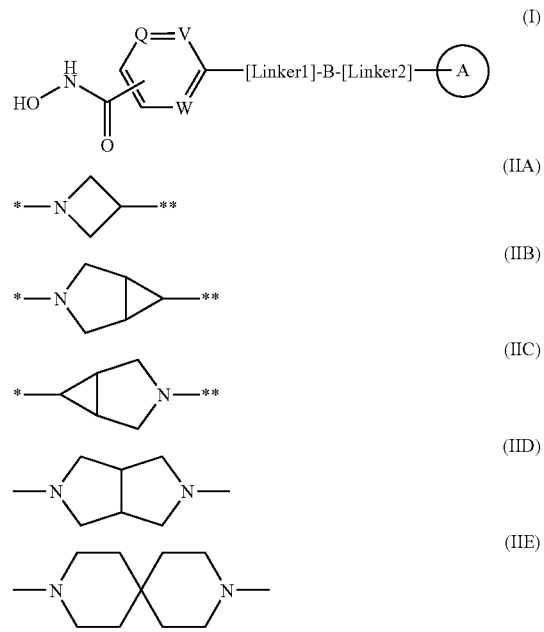

6 Claims, No Drawings

HISTONE DEACETYLASE INHIBITORS

CROSS REFERENCE TO RELATED APPLICATIONS

This application is a National Stage application of co-pending PCT application PCT/GB2006/001779 filed May 15, 2006, which claims the benefit of Great Britain application number 0510204.1 filed May 19, 2005. These applications are incorporated herein by reference in their entireties.

This invention relates to compounds which inhibit members of the histone deacetylase family of enzymes and to their use in the treatment of cell proliferative diseases, including cancers, polyglutamine diseases, for example Huntingdon disease, neurodegenerative diseases for example Alzheimer disease, autoimmune disease for example rheumatoid arthritis and organ transplant rejection, diabetes, haematological disorders, inflammatory disease, cardiovascular disease, atherosclerosis, and the inflammatory sequelae of infection.

BACKGROUND TO THE INVENTION

In eukaryotic cells DNA is packaged with histones, to form chromatin. Approximately 150 base pairs of DNA are wrapped twice around an octamer of histones (two each of histones 2A, 2B, 3 and 4) to form a nucleosome, the basic unit of chromatin. The ordered structure of chromatin needs to be modified in order to allow transcription of the associated genes. Transcriptional regulation is key to differentiation, proliferation and apoptosis, and is, therefore, tightly controlled. Control of the changes in chromatin structure (and hence of transcription) is mediated by covalent modifications to histones, most notably of the N-terminal tails. Covalent modifications (for example methylation, acetylation, phosphorylation and ubiquitination) of the side chains of amino acids are enzymatically mediated (A review of the covalent modifications of histones and their role in transcriptional regulation can be found in Berger S L 2001 Oncogene 20, 3007-3013; See Grunstein, M 1997 Nature 389, 349-352; Wolffe A P 1996 Science 272, 371-372; and Wade P A et al 1997 Trends Biochem Sci 22, 128-132 for reviews of histone acetylation and transcription).

Acetylation of histones is associated with areas of chromatin that are transcriptionally active, whereas nucleosomes with low acetylation levels are, typically, transcriptionally silent. The acetylation status of histones is controlled by two enzyme classes of opposing activities; histone acetyltransferases (HATs) and histone deacetylases (HDACs). In transformed cells it is believed that inappropriate expression of HDACs results in silencing of tumour suppressor genes (For a review of the potential roles of HDACs in tumorigenesis see Gray S G and Teh B T 2001 Curr Mol Med 1, 401-429). Inhibitors of HDAC enzymes have been described in the literature and shown to induce transcriptional reactivation of certain genes resulting in the inhibition of cancer cell proliferation, induction of apoptosis and inhibition of tumour growth in animals (For review see Kelly, W K et al 2002 Expert Opin Investig Drugs 11, 1695-1713). Such findings suggest that HDAC inhibitors have therapeutic potential in the treatment of proliferative diseases such as cancer (Kramer, O H et al 2001 Trends Endocrinol 12, 294-300, Vigushin D M and Coombes R C 2002 Anticancer Drugs 13, 1-13).

In addition, others have proposed that aberrant HDAC activity or histone acetylation is implicated in the following diseases and disorders; polyglutamine disease, for example Huntingdon disease (Hughes R E 2002 Curr Biol 12, R141-R143; McCampbell A et al 2001 Proc Soc Natl Acad Sci 98, 15179-15184; Hockly E et al 2003 Proc Soc Natl Acad Sci 100, 2041-2046), other neurodegenerative diseases, for example Alzheimer disease (Hempen B and Brion J P 1996, J Neuropathol Exp Neurol 55, 964-972), autoimmune disease and organ transplant rejection (Skov S et al 2003 Blood 101, 14 30-1438; Mishra N et al 2003 J Clin Invest 111, 539-552), diabetes (Mosley A L and Ozcan S 2003 J Biol Chem 278, 19660-19666) and diabetic complications, infection (including protozoal infection (Darkin-Rattray, S J et al 1996 Proc Soc Natl Acad Sci 93, 13143-13147)) and haematological disorders including thalassemia (Witt O et al 2003 Blood 101, 2001-2007). The observations contained in these manuscripts suggest that HDAC inhibition should have therapeutic benefit in these, and other related, diseases Many types of HDAC inhibitor compounds have been suggested, and several such compounds are currently being evaluated clinically, for the treatment of cancers. For example, the following patent publications disclose such compounds:

| | |
|---|---|
| U.S. Pat. No. 5,369,108 and WO 01/18171 | WO 03/076421 |
| U.S. Pat. No. 4,254,220 | WO 03/076430 |
| WO 01/70675 | WO 03/076422 |
| WO 01/38322 | WO 03/082288 |
| WO 02/30879 | WO 03/087057 |
| WO 02/26703 | WO 03/092686 |
| WO 02/069947 | WO 03/066579 |
| WO 02/26696 | WO 03/011851 |
| WO 03/082288 | WO 04/013130 |
| WO 02/22577 | WO 04/110989 |
| WO 03/075929 | WO 04/092115 |
| WO 03/076395 | WO 04/0224991 |
| WO 03/076400 | WO 05/014588 |
| WO 03/076401 | WO 05/018578 |
| WO 05/019174 | WO 05/013958 |
| WO 05/004861 | WO 05/028447 |
| WO 05/007091 | WO 05/02690 |
| WO 05/030704 | |

Many of the HDAC inhibitors known in the art have a structural template, which may be represented as in formula (A):

(A)

wherein ring A is a carbocyclic or heterocyclic ring system with optional substituents R, and [Linker] is a linker radical of various types. The hydroxamate group functions as a metal binding group, interacting with the metal ion at the active site of the HDAC enzyme, which lies at the base of a pocket in the folded enzyme structure. The ring or ring system A lies within or at the entrance to the pocket containing the metal ion, with the -[Linker]- radical extending deeper into that pocket linking A to the metal binding hydroxamic acid group. In the art, and occasionally herein, the ring or ring system A is sometimes informally referred to as the "head group" of the inhibitor.

BRIEF DESCRIPTION OF THE INVENTION

This invention makes available a new class of HDAC inhibitors having pharmaceutical utility in the treatment of diseases such as cancers which benefit from intracellular inhibition of HDAC.

DETAILED DESCRIPTION OF THE INVENTION

According to the invention there is provided a compound of formula (I), or a salt, N-oxide, hydrate or solvate thereof:

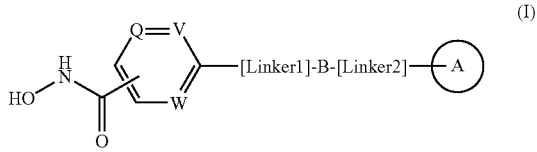

(I)

wherein
Q, V and W independently represent —N= or —C=;
B is a divalent radical selected from (IIA), (IIB), IIC), (IID), and (IIE).

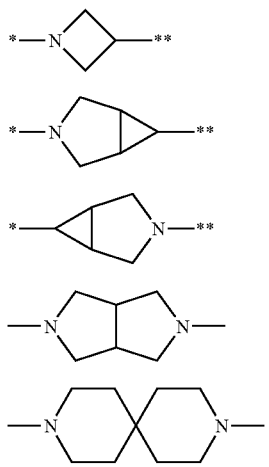

wherein the bond marked * is linked to the ring containing Q, V and W through -[Linker1]- and the bond marked ** is linked to A through -[Linker2]-;
A is an optionally substituted mono-, bi- or tri-cyclic carbocyclic or heterocyclic ring system; and
-[Linker1]- and -[Linker2]- independently represent a bond, or a divalent linker radical.

Although the above definition potentially includes molecules of high molecular weight, it is preferable, in line with general principles of medicinal chemistry practice, that the compounds with which this invention is concerned should have molecular weights of no more than 600.

In another broad aspect the invention provides the use of a compound of formula (I) as defined above, or an N-oxide, salt, hydrate or solvate thereof in the preparation of a composition for inhibiting the activity of histone deacetylase.

The compounds with which the invention is concerned may be used for the inhibition of histone deacetylase activity, ex vivo or in vivo.

In one aspect of the invention, the compounds of the invention may be used in the preparation of a composition for the treatment of cell-proliferation disease, for example cancer cell proliferation and autoimmune diseases.

In another aspect, the invention provides a method for the treatment of the foregoing disease types, which comprises administering to a subject suffering such disease an effective amount of a compound of formula (I) as defined above.

TERMINOLOGY

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the term "divalent $(C_a-C_b)$alkylene radical" wherein a and b are integers refers to a saturated hydrocarbon chain having from a to b carbon atoms and two unsatisfied valences.

As used herein the term "$(C_a-C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a-C_b)$alkenylene radical" means a hydrocarbon chain having from a to b carbon atoms, at least one double bond, and two unsatisfied valences.

As used herein the term "$C_a-C_b$ alkynyl" wherein a and b are integers refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_a-C_b)$alkynylene radical" wherein a and b are integers refers to a divalent hydrocarbon chain having from a to b carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, $(C_1-C_6)$ alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, phenyl, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl, $(C_3-C_6)$ cycloalkyl, phenyl or monocyclic heteroaryl having 5 or 6 ring atoms. An "optional substituent" may be one of the foregoing substituent groups.

As used herein, the term "nitrogen substituent" means a substituent on a nitrogen atom which is selected from the following:
amino $C_{1-6}$ alkyl eg aminoethyl, $C_{1-3}$ alkylamino $C_{1-6}$ alkyl, $C_{1-3}$ dialkylamino $C_{1-6}$ alkyl, hydroxy $C_{1-6}$ alkyl eg hydroxyethyl, $C_{1-3}$ alkoxy $C_{1-6}$ alkyl eg methoxyethyl, mercapto $C_{1-3}$ alkyl, $C_{1-3}$ alkylmercapto $C_{1-6}$ alkyl, carboxamido $C_{1-6}$ alkyl e.g. —CH$_2$CONH$_2$, aminosulphonyl $C_{1-6}$ alkyl e.g. —CH$_2$SO$_2$NH$_2$, $C_{1-3}$ alkylaminosulphonyl $C_{1-6}$ alkyl e.g. —CH$_2$SO$_2$NHMe, $C_{1-3}$ dialkylaminosulphonyl $C_{1-6}$ alkyl e.g. —CH$_2$SO$_2$NMe$_2$, $C_{1-6}$ alkanoyl, $C_{1-6}$ alkylsulphonyl, aminosulphonyl (—SO$_2$NH$_2$), $C_{1-6}$ alkylaminosulphonyl e.g. —SO$_2$NHMe, $C_{1-6}$ dialkylaminosulphonyl e.g. —SO$_2$NMe$_2$, optionally substituted phenylaminosulphonyl, carboxamido (—CONH$_2$), $C_{1-6}$ alkylaminocarbonyl, $C_{1-6}$ dialkylaminocarbonyl, morpholinyl $C_{1-6}$ alkyl, imidazolyl $C_{1-6}$ alkyl, triazolyl $C_{1-6}$ alkyl, or monocyclic heterocycloalkyl $C_{1-6}$ alkyl, optionally substituted in the imidazolyl, triazolyl or heterocyclyl ring, eg piperidinyl $C_{1-6}$ alkyl, piperazinyl $C_{1-6}$ alkyl or 4-($C_{1-6}$ alkyl)piperazinyl $C_{1-6}$ alkyl.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like.

Compounds of the invention which contain one or more actual or potential chiral centres, because of the presence of asymmetric carbon atoms, can exist as a number of enantiomers or diastereoisomers with R or S stereochemistry at each chiral centre. The invention includes all such enantiomers or diastereoisomers and mixtures thereof.

In the compounds of the invention, in any compatible combination, and bearing in mind that the compounds preferably have a molecular weight of less than 600:

The Ring Containing Q, V and W

Each of Q, V and W may be —C=, or at least one of Q, V and W may be —N=, or Q may be —C= and V and W may each be —N=; Currently preferred is the case where Q is —C=, V and W are each be. —N= and the HONHC(=O)— radical is attached to the 5-position of the resultant pyrimidin-2-yl radical.

The Ring A

Ring A radicals may be, for example, optionally substituted aromatic carbocyclic such as optionally substituted phenyl and naphthyl, or optionally substituted heteroaromatic such as optionally substituted pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,3,4-triazolyl, 1,2,5-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, indanyl, 3H-indolyl, benzimidazolyl, indazolyl, imidazo[1,2-a]pyridyl, benzothiazolyl, benzoxazolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl radicals.

Ring A radicals may also be, for example, optionally substituted non aromatic carbocyclic and heterocyclic, such as optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, 2,4-cyclopentadien-1-yl, 3,5-cyclohexadien-1-yl, tetrahydrofuranyl, pyrroline, eg 2- or 3-pyrrolinyl, pyrrolidinyl, dioxolanyl, eg 1,3-dioxolanyl, imidazolinyl, eg 2-imidazolinyl, imidazolidinyl, pyrazolinyl, eg 2-pyrazolinyl, pyrazolidinyl, pyranyl, eg 2- or 4-pyranyl, piperidinyl, 1,4-dioxanyl, morpholinyl, 1,4-dithianyl, thiomorpholinyl, piperazinyl, 1,3,5-trithianyl, oxazinyl, eg 2H-1,3-, 6H-1,3-, H-1,2-, 2H-1,2- or 4H1,4-oxazinyl, 1,2,5-oxathiazinyl, isoxazinyl, oxathiazinyl, eg 1,2,5 or 1,2,6-oxathiazinyl, or 1,3,5-oxadiazinyl radicals.

Specific ring A radicals include the following ring systems, optionally substituted:

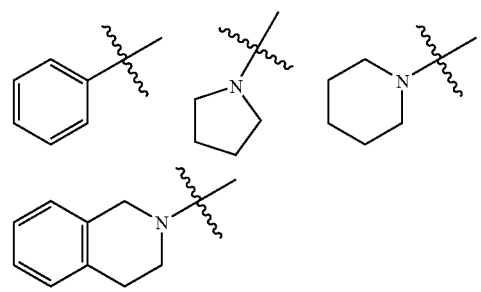

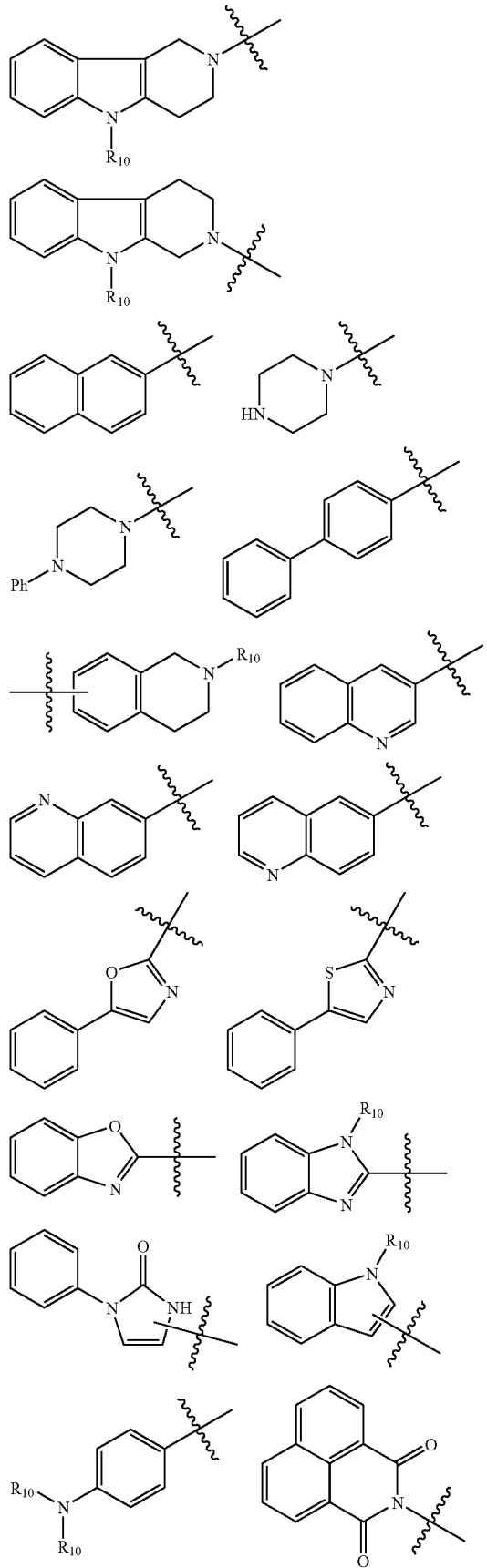
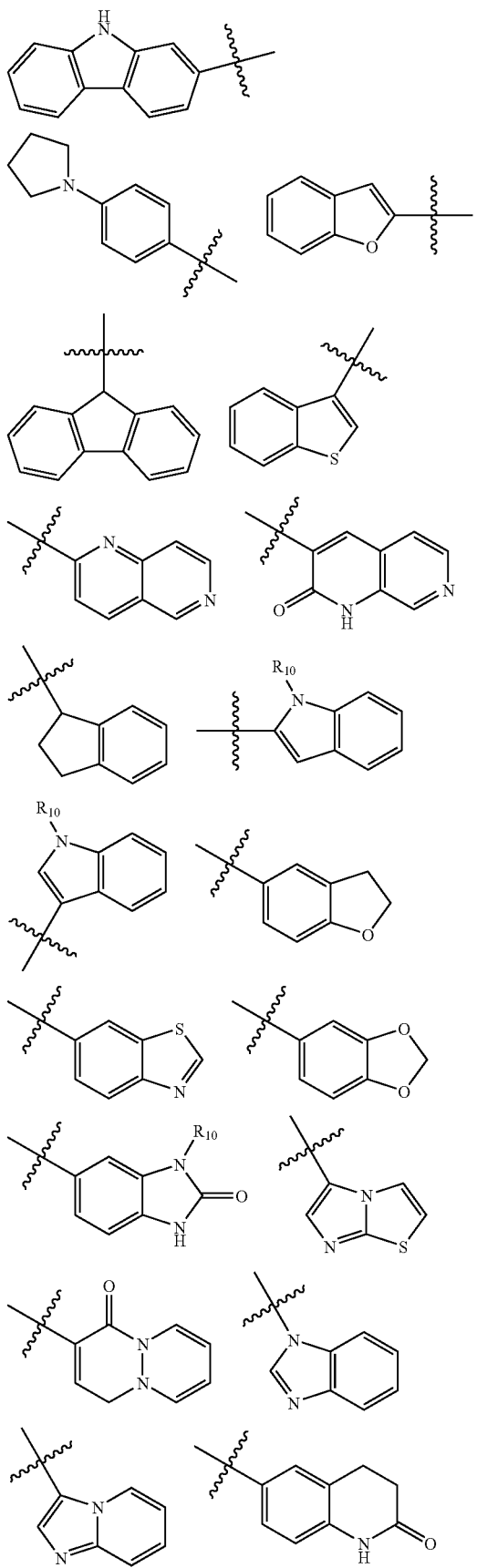

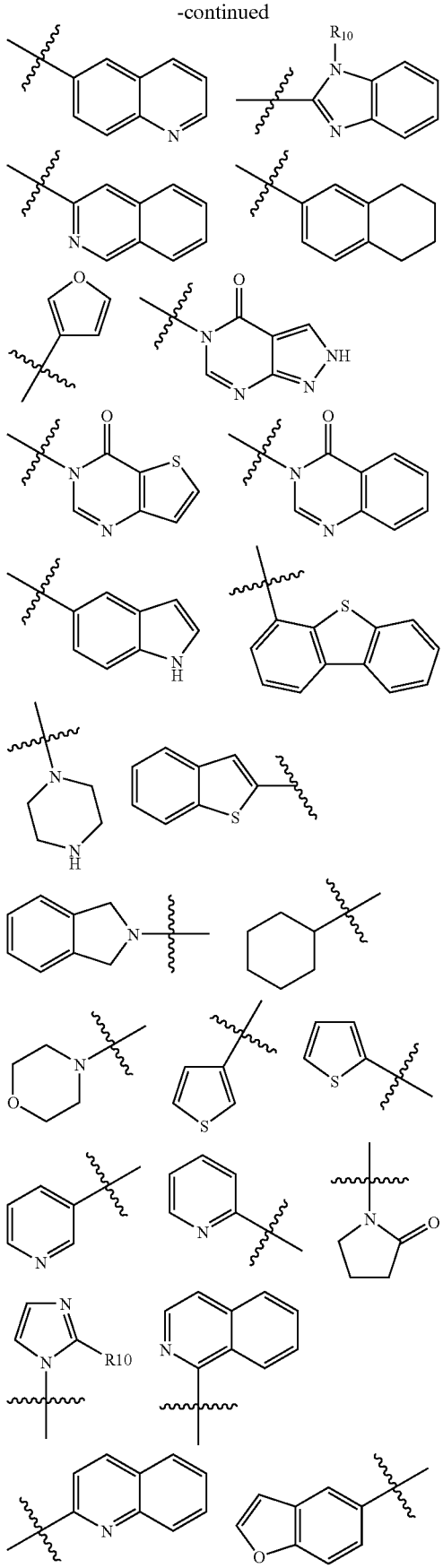
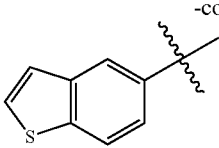

wherein $R_{10}$ is hydrogen or $C_1$-$C_6$ alkyl, the bond intersected by the wavy line connects to the -[Linker2]- radical.

Optional substituents in A may be, for example methyl, ethyl, n-propyl, isopropyl, fluorine, chlorine, bromine or iodine atoms, or a methylamino, ethylamino, hydroxymethyl, hydroxyethyl, methylthiol, ethylthiol, methoxy, ethoxy, n-propoxy, 2-hydroxyethoxy, 3-hydroxypropoxy, 2-aminoethoxy, 3-aminopropoxy, 2-(methylamino)ethoxy, 2-(dimethylamino)ethoxy, 3-(dimethylamino)propoxy, cyclopentyl, cyclohexyl, cyclohexylamino, trifluoromethyl, trifluoromethoxy, amino (—$NH_2$), aminomethyl, aminoethyl, dimethylamino, diethylamino, ethyl(methyl)amino, propyl(methyl)amino, 2-hydroxyethylamino, 3-hydroxypropylamino, 2-aminoethylamino, 3-aminopropylamino, 2-(methylamino)ethylamino, 2-(ethylamino)ethylamino, 2-(isopropylamino)ethylamino, 3-(isopropylamino)propylamino, 2-(dimethylamino)ethylamino, 2-(diethylamino)ethylamino, 2-(methylamino)ethyl(methyl)amino, 3-(methylamino)propyl(methyl)amino, nitro, cyano, hydroxyl, formyl, carboxyl (—$CO_2H$), —$CH_2CO_2H$, —$OCH2CO2H$, —$CO_2CH_3$, —$CO_2CH_2CH_3$, —$CH_2CO_2CH_2CH_3$, —$CH_2CO_2CH_2Ph$, t-butoxycarbonylmethoxy, acetyl, phenacyl, thio, thiomethyl, thioethyl, sulphonyl, methylsulphonyl, methylaminosulphonyl, ethylaminosulphonyl, dimethylaminosulphonyl, carboxamido, methylaminocarbonyl, ethylaminocarbonyl, dimethylaminocarbonyl, diethylaminocarbonyl, methylaminocarbonylmethyl, —$NHC(S)NH_2$, sulphonylamino (—$NHSO_2H$), methylsulphonylamino, dimethylsulphonylamino, aminosulphonylamino, (—$NHSO_2NH_2$), methylaminosulphonylamino, dimethylaminosulphonylamino, methylaminocarbonylamino, dimethylaminocarbonylamino, acetylamino, phenylcarbonylamino, aminomethylcarbonylamino, acetylaminomethyl, methoxycarbonylamino, t-butoxycarbonylamino, pyrrolidinyl, piperidynyl, piperazinyl, 4-methylpiperazinyl, homopiperazinyl, morpholinyl, imidazolyl, 1,2,4-triazolyl, 1,2,3-triazolyl, 1,3,4-triazolyl, 1,2,5-triazolyl, $C_{1-6}$ straight or branched chain alkyl, amino $C_{1-6}$ alkyl eg aminoethyl, $C_{1-3}$ alkylamino $C_{1-6}$ alkyl, $C_{1-3}$ dialkylamino $C_{1-6}$ alkyl, hydroxyl $C_{1-6}$ alkyl eg hydroxyethyl, $C_{1-3}$ alkoxyl $C_{1-6}$ alkyl eg methoxyethyl, thiol $C_{1-3}$ alkyl $C_{1-6}$, $C_{1-3}$ alkylthiol $C_{1-6}$ alkyl, $C_{1-6}$ alkanoyl, $C_{1-6}$ alkylsulphonyl, aminosulphonyl (—$SO_2NH_2$), $C_{1-6}$ alkylaminosulphonyl e.g. —$SO_2NHMe$, $C_{1-6}$ dialkylaminosulphonyl e.g. —$SO_2NMe_2$, optionally substituted phenylaminosulphonyl, carboxamido (—$CONH_2$), carboxamido $C_{1-6}$ alkyl e.g. $CH_2CONH_2$, $C_{1-6}$ alkylaminocarbonyl, $C_{1-6}$ dialkylaminocarbonyl, aminosulphonyl $C_{1-6}$ alkyl e.g. $CH_2SO_2NH_2$, $C_{1-3}$ alkylaminosulphonyl $C_{1-6}$ alkyl e.g. $CH_2SO_2NHMe$, $C_{1-3}$ dialkylaminosulphonyl $C_{1-6}$ alkyl e.g. $CH_2SO_2NMe_2$, $C_{1-6}$ morpholinyl $C_{1-6}$ alkyl, optionally substituted imidazolyl $C_{1-6}$ alkyl, optionally substituted triazolyl $C_{1-6}$ alkyl, optionally substituted hetero $C_{3-6}$ cycloalkyl $C_{1-6}$ alkyl eg piperidinyl $C_{1-6}$ alkyl, piperazinyl $C_{1-6}$ alkyl, and 4-($C_{1-6}$ alkyl)piperazinyl $C_{1-6}$ alkyl.

Currently preferred rings A include optionally substituted phenyl, naphthyl, quinolin-2-yl, and 1,3-dihydro-isoindol-2-yl. Substituents which may be present in such preferred rings A include halogen, particularly fluoro and chloro.

The Linkers 1 and 2

-[Linker1]- and -[Linker2]- serve to link the divalent B radical to the ring A and the ring containing Q, V and W. Thus, they may be selected, independently, from the following examples:

(i) a bond;

(ii) —O—, —S—, —C(=O)—, —S(=O)$_2$—, —NR$^1$—, —C(=O)NR$^1$—, —S(=O)$_2$NR$^1$—, —NR$^1$C(=O)—, —NR$^1$S(=O)$_2$—, —NR$^1$(CH$_2$)$_m$—, —NR$^1$C(=O)(CH$_2$)$_m$—, —NR$^1$S(=O)$_2$(CH$_2$)$_m$—, —NR$^2$C(=O)NR$^1$—, —NR$^1$C(=O)(CH$_2$)$_m$Ar—, or —NR$^1$S(=O)$_2$(CH$_2$)$_m$Ar— wherein R$^1$ and R$^2$ are independently hydrogen, $C_1$-$C_4$ alkyl, or a nitrogen substituent, m is 0, 1, 2, 3, 4 or 5 and Ar is a divalent phenyl radical or a divalent mono-, or bi-cyclic heteroaryl radical having 5 to 13 ring members; and (iii) an optionally substituted, straight or branched, $C_1$-$C_6$ alkylene, $C_2$-$C_6$ alkenylene or $C_2$-$C_6$ alkynylene radical which may optionally contain or terminate in an ether (—O—), thioether (—S—) or amino (—NR$^A$—) link wherein R$^A$ is hydrogen, $C_1$-$C_3$ alkyl, or a nitrogen substituent;

When —Ar— is present in one of -[Linker1]- and -[Linker2]- it may be a divalent radical selected from the following:

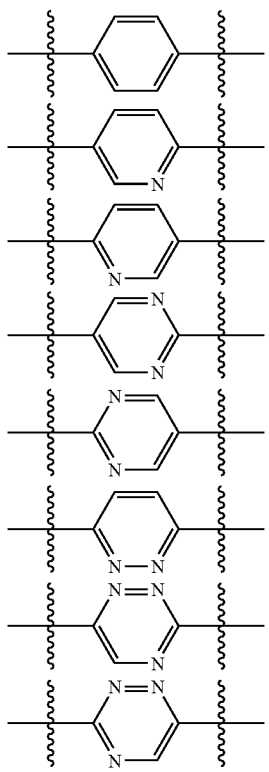

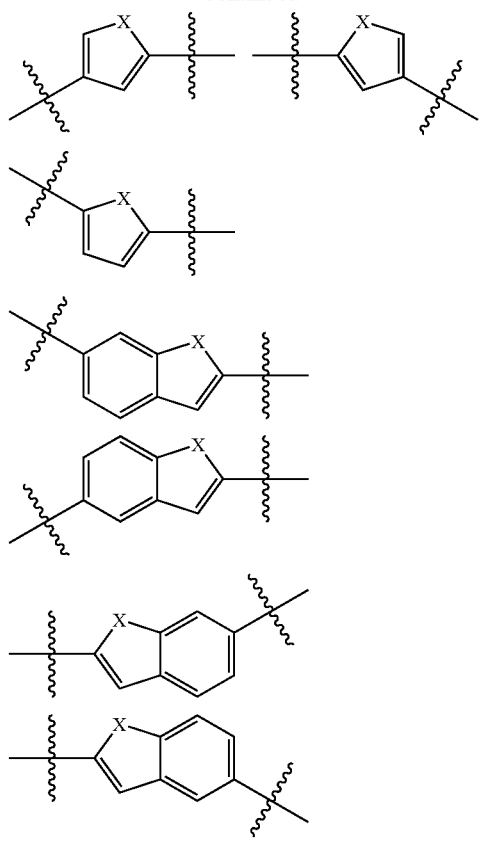

wherein X is O, S or NH. For example, —Ar— when present in one of -[Linker1]- and -Linker2]- may be a divalent phenylene, such as a 1,4-phenylene, radical.

Examples of linker radicals -[Linker1]- and -[Linker2]- include those present in the compounds of the specific examples herein In some currently preferred embodiments of the compounds of the invention, -[Linker1]- is a bond when B is a divalent radical (IIA), (IIB), (IID) or (IIE), or —NH— when B is a divalent radical (IIC).

In some currently preferred embodiments of the compounds of the invention, -[Linker2]- is —NHS(=O)$_2$—, —NHC(=O)—, —NHC(=O)(CF$_{12}$)$_m$—, —NHS(=O)$_2$(CH$_2$)$_m$—, or —NH(CH$_2$)$_m$—, wherein m is 1, 2, 3, 4 or 5, and wherein the hydrogen on the nitrogen atom may be replaced by a nitrogen substituent A currently preferred subclass of compounds of the invention consists of those of formula (IA):

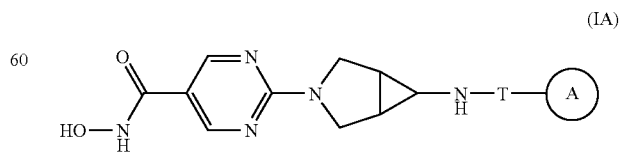

(IA)

wherein T is —S(=O)$_2$—, —C(=O)— or —CH$_2$—, and A is as defined and discussed above.

Specific examples of compound of the invention include the following, and their N-oxides, salts hydrates and solvates:

N-Hydroxy 2-(5-naphthalen-2-ylmethylhexahydropyrrolo[3,4-c]pyrrol-2[1H]-yl)pyrimidine-5-carboxamide N-Hydroxy 2-{6-[(2-naphthylsulfonyl)amino]-3-azabicyclo[3.1.0]hex-3-yl}pyrimidine-5-carboxamide trifluoroacetate N-Hydroxy 2-{6-[(6-fluoroquinolin-2-ylmethyl)amino]-3-aza-bicyclo[3.1.0]hex-3-yl}pyrimidine-5-carboxamide N-Hydroxy 2-{6-[(2-naphthylmethyl)amino]-3-azabicyclo[3.1.0]hex-3-yl}pyrimidine-5-carboxamide N-Hydroxy 2-[6-(1,3-dihydro-2H-isoindol-2-yl)-3-azabicyclo[3.1.0]hex-3-yl]pyrimidine-5-carboxamide hydrochloride N-Hydroxy 2-{6-[(4-chlorobenzyl)amino]-3-azabicyclo[3.1.0]hex-3-yl}pyrimidine-5-carboxamide hydrochloride N-Hydroxy 2-{6-[(naphthalene-2-sulfonyl)-(2-piperidin-1-ylethyl)-amino]-3-aza-bicyclo[3.1.0]hex-3-yl}pyrimidine-5-carboxamide N-Hydroxy 2-{6-[(quinolin-2-ylmethyl)amino]-3-azabicyclo[3.1.0]hex-3-yl}pyrimidine-5-carboxamide trifluoroacetate N-Hydroxy 2-[5-(4-chlorobenzyl)hexahydropyrrolo[3,4-c]pyrrol-2(1H)-yl]pyrimidine-5-carboxamide tetratrifluoroacetate N-Hydroxy 2-[5-(naphthalene-2-carbonyl)-hexahydropyrrolo[3,4-c]pyrrol-2-yl]pyrimidine-5-carboxamide As mentioned above, the compounds with which the invention is concerned are HDAC inhibitors, and may therefore be of use in the treatment of cell proliferative disease, such as cancer, in humans and other mammals.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "*Advanced organic chemistry*", 4$^{th}$ Edition (Wiley), J March, "*Comprehensive Organic Transformation*", 2$^{nd}$ Edition (Wiley), R. C. Larock, "*Handbook of Heterocyclic Chemistry*", 2$^{nd}$ Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*". The synthetic routes used in the preparation of the compounds of the Examples below may be adapted for the preparation of analogous compounds.

The following Examples illustrate the preparation of specific compounds of the invention, and the HDAC inhibitory properties thereof:

Scheme 1: Preparation of ethyl 2-(methylsulfonyl)pyrimidine-5-carboxylate-Intermediate A

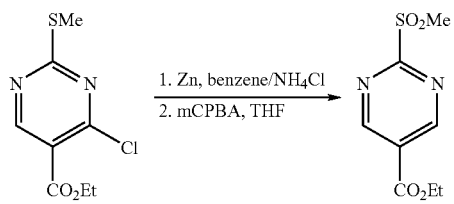

Scheme 2: Preparation of tert-butyl 6-amino-3-azabicyclo[3.1.0]hexane-3-carboxylate-Intermediate B

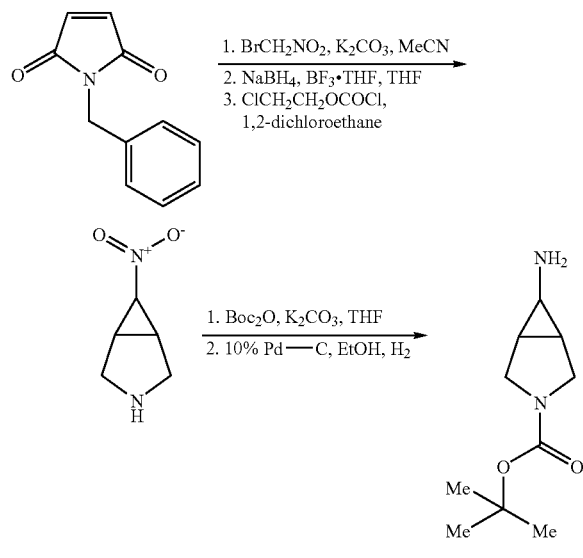

Scheme 3: Preparation of tert-butyl 3-azabicyclo[3.1.0]hex-6-ylmethylcarbamate-Intermediate C

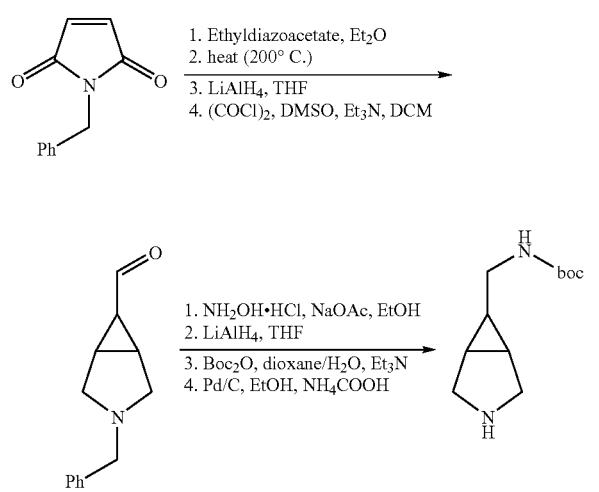

Scheme 4: Preparation of O-(1-isobutoxyethyl)hydroxylamine-Intermediate D

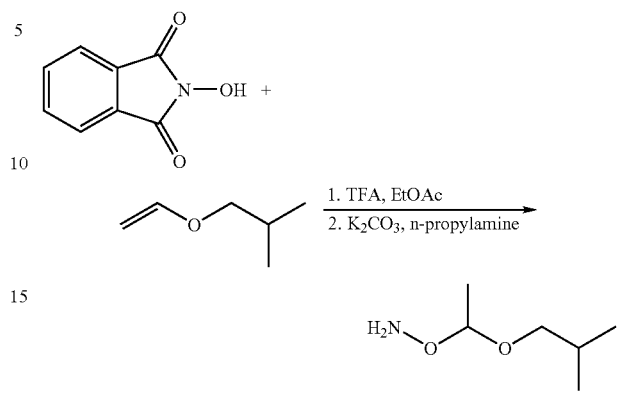

Scheme 5: Preparation of N-hydroxy 2-{6-[(2-naphthylsulfonyl)amino]-3-azabicyclo[3.1.0]hex-3-yl}pyrimidine-5-carboxamide

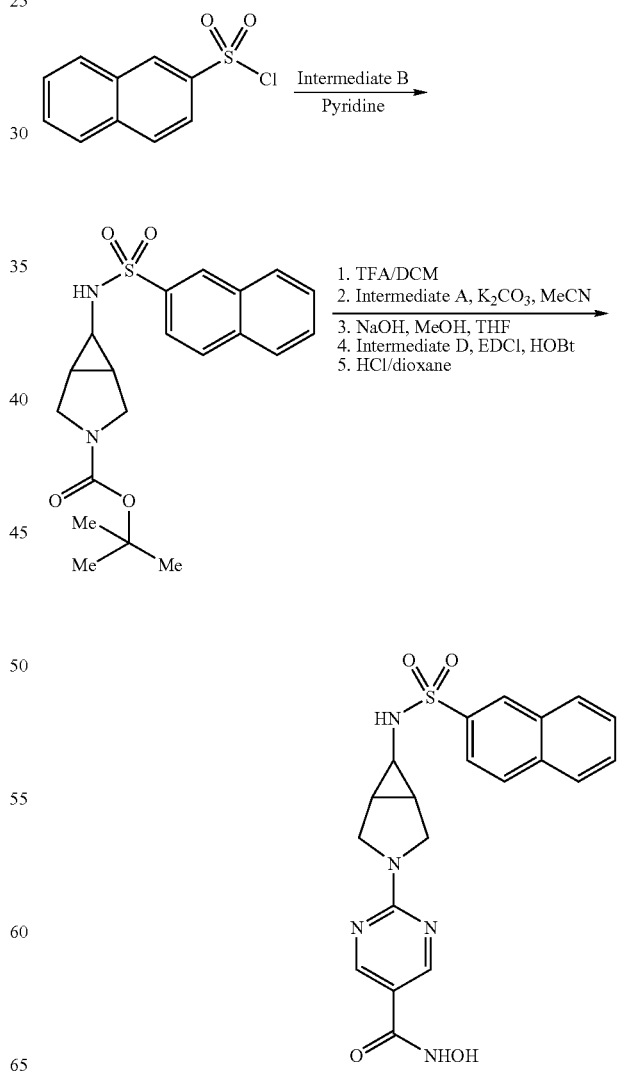

Scheme 6: Preparation of N-hydroxy-2{6-[(2-naphthylcarbonyl)amino]-3-azabicyclo[3.1.0]hex-3-yl}pyrimidine-5-carboxamide
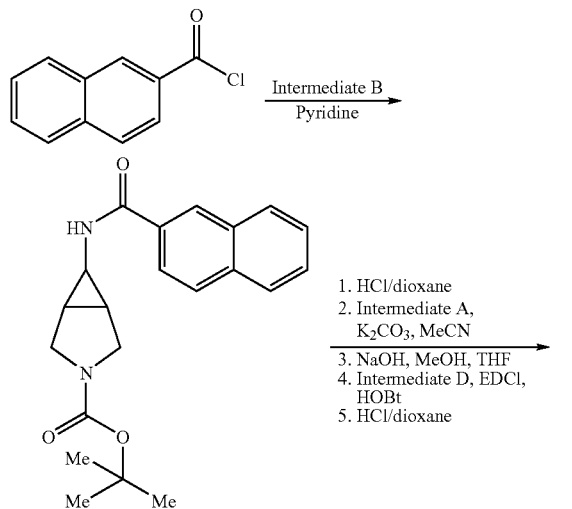
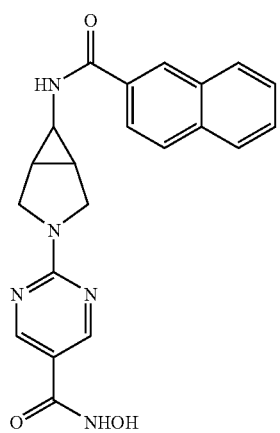
Scheme 7: Preparation of N-hydroxy 2{6-[(naphthalene-2-ylmethyl)amino]-3-aza-bicyclo[3.1.0]hex-3-yl}-pyrimidine-5-carboxamide
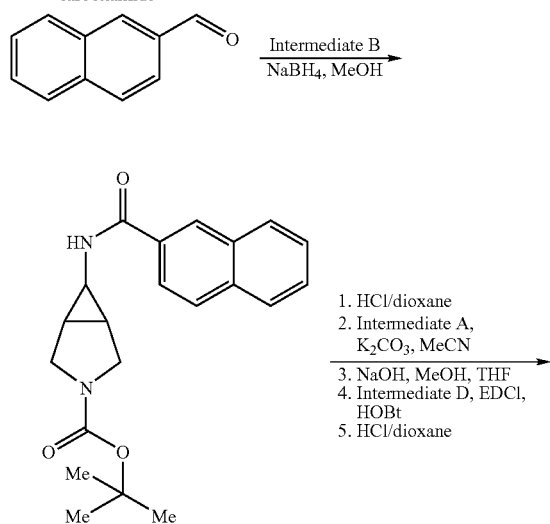
Scheme 8: Preparation of N-hydroxy 2-{6-[alkyl(napthalene-2-ylsulfonyl)amino]-3-azabicyclo[3.1.0]hex-3-yl}pyrimidine-5-carboxamide -continued

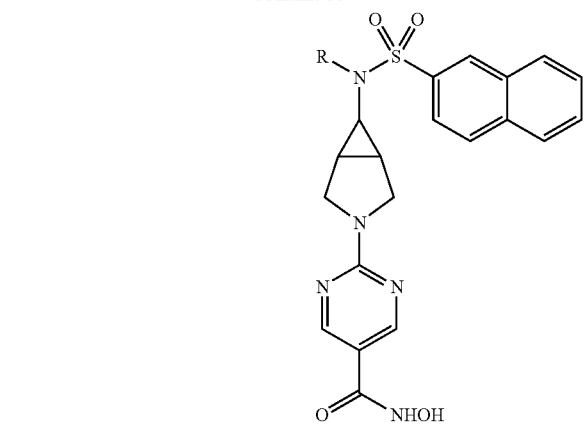

Method A: NaH, dimethylsulfate, DMF
Method B: R—X, NaH, DMF
Method C: DIAD, PPh₃, R—OH, DCM Scheme 9: Preparation of N-hydroxy 2-{6-[(2-diethylaminoethyl)naphthalene-2-ylmethyl amino]-3-azabicyclo[3.1.0]hex-3-yl}pyrimidine-5-carboxamide

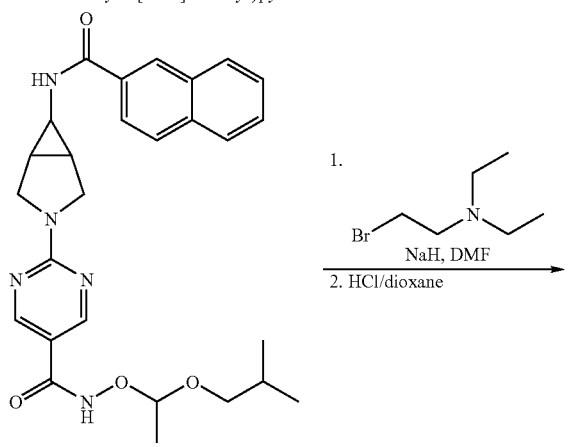

Scheme 10: Preparation of N-hydroxy 2-{6-[(3-diethylaminopropionyl)naphthalen-2-yl methylamino]-3-azabicyclo[3.1.0]hex-3-yl}pyrimidine-5-carboxamide

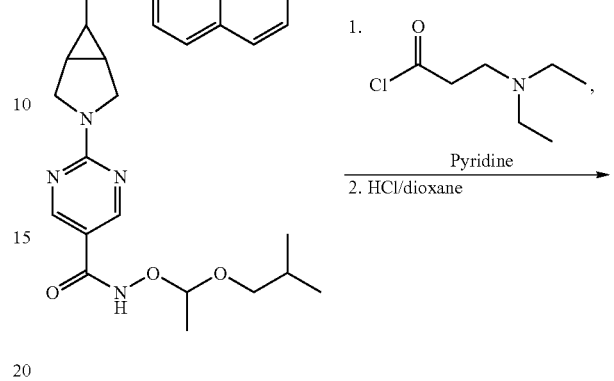

Scheme 11: Preparation of N-hydroxy 2-(morpholin-4-yl-3-azabicyclo[3.1.0]hex-3-yl)pyrimidine-5-carboxamide

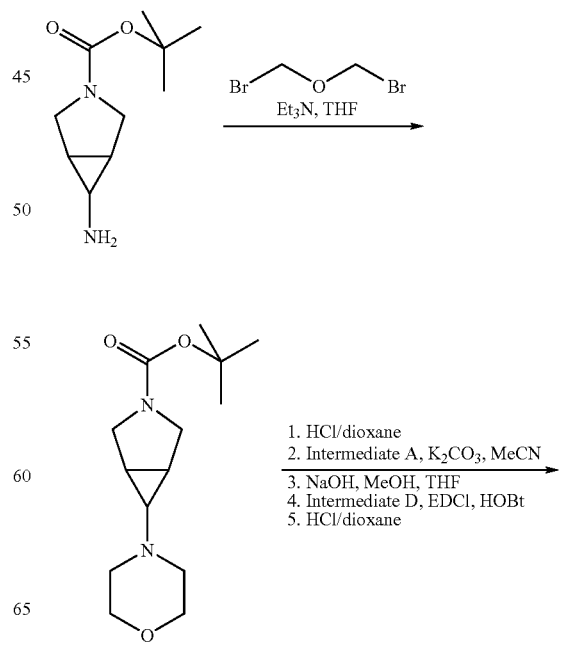

1. HCl/dioxane
2. Intermediate A, K₂CO₃, MeCN
3. NaOH, MeOH, THF
4. Intermediate D, EDCl, HOBt
5. HCl/dioxane

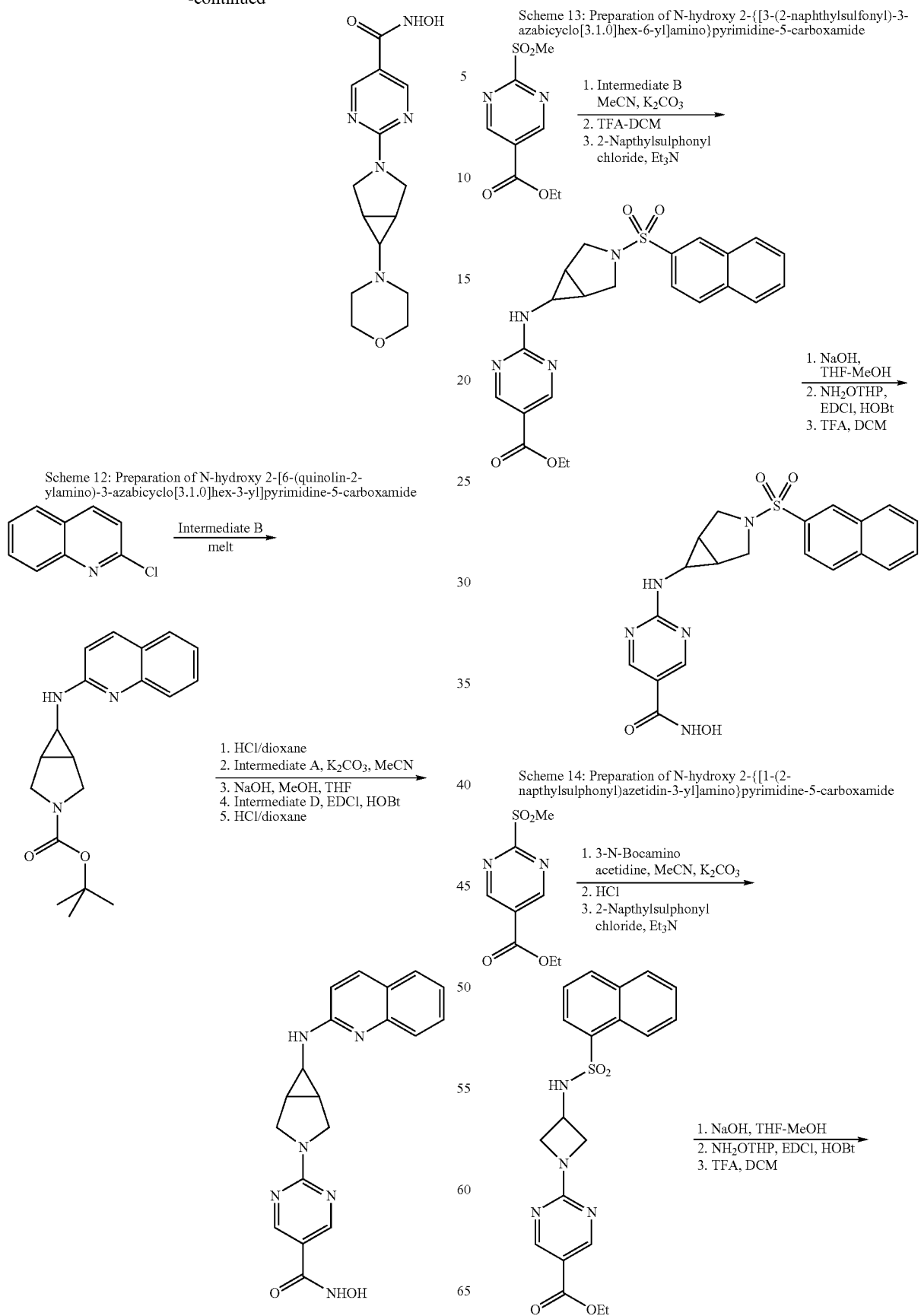

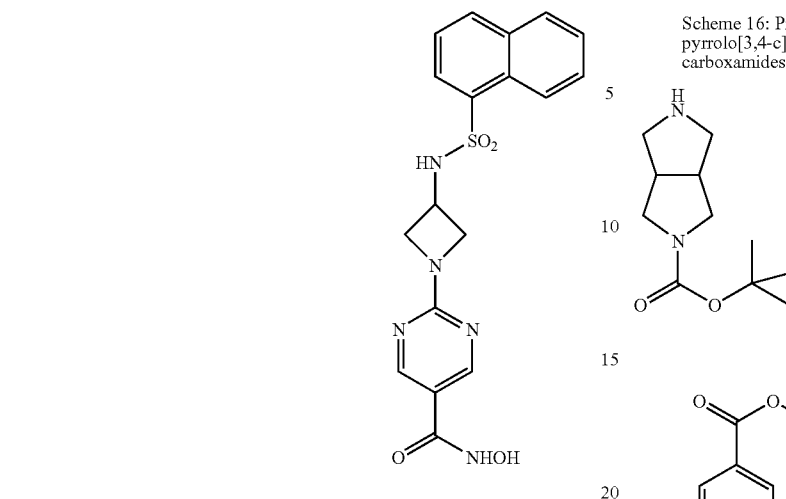
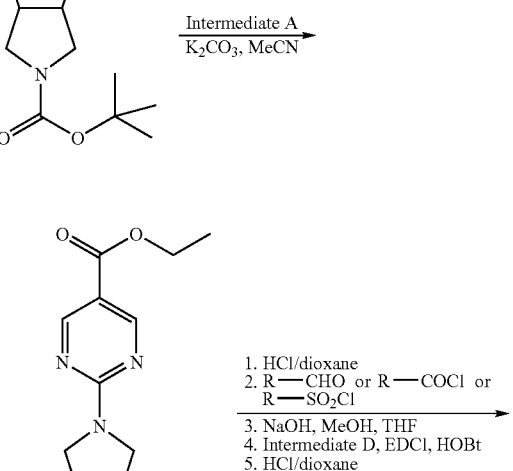
Scheme 16: Preparation of N-substituted 2-(hexahydro-pyrrolo[3,4-c]pyrrol-2(1H)-yl)-N-hydyroxypyrimidine-5-carboxamides
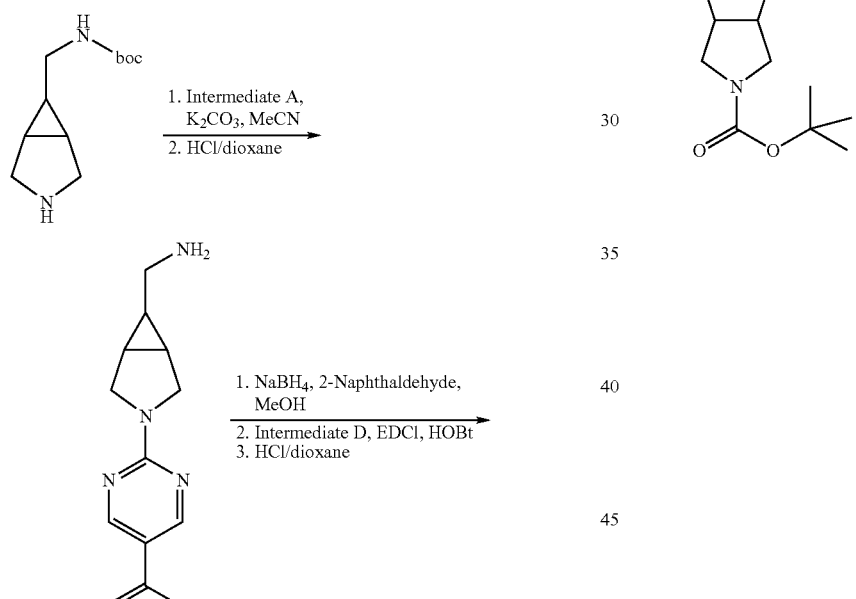
Scheme 15: Preparation of N-hydroxy 2-{6-[(naphthalen-2-ylmethylamino)methyl]-3-azabicyclo[3.1.0]hex-3-yl}pyrimidine-5-carboxamide
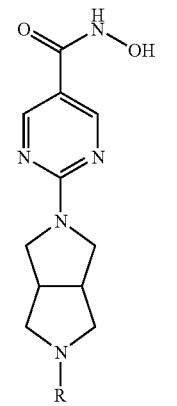
R = alkyl, aryl or sulfonyl
Scheme 17: Preparation of N-substituted 2-(3,9-diazaspiro[5.5]undec-3-yl)-N-hydroxypyrimidine-5-carboxamides
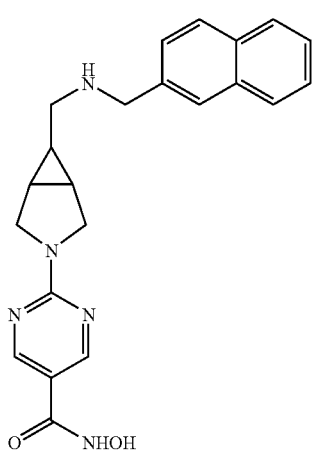
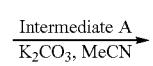

-continued

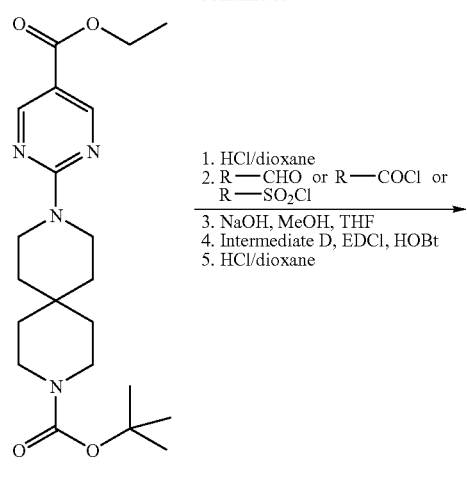

1. HCl/dioxane
2. R—CHO or R—COCl or R—SO$_2$Cl
3. NaOH, MeOH, THF
4. Intermediate D, EDCl, HOBt
5. HCl/dioxane

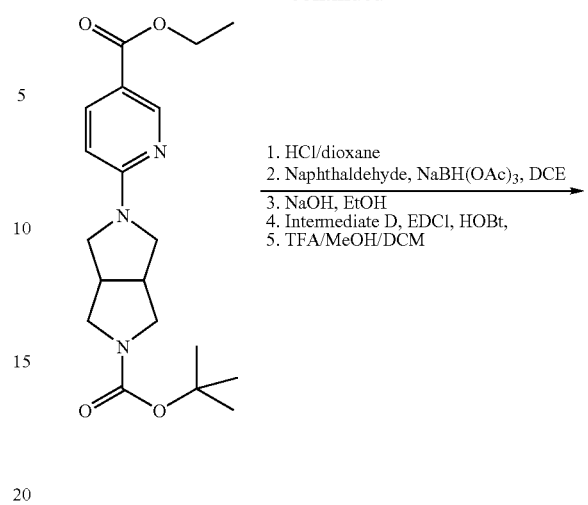

1. HCl/dioxane
2. Naphthaldehyde, NaBH(OAc)$_3$, DCE
3. NaOH, EtOH
4. Intermediate D, EDCl, HOBt,
5. TFA/MeOH/DCM

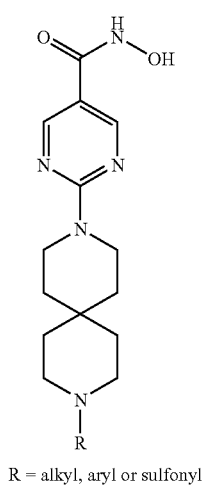

R = alkyl, aryl or sulfonyl

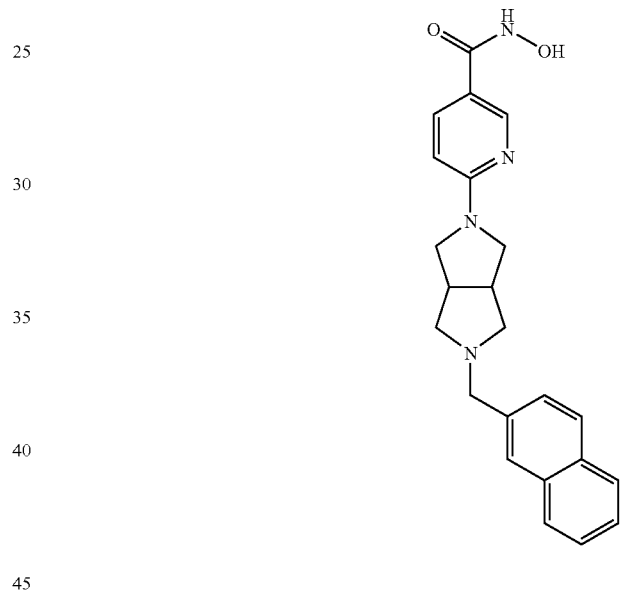

Scheme 18: Preparation of N-hydroxy 6-(5-naphthalen-2-ylmethyl-hexahydro-pyrrolo[3,4-c]pyrrol-2-yl)-nicotinamide

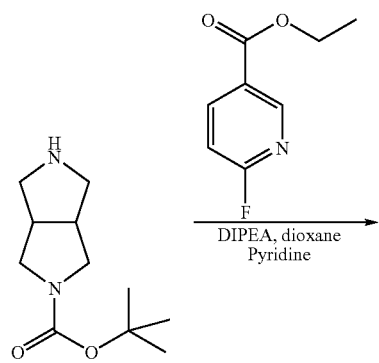

DIPEA, dioxane
Pyridine

Scheme 19: Preparation of N-Hydroxy-4-{6-[(naphthalen-2-ylmethyl)-amino]-3-aza-bicyclo[3.1.0]hex-3-yl}-benzamide

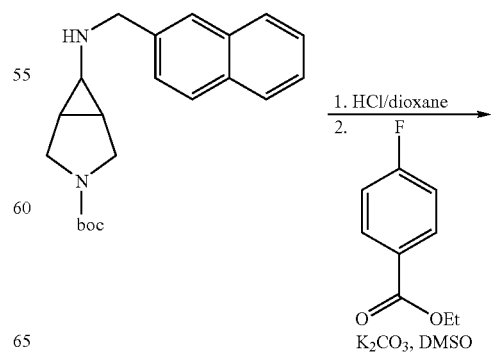

1. HCl/dioxane
2. 4-fluorobenzoate
K$_2$CO$_3$, DMSO

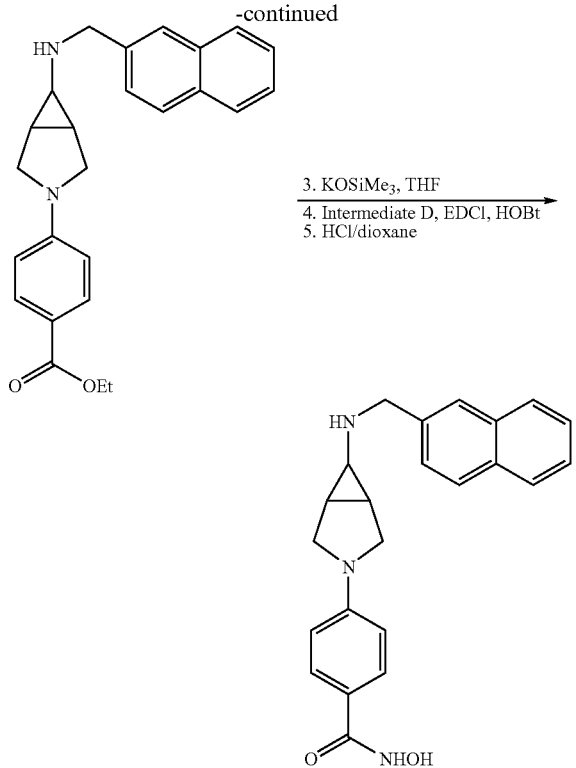

-continued

3. KOSiMe₃, THF
4. Intermediate D, EDCl, HOBt
5. HCl/dioxane

The Following Examples Describe the Preparation of Some Compounds of the Invention, and Indicate their Activities.

Microwave irradiation was carried out using a CEM Discover focused microwave reactor. Solvents were removed using a GeneVac Series I without heating or a Genevac Series II with VacRamp at 30° C. or a Buchi rotary evaporator. Purification of compounds by flash chromatography column was performed using silica gel, particle size 40-63 μm (230-400 mesh) obtained from Silicycle. Purification of compounds by preparative HPLC was performed on Gilson systems using reverse phase ThermoHypersil-Keystone Hyperprep HS C18 columns (12 μm, 100×21.2 mm), gradient 20-100% B (A=water/0.1% TFA, B=acetonitrile/0.1% TFA) over 9.5 min, flow=30 ml/min, injection solvent 2:1 DMSO: acetonitrile (1.6 ml), UV detection at 215 nm.

$^1$H NMR spectra were recorded on a Bruker 400 MHz AV or a Bruker 300 MHz AV spectrometer in deuterated solvents. Chemical shifts (δ) are in parts per million. Thin-layer chromatography (TLC) analysis was performed with Kieselgel 60 F$_{254}$ (Merck) plates and visualized using UV light.

Analytical HPLCMS was performed on Agilent HP1100, Waters 600 or Waters 1525 LC systems using reverse phase Hypersil BDS C18 columns (5 μm, 2.1×50 mm), gradient 0-95% B (A=water/0.1% TFA, B=acetonitrile/0.1% TFA) over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software The following abbreviations have been used:

MeOH = methanol
EtOH = ethanol
EtOAc = ethyl acetate
Boc = tert-butoxycarbonyl
DCM = dichloromethane
DMF = dimethylformamide
DMSO = dimethyl sulfoxide
TFA = trifluoroacetic acid
THF = tetrahydrofuran
Na$_2$CO$_3$ = sodium carbonate
HCl = hydrochloric acid
DIPEA = diisopropylethylamine
NaH = sodium hydride
NaOH = sodium hydroxide
NaHCO$_3$ = sodium hydrogen carbonate
Pd/C = palladium on carbon
TME = tert-butyl methyl ether
N$_2$ = nitrogen
PyBop = (benzotriazol-1-yloxy)-tripyrrolidinophosphonium hexafluorophosphate
Na$_2$SO$_4$ = sodium sulphate
Et$_3$N = triethylamine
NH$_3$ = ammonia
TMSCl = trimethylchlorosilane
NH$_4$Cl = ammonium chloride
LiAlH$_4$ = lithium aluminium hydride
PyBrOP = Bromo-tripyrrolidinophosphonium hexafluorophosphate
MgSO$_4$ = magnesium sulfate
$^n$BuLi = n-butyllithium
CO$_2$ = carbon dioxide
EDCl = N-(3-dimethylaminopropyl)-N'-ethylcarbodiimide hydrochloride
Et$_2$O = diethyl ether
LiOH = lithium hydroxide
HOBt = 1-hydroxybenzotriazole
ELS = evaporative light scattering
TLC = thin layer chromatography
ml = millilitre
g = gram(s)
mg = milligram(s)
mol = moles
mmol = millimole(s)
LCMS = high performance liquid chromatography/mass spectrometry
NMR = nuclear magnetic resonance
r.t. = room temperature
aq. = aqueous
sat. = saturated
h = hour(s)
min = minute(s)

Intermediates

Intermediate A: Ethyl 2-(methylsulfonyl)pyrimidine-5-carboxylate

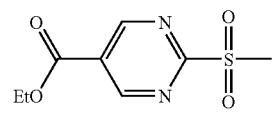

Intermediate A was prepared following the methodology described in Scheme 1.

Ethyl 2-(methylthio)pyrimidine-5-carboxylate

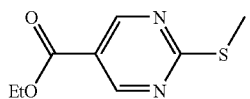

Ethyl 4-chloro-2-methylthio-5-pyrimidine carboxylate (12.5 g, 53.88 mmol) and Zn powder (14.1 g, 215.52 mmol) were combined and benzene (60 ml) and 3M $NH_4Cl$ (140 ml) were added. The suspension was stirred vigorously and heated to 80° C. for 30 h. The reaction mixture was filtered through celite and washed with EtOAc (200 ml). The filtrate was concentrated in vacuo to about 50 ml and then partitioned between $H_2O$ (400 ml) and EtOAc (400 ml). The aqueous layer was further extracted with EtOAc (250 ml). The combined organic layers were dried ($MgSO_4$) and concentrated in vacuo to a dark oil. This was purified by column chromatography eluting with neat heptane followed by 1:1:1 heptane/$CH_2Cl_2$/$Et_2O$ and finally 2:2:0.5 heptane/$CH_2Cl_2$/$Et_2O$. The title compound was obtained as a colourless oil (13 g, 61%). m/z 199 $[M+H]^+$, $^1H$ NMR (300 MHz, $d_6$-DMSO) δ: 1.30 (3H, t), 2.60 (3H, s), 4.35 (2H, q), 9.0 (2H, s).

Ethyl 2-(methylsulfonyl)pyrimidine-5-carboxylate— Intermediate A

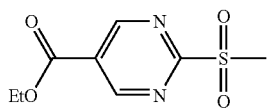

To a stirred solution of ethyl 2-(methylthio)pyrimidine-5-carboxylate (13 g, 47.59 mmol) in dry THF (250 ml) was slowly added over 30 min a solution of mCPBA (47.59 g, 275.76 mmol) in THF (150 ml) at 0° C. under $N_2$. The reaction mixture was allowed to warm to r.t. and stirred for 2 h. The reaction mixture was then concentrated in vacuo to about 100 ml and the product/benzoic acid mixture pre-absorbed onto silica gel. Purification was achieved via chromatography, eluting with neat hexane initially, then 1:5:3 $CH_2Cl_2$/heptane/$Et_2O$, followed by 1:1:1 $CH_2Cl_2$/heptane/$Et_2O$. The title compound was obtained as a white solid (10 g, 66%). m/z 231 $[M+H]^+$, $^1H$ NMR (300 MHz, $d_6$-DMSO) δ: 1.40 (3H, t), 3.50 (3H, s), 4.40 (2H, q), 9.50 (2H, s).

Intermediate B: tert-Butyl 6-aminoazabicyclo[3.1.0]hexane-3-carboxylate

Intermediate B was prepared following the methodology described in Scheme 2.

3-Benzyl-6-nitro-3-azabicyclo[3.1.0]hexane-2,4-dione

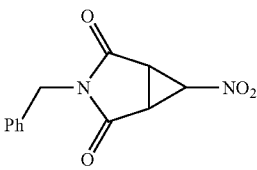

To a solution of N-benzylmaleimide (5.0 g, 26.7 mmol) in MeCN (334 ml) was added bromonitromethane (1.87 ml, 26.7 mmol). $K_2CO_3$ (3.69 g, 26.7 mmol) was added and the reaction mixture vigorously stirred at r.t. After 4 h an additional portion of bromonitromethane (0.2 ml) was added. Further addition of bromonitromethane (0.2 ml) was added at further 4 h intervals (×4). After 48 h, TLC (50% DCM/heptane) indicated reaction completion. The reaction mixture was evaporated to dryness. The brown residue was purified by column chromatography (100% DCM), giving the title compound as a white solid (3.0 g, 42%). $^1H$ NMR (300 MHz, $CDCl_3$) δ: 3.35 (2H, s), 4.50 (1H, s), 4.55 (2H, s), 7.2-7.4 (5H, m).

3-Benzyl-6-nitro-3-azabicyclo[3.1.0]hexane

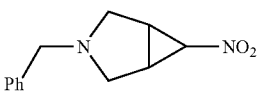

To a solution of 3-benzyl-6-nitro-3-azabicyclo[3.1.0]hexane-2,4-dione (3.0 g, 12.2 mmol) in dry THF (30 ml) was added $NaBH_4$ (1.15 g, 30.48 mmol). The reaction was stirred for 15 min at r.t. under $N_2$. $BF_3$.THF complex (3.15 ml, 13.4 mmol) was added dropwise and the reaction heated at 40° C. for 4 h. Further $NaBH_4$ (0.15 g) was added followed by $BF_3$.THF complex (0.32 ml). Heating was continued at 45° C. for 30 min. A mixture of THF/$H_2O$ (1/1, 60 ml) was added dropwise with stirring. The resulting mixture was heated at 50° C. for 1 h before standing at r.t. for 16 h. The THF was removed to leave mainly water. This was extracted with EtOAc, dried ($MgSO_4$) and evaporated to dryness to give the title compound as a yellow oil (2.47 g, 93%). m/z 219 $[M+H]^+$, $^1H$ NMR (300 MHz, $CDCl_3$) δ: 2.50 (4H, s), 3.15 (2H, d), 3.65 (1H, s), 4.55 (1H, s), 7.2-7.4 (5H, m).

6-Nitro-3-azabicyclo[3.1.0]hexane hydrochloride

To a solution of 3-benzyl-6-nitro-3-azabicyclo[3.1.0]hexane (2.47 g, 11.3 mmol) in 1,2-dichloroethane (5 ml) was added chloroethylchloroformate (1.83 ml, 16.9 mmol) at 0° C. The reaction mixture was heated to 55° C. for 4 h. Further chloroethylchloroformate (0.5 ml) was added and heating continued for 2 h. The reaction mixture was evaporated to dryness. MeOH (15 ml) was added and the reaction mixture was heated at 65° C. for 3 h. Conc. HCl (1 ml) was added and the reaction stirred at r.t. for 2 h. A grey precipitate had formed, this was isolated by filtration and washed with Et$_2$O. The title compound was obtained as a grey powder (464 mg, 25%). $^1$H NMR (300 MHz, d$_6$-DMSO) δ: 2.90 (2H, s), 3.3-3.6 (4H, m), 4.75 (1H, s), 9.50 (2H, br s).

tert-Butyl 6-nitro-3-azabicyclo[3.1.0]hexane-3-carboxylate

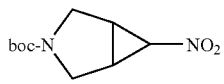

6-Nitro-3-azabicyclo[3.1.0]hexane hydrochloride (464 mg, 2.82 mmol) was suspended in dry DCM (10 ml) and cooled to 0° C. Boc$_2$O (677 mg, 3.10 mmol) was added followed by DMAP (1 crystal) and Et$_3$N (0.43 ml, 3.10 mmol). The reaction mixture was stirred at r.t. for 5 h. The solvent was removed under reduced pressure to give a white solid. Purification by flash chromatography (25% EtOAc in heptane) gave the title compound as a white solid (592 mg, 92%). $^1$H NMR (300 MHz, CDCl$_3$) δ: 1.45 (9H, s), 2.65 (2H, s), 3.50 (2H, d), 3.75 (2H, q), 4.10 (1H, t).

tert-Butyl 6-aminoazabicyclo[3.1.0]hexane-3-carboxylate—Intermediate B

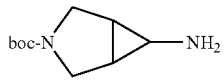

tert-Butyl 6-nitro-3-azabicyclo[3.1.0]hexane-3-carboxylate (592 mg, 2.59 mmol) was reduced in the presence of 10% Pd/C (20 mg) in EtOH (5 ml) under H$_2$ (balloon pressure) for 18 h. The catalyst was removed by filtration through celite. The celite was washed with EtOH and the filtrate concentrated to give the title compound as a pale yellow oil (487 mg, 95%). $^1$H NMR (300 MHz, d$_6$-DMSO) δ: 1.40 (9H, s), 1.7-1.9 (2H, m), 3.2-3.4 (4H, m).

Intermediate C: tert-Butyl 3-azabicyclo[3.1.0]hex-6-ylmethylcarbamate

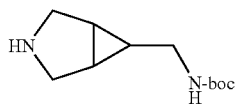

Intermediate C was prepared following the methodology described in Scheme 3.

Ethyl 5-benzyl-4,6-dioxo-1,3a,4,5,6,6a-hexahydropyrrolo[3,4c]pyrazole-3-carboxylate

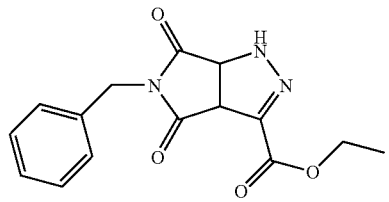

N-Benzylmaleimide (50 g, 267.1 mmol) was dissolved in Et$_2$O (600 ml), treated with ethyldiazoacetate (31 ml, 293.8 mmol) and stirred at r.t. under nitrogen atmosphere for 36 h. A white precipitate had formed so it was isolated by filtration, washed with ice-cold Et$_2$O and dried to give the title compound as a white solid (72 g, 89%). m/z 302 [M+H]$^+$, $^1$H NMR (300 MHz, d$_6$-DMSO) δ: 1.20 (3H, t), 4.15 (2H, q), 4.55 (2H, s), 4.60 (1H, d), 5.00 (1H, d), 7.15-7.35 (5H, m), 9.60 (1H, s).

Ethyl 3-benzyl-2,4-dioxo-3-azabicyclo[3.1.0]hexane-6-carboxylate

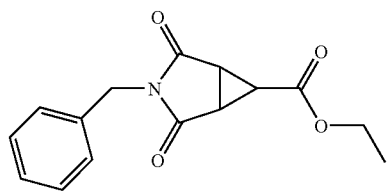

Ethyl 5-benzyl-4,6-dioxo-1,3a,4,5,6,6a-hexahydropyrrolo[3,4c]pyrazole-3-carboxylate (72 g, 239.2 mmol) was heated to 160° C. until it melted to a yellow oil. The oil was heated further to 200° C. and bubbling started. The oil was heated at 200° C. for 30 min until the bubbling had subsided. The now amber-coloured oil was cooled to r.t. and triturated with ice-cold Et$_2$O. The resulting precipitate was filtered and washed with more ice-cold Et$_2$O to give the title compound as a cream solid (37.2 g, 57%). $^1$H NMR (300 MHz, d$_5$-DMSO) δ: 1.20 (3H, t), 2.80 (1H, t), 3.00 (2H, d), 4.15 (2H, q), 4.35 (2H, s), 7.20-7.40 (5H, m).

(3-Benzyl-3-azabicyclo[3.1.0]hex-6-yl)methanol

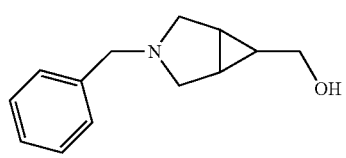

Ethyl 3-benzyl-2,4-dioxo-3-azabicyclo[3.1.0]hexane-6-carboxylate (37.2 g, 136.3 mmol) was dissolved in dry THF (400 ml). This solution was added dropwise at 0° C. to a suspension of LiAlH$_4$ (20.7 g, 545.3 mmol) in dry THF (200 ml). The resulting brown suspension was heated to 60° C. under nitrogen atmosphere for 36 h. The mixture was then cooled to 0° C. and quenched carefully with sat. NH₄Cl. A grey solid formed and more THF was added to allow adequate stirring. Solid Na₂SO₄ was added to the mixture which was stirred at r.t. for 30 min. The mixture was then filtered through celite to give a pale yellow solution. This was concentrated in vacuo to give the title compound as an orange oil (14.1 g, 51%). m/z 204 [M+H]⁺, ¹H NMR (300 MHz, d₆-DMSO) δ: 2.25 (2H, d), 2.85 (2H, d), 3.20 (2H, t), 3.55 (2H, s), 4.35 (1H, t), 7.20-7.40 (5H, m).

3-Benzyl-3-azabicyclo[3.1.0]hexane-6-carbaldehyde

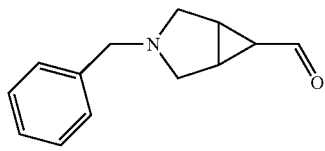

Oxalyl chloride (0.88 ml, 17.73 mmol) was added to a stirred flask of DCM (100 ml) under N₂ and the solution cooled to an internal temperature of −65° C. DMSO (1.26 ml, 17.73 mmol) was then added dropwise, keeping the internal temperature at −65° C. or below at all times. A solution of (3-benzyl-3-azabicyclo[3.1.0]hex-6-yl)methanol (2.00 g, 9.85 mmol) in DCM (50 ml) was then added to the reaction mixture slowly, again making sure the internal temperature did not rise above −65° C. After this addition was complete, triethylamine (5.90 ml, 42.35 mmol) was slowly added to the reaction, again making sure the internal temperature did not rise above −65° C. After addition was complete the reaction was allowed to warm up to r.t. and solvent removed in vacuo. The residue was purified by column chromatography (25% EtOAc in heptane) to give the title compound as a light yellow oil (1.49 g, 76%). LCMS purity 90%, m/z 202 [M+H]⁺, ¹H NMR (300 MHz, d₆-DMSO) δ: 2.11 (2H, m), 2.44 (1H, m), 2.50 (2H, d, J=9.3 Hz), 3.07 (2H, d, J=9.3 Hz), 3.64 (2H, s), 7.21-7.35 (5H, m), 9.31 (1H, d, J=4.8 Hz).

3-Benzyl-3-azabicyclo[3.1.0]hexane-6-carbaldehyde oxime

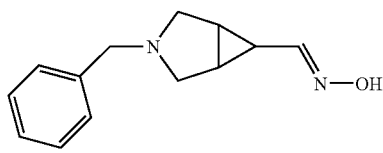

Hydroxylamine hydrochloride (1.69 g, 22.84 mmol) and sodium acetate (2.45 g, 29.85 mmol) were added to a stirred solution of 3-benzyl-3-azabicyclo[3.1.0]hexane-6-carbaldehyde (1.60 g, 7.96 mmol) in EtOH (100 ml) at r.t. under N₂. The reaction was allowed to stir for 16 h. The solvent was then removed in vacuo and the residue partitioned between DCM (100 ml) and aq. K₂CO₃ (100 ml). The organic layer was separated and the aqueous layer washed with DCM (100 ml). The combined organic layers were dried (MgSO₄) and solvent removed in vacuo to give the title compound as a yellow oil (1.57 g, 91%-1:1 mixture of oxime isomers). LCMS purity 85%, m/z 217 [M+H]⁺, ¹H NMR (300 MHz, d₆-DMSO) δ: 1.65 (4H, m), 1.86 (1H, m), 2.29 (4H, d, J=9 Hz), 2.50 (1H, m), 2.91 (4H, dd, J=2.4, 9 Hz), 3.57 (4H, s), 6.05 (1H, d, J=9 Hz), 6.96 (1H, d, J=8.1 Hz), 7.21-7.34 (10H, m), 10.28 (1H, s), 10.59 (1H, s).

(3-Benzyl-3-azabicyclo[3.1.0]hex-6-yl)methylamine

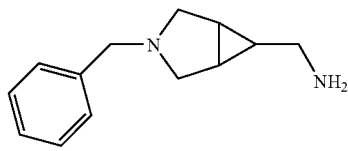

A solution of 3-benzyl-3-azabicyclo[3.1.0]hexane-6-carbaldehyde oxime (1.57 g, 7.27 mmol) in THF (75 ml) was cooled to 0° C. under N₂ and LiAlH₄ (965 mg, 25.44 mmol) was added. The reaction was heated to 60° C. for 16 h and then cooled to 0° C. It was quenched with a mixture of H₂O (3 ml) and sat. aq. sodium potassium tartrate (1 ml) and the resulting suspension stirred for 30 min. MgSO₄ was added and the mixture filtered through celite. The filtrate was then concentrated in vacuo to give the title compound as a light yellow oil (1.35 g, 93%). LCMS purity 80%, m/z 203 [M+H]⁺, ¹H NMR (300 MHz, CDCl₃) δ: 1.21 (4H, m), 1.41 (1H, m), 2.36 (2H, d, J=8.7 Hz), 2.52 (2H, d, J=7.2 Hz), 2.97 (2H, d, J=8.7 Hz), 3.54 (2H, s), 7.20-7.36 (5H).

tert-Butyl (3-benzyl-3-azabicyclo[3.1.0]hex-6-yl)methylcarbamate

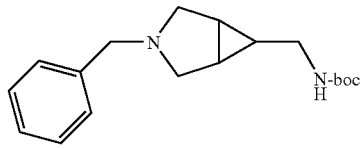

(3-Benzyl-3-azabicyclo[3.1.0]hex-6-yl)methylamine (1.35 g, 6.68 mmol) was stirred in dioxane/H₂O (9:1, 100 ml) at r.t. Triethylamine (1.4 ml, 10.02 mmol) was added followed by Boc₂O (1.46 g, 6.7 mmol) and the reaction stirred for 30 min. H₂O (100 ml) was then added and the solution extracted with Et₂O (2×150 ml). The combined organic extracts were dried (MgSO₄) and solvent removed in vacuo to give the product as a yellow oil (2.01 g, 100%). LCMS purity 95%, m/z 303 [M+H]⁺, ¹H NMR (300 MHz, d₆-DMSO) δ: 1.27 (2H, m), 1.43 (10H, s), 2.35 (2H, dm, J=8.7 Hz), 2.96 (2H, d, J=8.7 Hz), 3.59 (2H, s), 4.66 (1H, br s), 7.21-7.33 (5H, m).

tert-Butyl 3-azabicyclo[3.1.0]hex-6-yl)methylcarbamate—Intermediate C

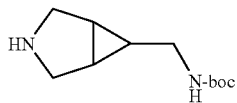

10% Pd/C (2.35 g) and ammonium formate (2.35 g) were added to a stirred solution of tert-butyl (3-benzyl-3-azabicyclo[3.1.0]hex-6-yl)methylcarbamate (2.35 g, 7.78 mmol) and EtOH (90 ml) at r.t. and the reaction stirred for 2 h. The suspension was then filtered through celite and the filtrate concentrated in vacuo. DCM (100 ml) was added to the resultant gummy white solid and the mixture filtered. The filtrate was concentrated in vacuo to give the title compound as a yellow oil (1.2 g, 73%). LCMS purity 95%, m/z 213 [M+H]$^+$, $^1$H NMR (300 MHz, CDCl$_3$) δ: 0.89 (1H, m), 1.26 (2H, m), 1.47 (9H, s), 2.96 (2H, d, J=11.4 Hz), 3.07 (4H, m), 4.62 (2H, br s).

Intermediate D: O-(1-Isobutoxyethyl)hydroxylamine

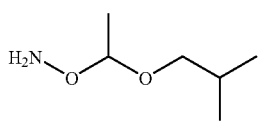

Intermediate D was prepared following the methodology described in WO 01/60785 (see Scheme 4).

$^1$H NMR (300 MHz, d$_6$-DMSO) δ: 0.85 (6H, d), 1.15 (3H, d), 1.75 (1H, m), 3.18 (1H, dd), 3.42 (1H, dd), 4.53 (1H, q), 5.82 (2H, s).

EXAMPLES

Example 1

N-Hydroxy 2-{6-[(2-naphthylsulfonyl)amino]-3-azabicyclo[3.1.0]hex-3-yl}pyrimidine-5-carboxamide trifluoroacetate

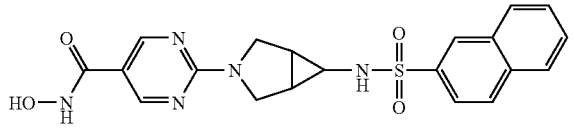

Example 1 was prepared following the methodology described in Scheme 5.

tert-Butyl 6-[(2-napthylsulfonyl)amino]-3-azabicyclo[3.1.0]hexane-3-carboxylate

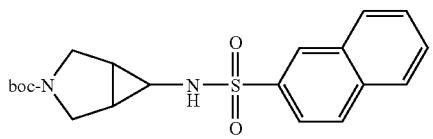

2-Naphtalenesulphonyl chloride (20.07 g, 97.39 mmol) was added in one portion to a solution of intermediate B (17.53 g, 88.54 mmol) and Et$_3$N (24.7 ml, 177.07 mmol) in anhydrous DCM (270 ml) at 0° C. under N$_2$, giving a light brown solution which was allowed to warm to r.t. overnight. The reaction mixture was diluted with DCM (200 ml) and sat. NaHCO$_3$ (200 ml). The organic phase was separated and washed with H$_2$O (2×200 ml), dried (Na$_2$SO$_4$), filtered and concentrated in vacuo to give a pale yellow oil. Trituration with TME and heptane gave a solid which was isolated by filtration and washed with heptane to give the title compound as a white solid (27.99 g, 82%). LCMS purity 100%, m/z 389 [M+H]$^+$, $^1$H NMR (300 MHz, CDCl$_3$) δ: 1.35 (9H, s), 1.82 (2H, m), 1.96 (1H, m), 3.29-3.34 (2H, m), 3.41-3.56 (2H, m), 5.12 (1H, br s), 7.62-7.68 (2H, m), 7.85 (1H, m), 7.93 (1H, d), 7.99-8.02 (2H, m), 8.47 (1H, m).

6-[(2-Napthylsulfonyl)amino]-3-azabicyclo[3.1.0] hexane trifluoroacetate

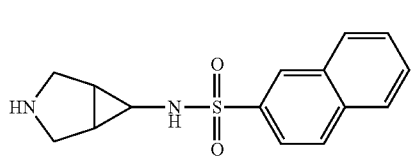

A solution of tert-butyl 6-[(2-napthylsulfonyl)amino]-3-azabicyclo[3.1.0]hexane-3-carboxylate (27.50 g, 68.43 mmol) in 20% TFA in DCM (300 ml) was stirred at r.t. for 2 h. The reaction mixture was concentrated in vacuo and then DCM (100 ml) was added and removed in vacuo three times to remove excess TFA giving the title compound as the trifluoroacetate salt (crude yield=34.0 g). This product was used in the next step without further purification. $^1$H NMR (400 MHz, d$_6$-DMSO) δ: 1.86 (2H, s), 2.20 (1H, m), 3.22 (4H, m), 7.70-7.75 (2H, m), 7.83 (1H, dd), 8.08 (1H, d), 8.18-8.23 (3H, m), 8.33 (1H, br s), 8.48 (1H, s), 9.20 (1H, br s).

Ethyl 2-{6-[2-naphtylsulphonyl)amino]-3-azabicyclo[3.1.0]hex-3-yl}pyrimidine-5-carboxylate

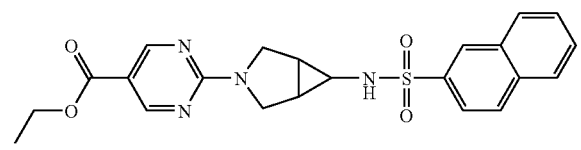

K$_2$CO$_3$ (28.33 g, 205.29 mmol) was added to a stirred suspension of 6-[(2-napthylsulfonyl)amino]-3-azabicyclo[3.1.0]hexane trifluoroacetate (27.50 g, 68.43 mmol) in MeCN (300 ml) at r.t. under N$_2$. A solution of intermediate A (15.74 g, 68.43 mmol) in MeCN (50 ml) was added dropwise over 5 min leading to the formation of a precipitate which was stirred at r.t. overnight. The reaction mixture was diluted with EtOAc (250 ml) giving a suspension which was washed with water (2×250 ml). The precipitate in the organic phase was isolated by filtration, washed with TME and air dried to give the title compound as a white solid (25.40 g, 85%). LCMS purity 96%, m/z 439 [M+H]$^+$, $^1$H NMR (400 MHz, d$_6$-DMSO) δ: 1.26 (3H, t), 1.82 (2H, s), 1.90 (1H, m), 3.50-3.53 (2H, m), 3.67-3.70 (2H, m), 4.23 (2H, q), 7.67-7.71 (2H, m), 7.84 (1H, m), 8.04 (1H, d), 8.15-8.22 (3H, m), 8.50 (1H, m), 8.70 (2H, s).

2-{6-[(2-Napthylsulphonyl)amino]-3-azabicyclo[3.1.0]hex-3-yl}pyrimidine-5-carboxylic acid

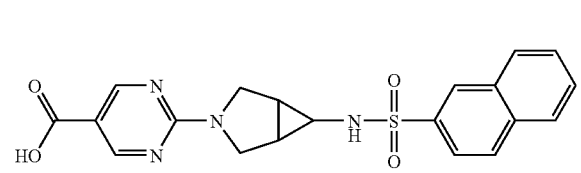

Aqueous 1M NaOH (500 ml) was added to a solution of ethyl 2-{6-[(2-napthylsulphonyl)amino]-3-azabicyclo[3.1.0]hex-3-yl}pyrimidine-5-carboxylate (25.40 g, 58.00 mmol) in THF (500 ml) and MeOH (100 ml) at r.t. The reaction mixture was stirred for 18 h. The organic solvents were removed in vacuo and the resultant aqueous solution was acidified to pH~5 with 1M aq. HCl. A heavy white precipitate was formed which was isolated by filtration, washed with $H_2O$ and dried by azeotroping with toluene, giving the product as a white solid (22.19 g, 93%). LCMS purity 100%, m/z 411 [M+H]$^+$, $^1$H NMR (400 MHz, $d_6$-DMSO) δ: 1.97 (2H, s), 2.05 (1H, s), 3.64-3.67 (2H, m), 3.82-3.89 (2H, m), 7.84-7.88 (2H, m), 8.01 (1H, m), 8.21 (1H, d), 8.31-8.36 (3H, m), 8.66 (1H, s), 8.83 (2H, s).

N-(1-Isobutoxyethoxy) 2-[6-(naphthalene-2-sulfonylamino)-3-azabicyclo[3.1.0]hex-3-yl]pyrimidine-5-carboxamide

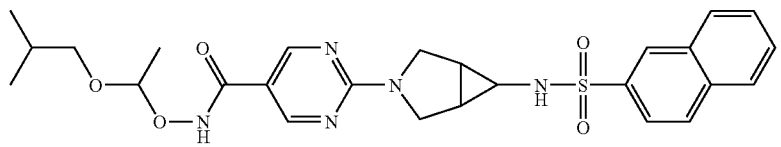

EDCl (7.27 g, 37.9 mmol) was added to a suspension of 2-{6-[(2-napthylsulphonyl)amino]-3-azabicyclo[3.1.0]hex-3-yl}pyrimidine-5-carboxylic acid (22.19 g, 54.12 mmol) in anhydrous DCM (100 ml) and anhydrous THF (500 ml) at r.t. under $N_2$. $Et_3N$ (22.6 ml, 162.14 mmol) was added followed by HOBt (8.78 g, 64.97 mmol) and intermediate D (8.9 ml, 64.89 mmol). After stirring at r.t. for 6 days LCMS indicated 78% conversion to the required product. The reaction mixture was retreated with EDCl (10.25 g, 53.47 mmol), HOBt (7.22 g, 53.43 mmol) and $Et_3N$ (19.4 ml, 139.00 mmol). After stirring for another 3 days at r.t. LCMS showed 96% conversion. The reaction mixture was evaporated to dryness and suspended in EtOAc (100 ml) and water (100 ml). A white solid was collected by filtration, washed with EtOAc (50 ml), water (50 ml), MeOH (50 ml) and dried in vacuo to give the crude product as a white solid (30 g, LCMS purity 92%). This was stirred in EtOH (1500 ml) at 60° C. for 1 h giving a white suspension which was cooled to r.t., filtered and air dried to give the title compound as a white solid (24.0 g, 87%). LCMS purity 97%, m/z 511 [M+H]$^+$, $^1$H NMR (400 MHz, $d_6$-DMSO) δ: 1.60-1.75 (6H, m), 1.80 (2H, s), 1.90 (1H, s), 4.50 (3H, m), 4.65 (2H, d), 4.00 (1H, m), 4.95 (1H, t), 7.60 (2H, m), 7.80-8.30 (4H, d), 8.50 (1H, s), 8.65 (2H, s).

N-Hydroxy 2-{6-[2-naphthylsulfonyl)amino]-3-azabicyclo[3.1.0]hex-3-yl}pyrimidine-5-carboxamide trifluoroacetate—Example 1

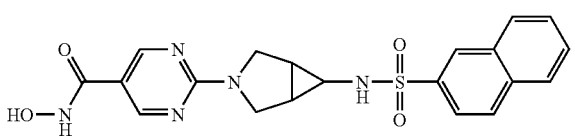

A solution of 4M HCl in dioxane (350 ml) was added portionwise over 5 min to N-(1-isobutoxyethoxy) 2-[6-(naphthalene-2-sulfonylamino)-3-azabicyclo[3.1.0]hex-3-yl]pyrimidine-5-carboxamide (10.0 g, 19.65 mmol) at r.t. with vigorous stirring under $N_2$. After 2 h DCM (20 ml) was added followed by another portion of 4M HCl in dioxane (20 ml) and stirring was continued for a further 2.5 h. The reaction mixture was evaporated in vacuo to ca 200 ml volume and DCM (200 ml) was added portionwise effecting precipitation. The resultant white precipitate was isolated by filtration and washed with DCM (5 ml) giving the title compound as a white powder (6.25 g, 75%). LCMS purity 98%, m/z 426 [M+H]$^+$, $^1$H NMR (400 MHz, $d_6$-DMSO) δ: 1.75 (2H, s), 1.80 (1H, s), 3.20 (1H, s), 3.45 (2H, d), 3.65 (2H, d), 7.45 (2H, m), 7.65 (1H, d), 7.95-8.15 (4H, m), 8.40 (1H, s), 8.50 (2H, s), 11.0 (1H, br s). Anal Calculated for $C_{21}H_{26}ClN_5O_6S$: C, 49.27; H, 5.12; Cl, 6.92; N, 13.68. Found: C, 49.70; H, 5.09; Cl, 7.10; N, 13.55.

Examples 2 to 4 were prepared in an analogous manner to example 1:

Example 2

N-Hydroxy 2-{6-[(thien-2-ylsulfonyl)amino]-3-azabicyclo[3.1.0]hex-3-yl}pyrimidine-5-carboxamide

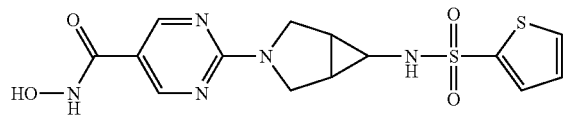

LCMS purity 100%, m/z=282 [M+H]$^+$, 280 [M−H]$^−$, $^1$H NMR (300 MHz, $d_6$-DMSO) δ: 1.82 (2H, s), 1.93 (1H, m), 3.48-3.75 (4H, under solvent peak), 7.22 (1H, t), 7.65 (1H, dd), 7.96 (1H, dd), 8.23 (1H, d), 8.65 (2H, s), 10.55 (1H, br s).

Example 3

N-Hydroxy 2-(6-{[(3,5-bistrifluoromethylphenyl)sulfonyl]amino}-3-azabicyclo[3.1.0]hex-3-1/1)pyrimidine-5-carboxamide

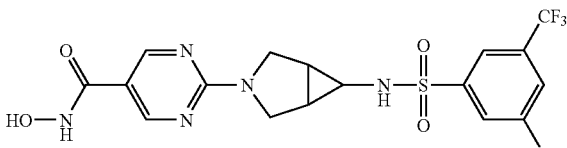

LCMS purity >95%, m/z 512 [M+H]$^+$, $^1$H NMR (300 MHz, $d_6$-DMSO) δ: 1.84 (2H, s), 2.07 (1H, br s), 3.45-3.55

(2H, m), 3.70 (2H, d, J=11.7 Hz), 8.38 (2H, s), 8.47-8.52 (1H, m), 8.54-8.57 (1H, m), 8.62 (2H, s), 9.00 (1H, br s), 11.05 (1H, br s).

Example 4

N-Hydroxy 2-(6-{[(4-trifluoromethoxyphenyl)sulfonyl]amino}-3-azabicyclo[3.1.0]hex-3-yl)pyrimidine-5-carboxamide

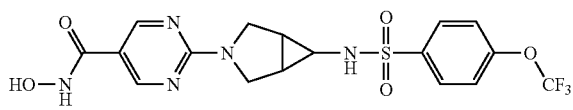

LCMS purity >98%, m/z 460 [M+H]+, 1H NMR (300 MHz, d6-DMSO) δ: 1.81 (2H, m), 1.91 (1H, s), 3.51 (2H, d, J=11.6 Hz), 3.68 (2H, d, J=11.8 Hz), 7.64 (2H, d, J=8.2 Hz), 7.97 (2H, d, J=8.8 Hz), 8.24 (1H, br s), 8.62 (2H, s), 9.01 (1H, br s), 11.07 (1H, br s).

Example 5

N-Hydroxy 2-{6-[(naphthalene-2-carbonyl)amino]-3-aza-bicyclo[3.1.0]hex-3-yl}pyrimidine-5-carboxamide

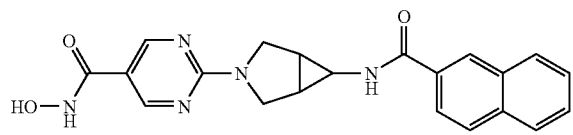

Example 5 was prepared following the methodology described in Scheme 6.

tert-Butyl 6(2-naphthoylamino)-3-azabicyclo[3.1.0]hexane-3-carboxylate

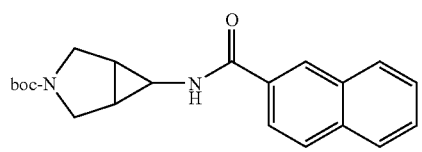

To a cooled (ice-bath) solution of intermediate B (170 mg, 0.86 mmol) in pyridine (1 ml) was added 2-naphthoyl chloride (180 mg, 0.94 mmol). The mixture was stirred for 1 h, then water (8 ml) was added. The resulting precipitate was collected by filtration, and dried under vacuum to afford the title compound (314 mg, 100%). 1H NMR (300 MHz, CDCl3) δ: 1.47 (9H, s), 1.85 (2H, s), 2.71 (1H, d), 3.40-3.50 (2H, m), 3.82 (2H, d), 6.37 (1H, br s), 7.54-7.60 (2H, m), 7.81 (1H, dd), 7.88-7.95 (3H, m), 8.26 (1H, s).

N-Hydroxy 2-{6-[(naphthalene-2-carbonyl)amino]-3-aza-bicyclo[3.1.0]hex-3-yl}-pyrimidine-5-carboxamide—Example 5

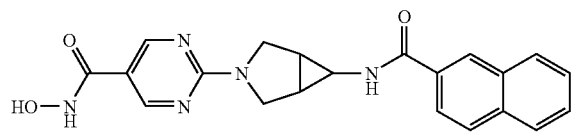

The title compound was prepared from tert-butyl 6-(2-naphthoylamino)-3-azabicyclo[3.1.0]hexane-3-carboxylate following the same methodology described for example 1. LCMS purity >98%, m/z 390 [M+H]+, 1H NMR (300 MHz, d6-DMSO) δ: 2.04 (2H, br s), 2.64-2.70 (1H, m), 3.60-3.70 (2H, m), 3.95 (2H, d, J=11.6 Hz), 7.55-7.66 (2H, m), 7.88-8.05 (4H, m), 8.43 (1H, br s), 8.69 (2H, s), 8.74 (1H, d, J=3.9 Hz), 9.01 (1H, br s), 11.05 (1H, br s).

Examples 6 to 19 were prepared in an analogous manner to example 5:

Example 6

N-Hydroxy 2-(6-{2-[4-(1,1-dioxoisothiazolidin-2-yl)phenyl]acetylamino}-3-azabicyclo[3.1.0]hex-3-yl)pyrimidine-5-carboxamide

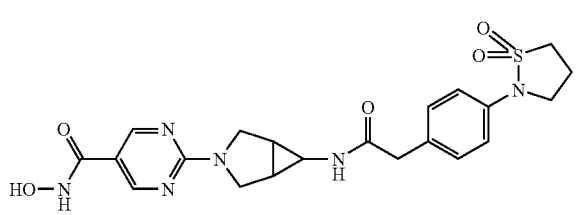

LCMS purity >98%, m/z 473 [M+H]+, 1H NMR (300 MHz, d6-DMSO) δ: 1.81 (2H, br s), 2.32-2.42 (3H, m), 3.33 (2H, s), 3.48 (2H, t, J=7.9 Hz), 3.57 (2H, m), 3.73 (2H, t, J=6.8 Hz), 3.84 (2H, m), 7.14 (2H, d, J=5.5 Hz), 7.24 (2H, d, J=5.5 Hz), 8.28 (1H, d, J=2.5 Hz), 8.64 (2H, s), 11.05 (1H, br s).

Example 7

N-Hydroxy 2-[6-(5-phenylpentanoylamino)-3-azabicyclo[3.1.0]hex-3-yl]pyrimidine-5-carboxamide

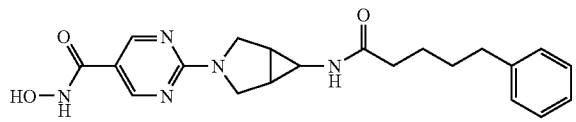

LCMS purity >98%, m/z 396 [M+H]+, 1H NMR (300 MHz, d6-DMSO) δ: 1.52, (4H, m), 1.76 (2H, br s), 2.07 (2H, m), 2.34 (1H, m), 2.58 (2H, m), 3.57 (2H, m), 3.84 (2H, m), 7.14-7.29 (5H, m), 8.00 (1H, d, J=2.5 Hz), 8.67 (2H, s), 11.05 (1H, br s).

Example 8

N-Hydroxy 2-[6-(6-phenylhexanoyl)amino-3-azabicyclo[3.1.0]hex-3-yl]-pyrimidine-5-carboxamide

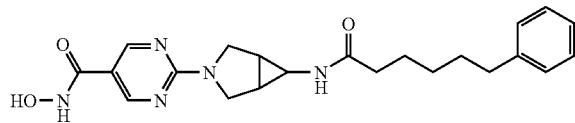

LCMS purity >90%, m/z 140 [M+H]$^+$, $^1$H NMR (300 MHz, d$_6$-DMSO) δ: 1.24 (2H, m), 1.52 (4H, m), 1.75 (2H, br s), 2.02 (2H, t, J=8.6 Hz), 2.33 (1H, m), 2.55 (2H, t, J=9.1 Hz), 3.56 (2H, m), 3.83 (2H, m), 7.13-7.29 (5H, m), 7.97 (1H, d), 8.65 (2H, s), 11.03 (1H, br s).

Example 9

N-Hydroxy 2-(6-{[(1-phenylcyclopropyl)carbonyl]amino}-3-aza bicyclo[3.1.0]hex-3-yl)pyrimidine-5-carboxamide

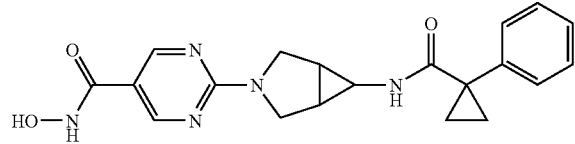

LCMS purity >99%, m/z 380 [M+H]$^+$, $^1$H NMR (300 MHz, d$_6$-DMSO) δ: 0.96 (2H, dd, J=5.8, 7.2 Hz), 1.32 (2H, dd, J=5.8, 7.2 Hz), 1.79 (2H, br s), 2.31 (1H, m), 3.52 (2H, dm), 3.79 (2H, d), 7.06 (1H, d, J=11.0 Hz), 7.23-7.40 (5H, m), 8.64 (2H, s), 8.99 (1H, br s), 11.04 (1H, s).

Example 10

N-Hydroxy 2-{6-[(2-phenylpropanoyl)amino]-3-azabicyclo[3.1.0]hex-3-yl}pyrimidine-5-carboxamide

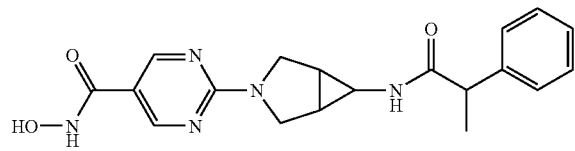

LCMS purity >99%, m/z 368 [M+H]$^+$, $^1$H NMR (300 MHz, d$_6$-DMSO) δ: 1.31 (3H, d, J=9.2 Hz), 1.76 (2H, m), 2.35 (1H, m), 3.54 (3H, m), 3.82 (2H, dd, J=1.9, 9.5 Hz), 7.18-7.35 (5H, m), 8.18 (1H, d), 8.64 (2H, s), 8.99 (1H, br s), 11.05 (1H, s).

Example 11

N-Hydroxy 2-{6-[(thien-3-ylacetyl)amino]-3-azabicyclo[3.1.0]hex-3-yl}pyrimidine-5-carboxamide

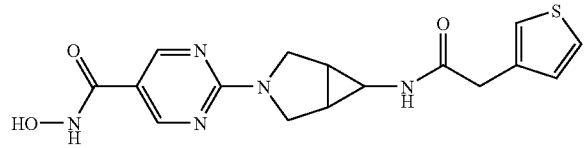

LCMS purity >98%, m/z 360 [M+H]$^+$, $^1$H NMR (300 MHz, d$_6$-DMSO) δ: 1.80 (2H, br s), 2.28 (1H, m), 3.33 (2H, s), 3.56 (2H, dm, J=11.7 Hz), 3.83 (2H, d), 7.01 (1H, dd, J=3.9, 1.2 Hz), 7.22 (1H, d, J=2.1 Hz), 7.45 (1H, dd, J=2.1, 1.2 Hz), 8.23 (1H, d, J=3.9 Hz), 8.65 (2H, s), 8.99 (1H, br s), 11.05 (1H, br s).

Example 12

N-Hydroxy 2-{6-[(cyclohexylcarbonyl)amino]-3-azabicyclo[3.1.0]hex-3-yl}pyrimidine-5-carboxamide

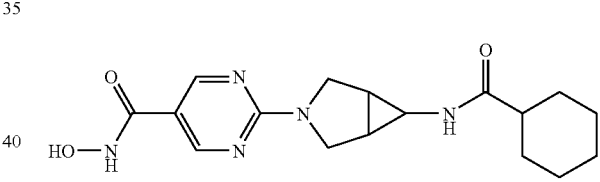

LCMS purity >98%, m/z 346.2 [M+H]$^+$, $^1$H NMR (300 MHz, d$_6$-DMSO) δ: 1.05-1.40 (4H, m), 1.55-1.80 (8H, m), 1.95-2.10 (1H, m), 2.30-2.38 (1H, m), 3.50-3.60 (2H, m), 3.82 (2H, d, J=11.7 Hz), 7.88 (1H, d, J=4 Hz), 8.65 (2H, s), 8.99 (1H, br s), 11.07 (1H, br s).

Example 13

N-Hydroxy 2-[6-(benzoylamino)-3-azabicyclo[3.1.0]hex-3-yl]pyrimidine-5-carboxamide

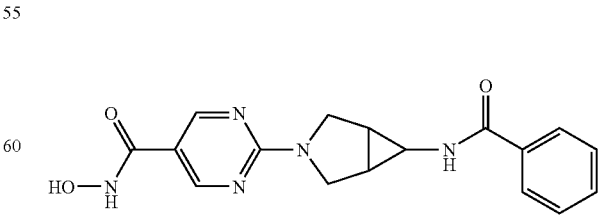

LCMS purity >98%, m/z 339.4 [M+H]$^+$, $^1$H NMR (300 MHz, d$_6$-DMSO) δ: 1.98 (2H, br s), 2.55-2.63 (1H, m), 3.62 (2H, d, J=11.7 Hz), 3.92 (2H, d, J=11.7 Hz), 7.41-7.58 (3H, m), 7.83 (2H, m), 8.60 (1H, d, J=3.9 Hz), 8.67 (2H, s), 8.95-9.05 (1H, br s), 11.08 (1H, s).

Example 14

N-Hydroxy 2-{6-[2-(1-methyl-1H-indol-3-yl)acetylamino]-3-aza-bicyclo[3.1.0]hex-3-yl}pyrimidine-5-carboxamide

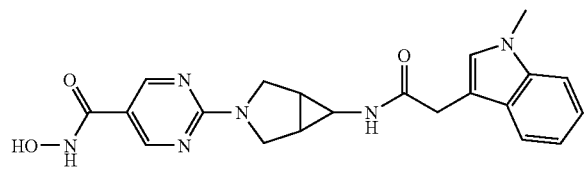

LCMS purity >98%, m/z 407 [M+H]$^+$, $^1$H NMR (300 MHz, d$_6$-DMSO) δ: 1.80 (2H, br s), 2.35-2.40 (1H, m), 2.45 (2H, s), 3.52-3.60 (2H, m), 3.74 (3H, s), 3.83 (2H, d, J=11.7 Hz), 7.02 (1H, m), 7.10-7.18 (2H, m), 7.37 (1H, d, J=8.2 Hz), 7.53 (1H, d, J=7.9 Hz), 8.19 (1H, d, J=3.7 Hz), 8.64 (2H, s), 8.98 (1H, br s), 11.01 (1H, br s).

Example 15

N-Hydroxy 2-[6-(4-phenoxybutyrylamino)-3-azabicyclo[3.1.0]hex-3-yl]pyrimidine-5-carboxamide

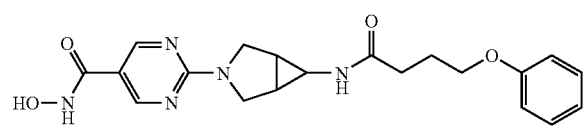

LCMS purity >98%, m/z 398 [M+H]$^+$, $^1$H NMR (300 MHz, d$_6$-DMSO) δ: 1.76-1.81 (2H, m), 1.86-1.98 (2H, m), 2.22 (2H, t, J=7.5 Hz), 2.34-2.38 (1H, m), 3.52-3.61 (2H, m), 3.83 (1H, d, J=11.7 Hz), 3.94 (2H, t, J=6.3 Hz), 6.88-6.95 (3H, m), 7.28 (2H, dd, J=8.3, 8.3 Hz), 8.07 (1H, d, J=3.8 Hz), 8.65 (2H, s), 8.99 (1H, br s), 11.06 (1H, br s).

Example 16

N-Hydroxy 2-{6-[(1-benzofuran-5-ylcarbonyl)amino]-3-azabicyclo[3.1.0]hex-3-yl}pyrimidine-5-carboxamide

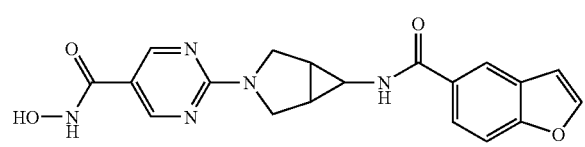

LCMS purity >99%, m/z 380 [M+H]$^+$, $^1$H NMR (300 MHz, d$_6$-DMSO) δ: 1.99 (2H, br s), 2.62 (1H, m), 3.62 (2H, dm, J=11.7 Hz), 3.92 (2H, d, J=11.7 Hz), 7.06 (1H, m), 7.66 (1H, d, J=8.5 Hz), 7.81 (1H, dd, J=8.5, 1.8 Hz), 8.08 (1H, d, J=1.8 Hz), 8.17 (1H, d, J=1.8 Hz), 8.61 (1H, d, J=3.9 Hz), 8.68 (2H, s), 9.00 (1H, br s), 11.07 (1H, br s).

Example 17

N-Hydroxy 2-{6-[(1-benzothien-5-ylcarbonyl)amino]-3-azabicyclo[3.1.0]hex-3-yl}pyrimidine-5-carboxamide

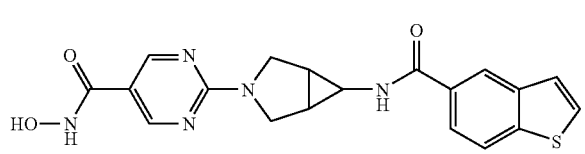

LCMS purity 97%, m/z 395 [M+H]$^+$, $^1$H NMR (300 MHz, d$_6$-DMSO) δ: 2.01 (2H, br s), 2.64 (1H, m), 3.63 (2H, dm, J=11.7 Hz), 3.93 (2H, d, J=11.7 Hz), 7.55 (1H, d, J=5.4 Hz), 7.81 (1H, dd, J=8.6, 1.5 Hz), 7.86 (1H, d, J=5.4 Hz), 8.08 (1H, d, J=8.6 Hz), 8.37 (1H, d, J=1.2 Hz), 8.68 (3H, m), 8.99 (1H, br s), 11.05 (1H, br s).

Example 18

N-Hydroxy 2-{6-[(thien-2-ylcarbonyl)amino]-3-azabicyclo[3.1.0]hex-3-yl}pyrimidine-5-carboxamide

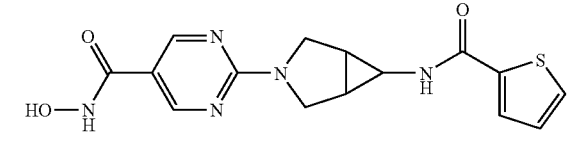

LCMS purity >98%, m/z 346 [M+H]$^+$, $^1$H NMR (300 MHz, d$_6$-DMSO) δ: 1.97 (2H, m), 2.64 (1H, m), 3.57-3.66 (2H, m), 3.90 (2H, d, J=11.6 Hz), 7.12-7.18 (1H, m), 7.72-7.78 (2H, m), 8.63-8.65 (1H, m), 8.67 (2H, m), 11.07 (1H, br s).

Example 19

N-Hydroxy 2-[6-(2-biphenyl-4-yl-acetylamino)-3-azabicyclo[3.1.0]hex-3-yl]pyrimidine-5-carboxamide

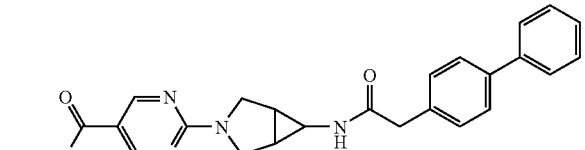

LCMS purity 97%, m/z 430 [M+H]$^+$, 428 [M+H]$^-$, $^1$H NMR (300 MHz, d$_6$-DMSO) δ: 1.82 (2H, br s), 2.39 (1H, br s), 3.42 (2H, s), 3.57 (2H, d, J=9.6 Hz), 3.84 (2H, d, J=11.6

Hz), 7.34 (3H, m), 7.46 (2H, m), 7.62 (4H, m), 8.34 (1H, d, J=4.1 Hz), 8.65 (2H, s), 9.00 (1H, br s), 11.07 (1H, br s).

Example 20

N-Hydroxy 2-{6-[(2-naphthylmethyl)amino]-3-azabicyclo[3.1.0]hex-3-yl}pyrimidine-5-carboxamide

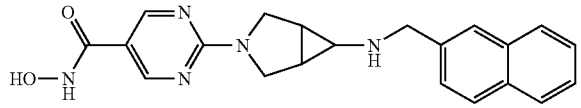

Example 20 was prepared following the methodology described in Scheme 7.

tert-Butyl 6-(naphthalene-2-methylamino)-3-azabicyclo[3.1.0]hexane-3-carboxylate

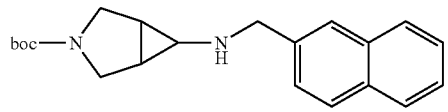

Intermediate B (200 mg, 1.01 mml) was stirred in MeOH (10 ml) at r.t. under $N_2$ and 2-napthaldehyde (148 mg, 0.96 mmol) was added. The resultant solution was stirred for 3 h. After this time, NaBH$_4$ (61 mg, 1.62 mmol) was added, causing fizzing, and the solution stirred for 10 min. 1M NaOH (20 ml) was then added, forming an opaque white solution which was stirred for 20 min. H$_2$O (50 ml) was then added and the solution extracted with Et$_2$O (2×100 ml). The combined organic extracts were dried (MgSO$_4$) and solvent removed in vacuo to give the title compound as a colourless oil (320 mg, 100%). LCMS purity 98%, m/z 339 [M+H]$^+$.

N-Hydroxy 2-{6-[(2-naphthylmethyl)amino]-3-azabicyclo[3.1.0]hex-3-yl}pyrimidine-5-carboxamide—Example 20

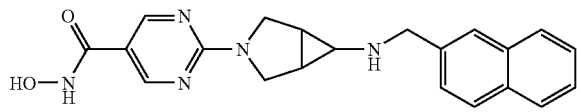

The title compound was prepared from tert-butyl 6-(naphthalene-2-methylamino)-3-azabicyclo[3.1.0]hexane-3-carboxylate following the same methodology described for example 1. LCMS purity >99%, m/z 375 [M+H]$^+$, $^1$H NMR (300 MHz, d$_6$-DMSO) δ: 2.22 (2H, br s), 2.57 (1H, m), 3.56 (2H, dm, J=11.7 Hz), 3.80 (2H, d, J=11.7 Hz), 4.41 (2H, s), 7.57 (2H, m), 7.67 (1H, dd, J=8.4, 1.8 Hz), 7.97 (3H, m), 8.07 (1H, s), 8.66 (2H, s), 9.01 (1H, br s), 9.61 (1H, br s), 11.10 (1H, br s).

Examples 21 to 44 were prepared in an analogous manner to example 20:

Example 21

N-Hydroxy 2-{6-[(4-methoxybenzyl)amino]-3-azabicyclo[3.1.0]hex-3-yl}pyrimidine-5-carboxamide

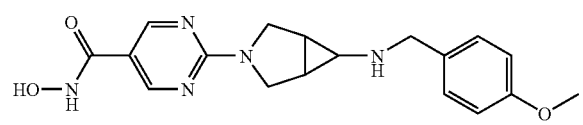

LCMS purity 100%, m/z 382 [M+H]$^+$, $^1$H NMR (300 MHz, CD$_3$OD) δ: 1.45 (2H, m), 1.73 (4H, m), 2.25 (2H, br s), 2.59 (1H, m), 2.66 (2H, t, J=8.9 Hz), 3.14 (2H, t, J=10.1 Hz), 3.68 (2H, dm, J=10.8 Hz), 4.06 (2H, d, J=10.8 Hz), 7.10-7.30 (5H, m), 8.69 (2H, s).

Example 22

N-Hydroxy 2-[6-(4-phenoxybenzylamino)-3-azabicyclo[3.1.0]hex-3-yl]pyrimidine-5-carboxamide

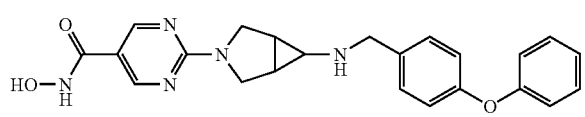

LCMS purity >97%, m/z 418 [M+H]$^+$, $^1$H NMR (300 MHz, d$_6$-DMSO) δ: 2.15 (2H, br s), 2.58 (1H, m), 3.58 (2H, m), 3.83 (2H, d, J=11.7 Hz), 4.26 (2H, br s), 7.02 (2H, d, J=7.8 Hz), 7.05 (2H, d, J=7.2 Hz), 7.18 (1H, t, J=5.4 Hz), 7.42 (2H, td, J=7.5, 2.1 Hz), 7.51 (2H, d, J=8.4 Hz), 8.48 (2H, s), 9.23 (1H, br s), 11.05 (1H, br s).

Example 23

N-Hydroxy 2-[6-(4-butylbenzylamino)-3-azabicyclo[3.1.0]hex-3-yl]pyrimidine-5-carboxamide

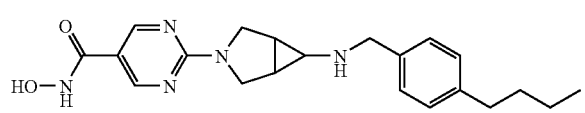

LCMS purity 97%, m/z 382 [M+H]$^+$, $^1$H NMR (300 MHz, CD$_3$OD) δ: 0.95 (3H, t, J=7.2 Hz), 1.37 (2H, m), 1.61 (2H, m), 2.19 (2H, br s), 2.58 (1H, m), 2.70 (2H, t, J=7.5 Hz), 3.65 (2H, dm, J=12 Hz), 4.01 (2H, d, J=12 Hz), 4.33 (2H, s), 7.31 (2H, d, J=8.1 Hz), 7.42 (2H, d, J=8.1 Hz), 8.69 (2H, s).

Example 24

N-Hydroxy 2-{6-[(2-phenylpropyl)amino]-3-azabicyclo[3.1.0]hex-3-yl}pyrimidine-5-carboxamide

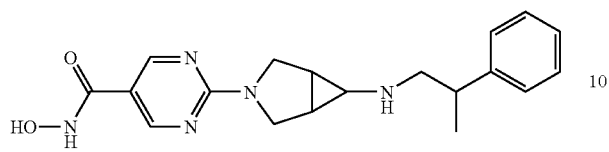

LCMS purity 97%, m/z 354 [M+H]$^+$, $^1$H NMR (300 MHz, CD$_3$OD) δ: 1.36 (3H, d, J=6.9 Hz), 2.23 (2H, m), 2.50 (1H, br s), 3.14 (1H, m), 3.41 (2H, m), 3.63 (2H, m), 3.98 (2H, dd, J=11.7, 6.6 Hz), 7.26-7.41 (5H, m), 8.67 (2H, s).

Example 25

N-Hydroxy 2-{6-[(cyclohexylmethyl)amino]-3-azabicyclo[3.1.0]hex-3-yl}pyrimidine-5-carboxamide

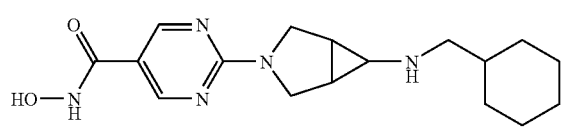

LCMS purity 98%, m/z 382 [M+H]$^+$, $^1$H NMR (300 MHz, CD$_3$OD) δ: 0.97-1.25 (4H, m), 1.60-1.85 (7H, m), 2.19 (2H, br s), 2.49 (1H, br s), 2.98 (2H, d, J=6.9 Hz), 3.69 (2H, dm, J=12 Hz), 4.08 (2H, d, J=12 Hz), 8.69 (2H, s).

Example 26

N-Hydroxy 2-{6-[(4-methoxybenzyl)amino]-3-azabicyclo[3.1.0]hex-3-yl}pyrimidine-5-carboxamide

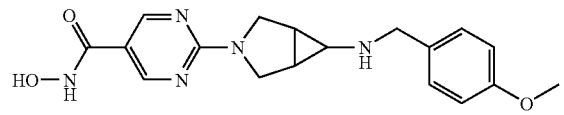

LCMS purity 98%, m/z 356 [M+H]$^+$, $^1$H NMR (300 MHz, d$_6$-DMSO) δ: 2.13 (2H, br s), 2.57 (1H, br s), 3.56 (2H, dm, J=11.7 Hz), 3.82 (2H, d, J=11.7 Hz), 4.20 (2H, br s), 7.00 (2H, d, J=8.7 Hz), 7.42 (2H, d, J=8.7 Hz), 8.67 (2H, s), 9.04 (1H, s), 9.14 (1H, br s), 11.10 (1H, br s).

Example 27

N-Hydroxy 2-{6-[(biphenyl-4-ylmethyl)-amino]-3-aza-bicyclo[3.1.0]hex-3-yl}pyrimidine-5-carboxamide

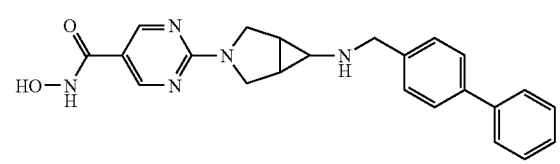

LCMS purity 98%, m/z 402 [M+H]$^+$, $^1$H NMR (300 MHz, d$_6$-DMSO) δ: 2.19 (2H, br s), 2.63 (1H, br s), 3.59 (2H, dm, J=11.7 Hz), 3.84 (2H, d, J=11.7 Hz), 4.33 (2H, br s), 7.10-7.30 (2H, m), 7.35-7.75 (8H, m), 8.67 (2H, s), 9.34 (1H, br s), 11.05 (1H, br s).

Example 28

N-Hydroxy 2-{6-[(3,5-difluorobenzyl)amino]-3-azabicyclo[3.1.0]hex-3-yl}pyrimidine-5-carboxamide

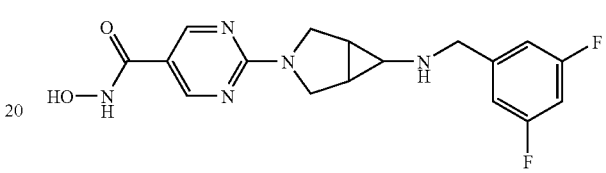

LCMS purity 98%, m/z 362 [M+H]$^+$, $^1$H NMR (300 MHz, d$_6$-DMSO) δ: 2.15 (2H, br s), 2.61 (1H, m), 3.58 (2H, dm, J=11.7 Hz), 3.82 (2H, d, J=11.7 Hz), 4.30 (2H, br s), 7.28 (2H, m), 7.37 (1H, m), 8.67 (2H, m), 9.37 (1H, br s), 10.19 (1H, br s), 11.10 (1H, br s).

Example 29

N-Hydroxy 2-[6-(3-phenylbutylamino)-3-aza-bicyclo[3.1.0]hex-3-yl]pyrimidine-5-carboxamide

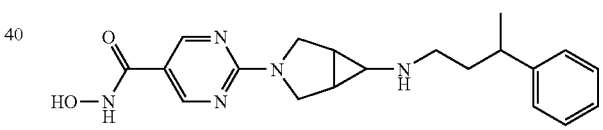

LCMS purity 99%, m/z 368 [M+H]$^+$, $^1$H NMR (300 MHz, d$_6$-DMSO) δ: 1.22 (3H, d, J=6.9 Hz), 1.87 (2H, q, J=7.8 Hz), 2.17 (2H, br s), 2.64 (1H, br s), 2.78 (2H, m), 2.98 (1H, m), 3.57 (2H, dm, J=11.7 Hz), 3.86 (2H, d, J=11.7 Hz), 7.19-7.35 (5H, m), 8.66 (2H, s), 8.82 (1H, br s), 9.01 (1H, m), 11.08 (1H, s).

Example 30

N-Hydroxy 2-{6-[(4-chlorobenzyl)amino]-3-azabicyclo[3.1.0]hex-3-yl}pyrimidine-5-carboxamide

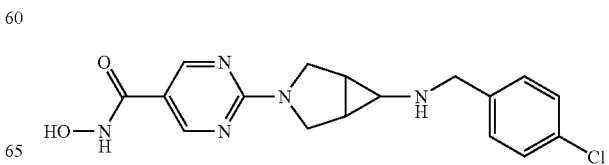

LCMS purity >98%, m/z 362 [M+H]⁺, ¹H NMR (300 MHz, d₆-DMSO) δ: 2.13 (2H, br s), 2.57 (1H, br s), 3.57 (2H, dm, J=11.7 Hz), 3.71 (2H, d, J=11.7 Hz), 4.27 (2H, s), 7.54 (4H, m), 8.67 (2H, s), 9.04 (1H, br s), 9.26 (1H, br s), 11.07 (1H, br s).

Example 31

N-Hydroxy 2-{6-[(4-cyanobenzyl)amino]-3-azabicyclo[3.1.0]hex-3-yl}pyrimidine-5-carboxamide

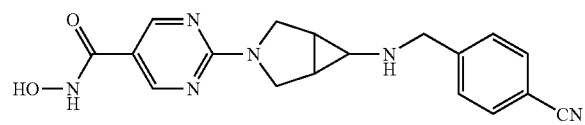

LCMS purity >98%, m/z 351 [M+H]⁺, ¹H NMR (300 MHz, CD₃OD) δ: 2.26 (2H, br s), 2.65 (1H, br s), 3.67 (2H, dm, J=11.7 Hz), 4.03 (2H, d, J=11.7 Hz), 4.47 (2H, br s), 7.71 (2H, d, J=7.8 Hz), 7.87 (2H, d, J=7.8 Hz), 8.67 (2H, s).

Example 32

N-Hydroxy 2-{6-[(1-benzothien-3-ylmethyl)amino]-3-azabicyclo[3.1.0]hex-3-yl}pyrimidine-5-carboxamide

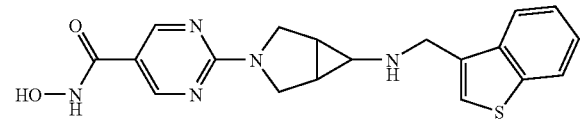

LCMS purity >98%, m/z 382 [M+H]⁺, ¹H NMR (300 MHz, d₆-DMSO) δ: 2.15 (2H, br s), 2.64 (1H, br s), 3.54 (2H, dm, J=11.7 Hz), 3.81 (2H, d, J=11.7 Hz), 4.57 (2H, s), 7.45 (2H, m), 7.97 (1H, s), 8.07 (2H, dd, J=7.8, 0.9 Hz), 8.67 (2H, s), 9.04 (1H, br s), 9.32 (1H, br s), 11.10 (1H, br s).

Example 33

N-Hydroxy 2-[6-(benzylamino)-3-azabicyclo[3.1.0]hex-3-yl]pyrimidine-5-carboxamide

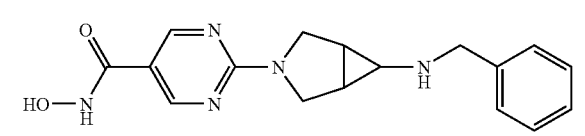

LCMS purity >98%, m/z 326 [M+H]⁺, ¹H NMR (300 MHz, d₆-DMSO) δ: 2.13 (2H, br s), 2.57 (1H, br s), 3.56 (2H, dm, J=11.7 Hz), 3.82 (2H, d, J=11.7 Hz), 4.26 (2H, s), 7.42-7.51 (5H, m), 8.67 (2H, s), 9.02 (1H, br s), 9.20 (1H, br s), 11.09 (1H, br s).

Example 34

N-Hydroxy 2-{6-[(4-trifluoromethoxybenzyl)amino]-3-azabicyclo[3.1.0]hex-3-yl}pyrimidine-5-carboxamide

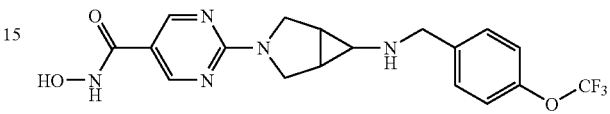

LCMS purity >98%, m/z 410 [M+H]⁺, ¹H NMR (300 MHz, d₆-DMSO) δ: 2.15 (2H, br s), 2.60 (1H, br s), 3.57 (2H, dm, J=11.7 Hz), 3.83 (2H, d, J=11.7 Hz), 4.31 (2H, s), 7.25 (2H, d, J=8.7 Hz), 7.64 (2H, d, J=8.7 Hz), 8.67 (2H, s), 9.02 (1H, br s), 9.28 (1H, br s), 11.07 (1H, br s).

Example 35

N-Hydroxy 2-{6-[(3,5-bistrifluoromethylbenzyl)amino]-3-azabicyclo[3.1.0]hex-3-yl}pyrimidine-5-carboxamide

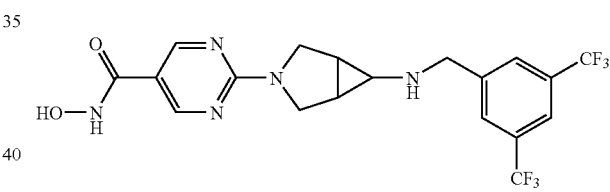

LCMS purity >97%, m/z 462 [M+H]⁺, ¹H NMR (300 MHz, CD₃OD) δ: 2.27 (2H, br s), 2.67 (1H, br s), 3.68 (2H, dm, J=12 Hz), 4.06 (2H, d, J=12 Hz), 4.56 (2H, s), 8.13 (1H, m), 8.20 (2H, m), 8.69 (2H, s).

Example 36

N-Hydroxy 2-{6-[(4-bromobenzyl)amino]-3-azabicyclo[3.1.0]hex-3-yl}pyrimidine-5-carboxamide

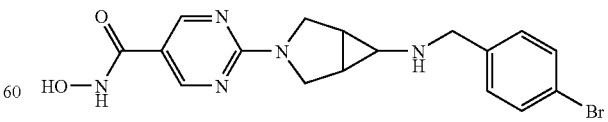

LCMS purity >99%, m/z 406 [M+H]⁺, ¹H NMR (300 MHz, d₆-DMSO) δ: 2.18 (2H, br s), 3.56 (2H, dm, J=11.7 Hz), 3.81 (2H, dm, J=11.7 Hz), 4.23 (2H, s), 7.49 (2H, d, J=8.4 Hz), 7.67 (2H, d, J=8.4 Hz), 8.67 (2H, s), 9.01 (1H, br s), 9.49 (1H, br s), 11.10 (1H, br s).

Example 37

N-Hydroxy 2-{6-[(biphenyl-3-ylmethyl)-amino]-3-aza-bicyclo[3.1.0]hex-3-yl}pyrimidine-5-carboxamide

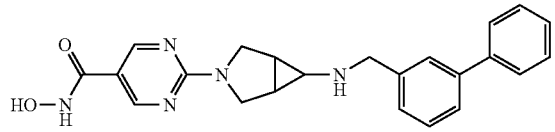

LCMS purity 98%, m/z 402 [M+H]+, 1H NMR (300 MHz, d6-DMSO) δ: 2.26 (2H, br s), 2.57 (1H, br s), 3.57 (2H, d, J=11.7 Hz), 3.83 (2H, d, J=11.7 Hz), 4.32 (2H, br s), 7.40 (1H, m), 7.47-7.54 (4H, m), 7.73 (2H, m), 7.93 (1H, s), 8.67 (2H, s), 9.75 (2H, br s), 11.10 (1H, br s).

Example 38

N-Hydroxy 2-{6-[(2-phenylethyl)amino]-3-azabicyclo[3.1.0]hex-3-yl}pyrimidine-5-carboxamide

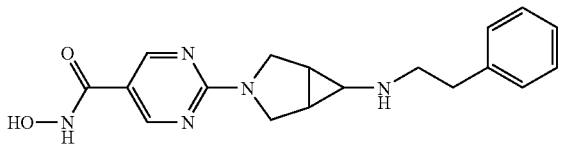

LCMS purity 99%, m/z 340 [M+H]+, 1H NMR (300 MHz, CD3OD) δ: 2.05 (2H, br s), 2.61 (1H, br s), 3.03 (2H, m), 3.37 (2H, m), 3.67 (2H, dm, J=11.7 Hz), 4.03 (2H, d, J=11.7 Hz), 7.27-7.38 (5H, m), 8.68 (2H, s).

Example 39

N-Hydroxy 2-[6-(3,3-diphenylpropylamino)-3-azabicyclo[3.1.0]hex-3-yl]pyrimidine-5-carboxamide

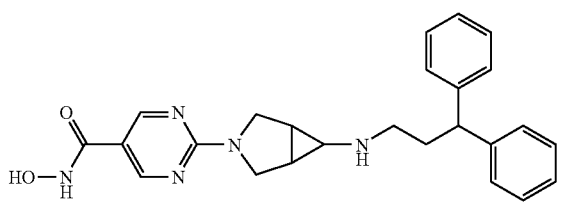

LCMS purity >98%, m/z 430 [M+H]+, 1H NMR (300 MHz, CD3OD) δ: 2.11 (2H, br s), 2.42 (3H, m), 2.99 (2H, m), 3.64 (2H, dm, J=11.7 Hz), 3.97 (2H, d, J=11.7 Hz), 4.06 (1H, t, J=8.1 Hz), 7.20 (2H, m), 7.31 (8H, m), 8.67 (2H, s).

Example 40

N-Hydroxy 2-{6-[(2,2,2-trifluoro-1-phenylethyl)amino]-3-azabicyclo[3.1.0]hex-3-yl}pyrimidine-5-carboxamide

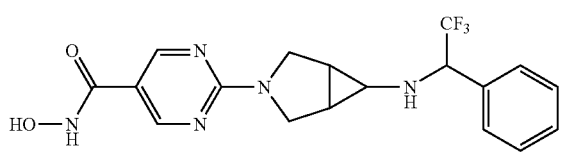

LCMS purity >98%, m/z 394 [M+H]+, 1H NMR (300 MHz, CD3OD) δ: 1.72 (3H, m), 3.48 (2H, m), 3.61 (2H, m), 4.23 (1H, m), 7.23-7.37 (5H, m), 8.50 (2H, s).

Example 41

N-Hydroxy 2-{6-[(4-fluorobenzyl)amino]-3-azabicyclo[3.1.0]hex-3-yl}pyrimidine-5-carboxamide

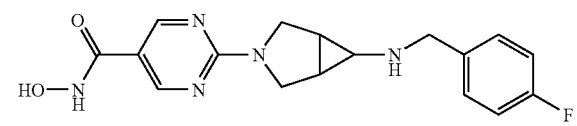

LCMS purity >98%, m/z 344 [M+H]+, 1H NMR (300 MHz, d6-DMSO) δ: 2.27 (2H, m), 2.57 (1H, m), 3.58 (2H, dm, J=11.7 Hz), 3.84 (2H, d, J=11.7 Hz), 4.30 (2H, m), 7.35 (2H, m), 7.68 (2H, m), 8.73 (2H, s), 9.83 (2H, m), 11.20 (1H, m).

Example 42

N-Hydroxy 2-(6-{[(4-(trifluoromethyl)benzyl]amino}-3-azabicyclo[3.1.0]hex-3-yl)pyrimidine-5-carboxamide

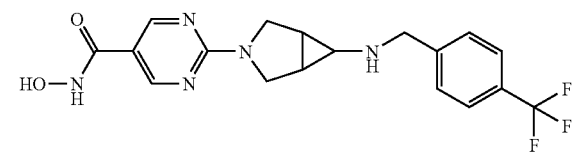

LCMS purity >98%, m/z 394 [M+H]+, 1H NMR (300 MHz, d6-DMSO) δ: 2.27 (2H, m), 2.55 (1H, m), 3.57 (2H, dm, J=11.7 Hz), 3.80 (2H, d, J=11.7 Hz), 4.59 (2H, m), 7.56 (2H, d, J=8.1 Hz), 7.68 (2H, d, J=8.1 Hz), 8.68 (2H, s), 10.01 (2H, m), 11.10 (1H, m).

Example 43

N-Hydroxy 2-{6-[(quinolin-2-ylmethyl)amino]-3-azabicyclo[3.1.0]hex-3-yl}pyrimidine-5-carboxamide

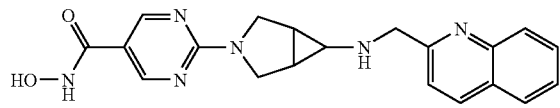

LCMS purity >98%, m/z 377 [M+H]⁺, ¹H NMR (300 MHz, CD₃OD) δ: 2.28 (2H, br s), 2.67 (1H, br s), 3.59 (2H, dm, J=11.7 Hz), 3.98 (2H, d, J=11.7 Hz), 4.64 (2H, s), 7.43 (1H, d, J=8.4 Hz), 7.54 (1H, t, J=7.2 Hz), 7.70 (1H, t, J=7.2 Hz), 7.87 (1H, d, J=8.4 Hz), 8.01 (1H, d, J=8.4 Hz), 8.30 (1H, d, J=8.4 Hz), 8.57 (2H, s).

Example 44

N-Hydroxy 2-(6-{[(6-fluoroquinolin-2-yl)methyl]amino}-3-azabicyclo[3.1.0]hex-3-yl)pyrimidine-5-carboxamide

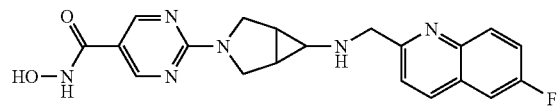

LCMS purity >98%, m/z 395 [M+H]⁺, ¹H NMR (300 MHz, d₆-DMSO) δ: 2.30 (2H, s), 2.75 (1H, s), 3.60 (2H, dm, J=11.7 Hz), 3.88 (2H, d, J=11.7 Hz), 4.69 (2H, br s), 7.66 (1H, d, J=8.4 Hz), 7.75 (1H, td, J=8.7, 3.0 Hz), 7.88 (1H, dd, J=9.3, 2.7 Hz), 8.48 (1H, d, J=8.4 Hz), 8.67 (2H, s), 9.01 (1H, br s), 9.61 (1H, br s), 11.09 (1H, br s).

Preparation of N-Capped Sulfonamides

N-capped sulfonamides were prepared following the methodology described in Scheme 8.

Example 45

N-Hydroxy 2-{6-[methyl(naphthalene-2-sulfonyl)amino]-3-aza-bicyclo[3.1.0]hex-3-yl}pyrimidine-5-carboxamide

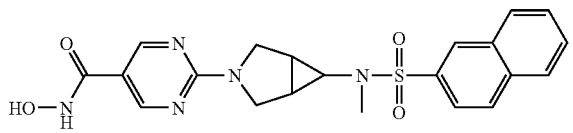

Example 45 was prepared following Method A in Scheme 8.

N-(Tetrahydro-2H-pyran-2-yloxy) 2-{6-[(naphthalene-2-sulfonyl)amino]-3-azabicyclo[3.1.0]hex-3-yl}pyrimidine-5-carboxamide

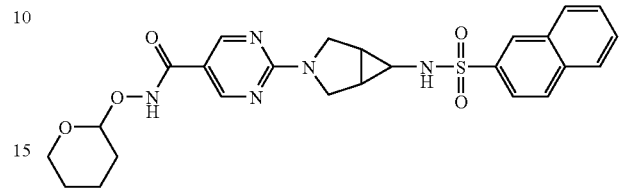

The title compound was prepared as described in example 1.

N-(Tetrahydro-2H-pyran-2-yloxy) 2-{6-[Methyl(naphthalene-2-sulfonyl)amino]-3-azabicyclo[3.1.0]hex-3-yl}pyrimidine-5-carboxamide

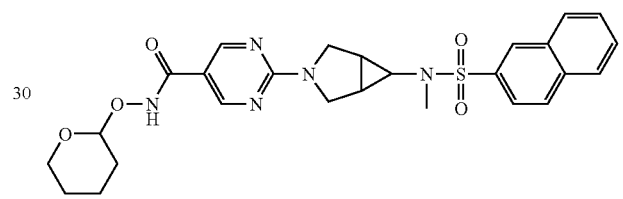

NaH (147 mg, 3.75 mmol) was washed with heptane, and suspended in THF (10 ml). N-(Tetrahydro-2H-pyran-2-yloxy) 2-[6-(naphthalene-2-sulfonylamino)-3-azabicyclo[3.1.0]hex-3-yl]pyrimidine-5-carboxamide (1.113 g, 2.2 mmol) was then added, followed by addition of dimethyl sulfate (0.22 ml, 2.3 mmol). The mixture was stirred for 48 h, then poured into DCM (150 ml). 2.4M ammonium chloride (50 ml) was added. The aqueous layer was further extracted with DCM (150 ml). The combined organic layers were dried (MgSO₄) and concentrated in vacuo to give an orange oil. This was carried forward without any further purification.

N-Hydroxy 2-{6-[methyl(naphthalene-2-sulfonyl)-amino]-3-aza-bicyclo[3.1.0]hex-3-yl}pyrimidine-5-carboxamide—Example 45

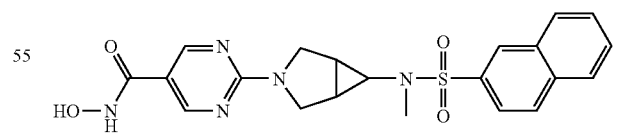

To N-(tetrahydro-2H-pyran-2-yloxy) 2-{6-[methyl(naphthalene-2-sulfonyl)amino]-3-azabicyclo[3.1.0]hex-3-yl}pyrimidine-5-carboxamide was added TFA/DCM/MeOH (5 ml, 1:1:1 mixture). The solution was stirred at r.t. for 2 h. The mixture was then concentrated under reduced pressure, and purified by reverse phase HPLC to yield the title compound (34 mg, 3% yield over 2 steps). LCMS purity >98%, m/z 440 [M−+H]⁺, ¹H NMR (300 MHz, d₆-DMSO) δ: 1.55

(1H, m), 2.25 (2H, m), 2.77 (3H, s), 3.58 (2H, m), 3.78 (2H, d, J=11.8 Hz), 7.66-7.84 (2H, m), 7.82 (1H, dd, J=1.8, 8.6 Hz), 8.06 (1H, m), 8.18 (1H, d, J=8.7 Hz), 8.22-8.28 (1H, m), 8.49-8.52 (1H, m), 8.61 (2H, s), 9.01 (1H, br s), 11.05 (1H, br s).

Example 46

N-Hydroxy 2-{6-[(naphthalene-2-sulfonyl)-(2-pyrrolidin-1-yl-ethyl)amino]-3-azabicyclo[3.1.0]hex-3-yl}pyrimidine-5-carboxamide

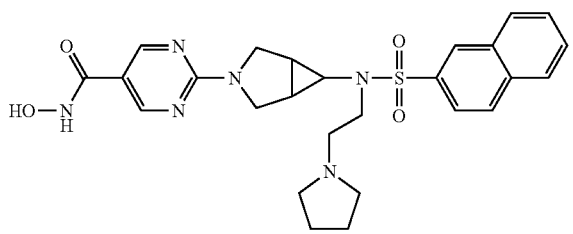

Example 46 was prepared following Method B in Scheme 8.

N-(Tetrahydro-2H-pyran-2-yloxy) 2-{6-[(naphthalene-2-sulfonyl)-(2-pyrrolidin-1-ylethyl)amino]-3-azabicyclo[3.1.0]hex-3-yl}pyrimidine-5-carboxamide

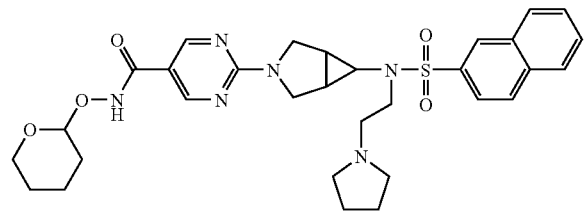

NaH (0.223 g, 5.5 mmol) was washed with heptane (10 ml), then suspended in DMF (5 ml). N-(Tetrahydro-2H-pyran-2-yloxy) 2-{6-[(naphthalene-2-sulfonyl)amino]-3-azabicyclo[3.1.0]hex-3-yl}pyrimidine-5-carboxamide (0.991 g, 1.95 mmol) was added, and the mixture stirred for 5 min. To NaH (0.172 g, 4.3 mmol) in DMF was added 1-(2-chloroethyl)-pyrrolidine hydrochloride (0.724 g, 4.2 mmol). The reaction was swirled gently for 2 min, and then added to the solution of N-(tetrahydro-2H-pyran-2-yloxy) 2-{6-[(naphthalene-2-sulfonyl)amino]-3-azabicyclo[3.1.0]hex-3-yl}pyrimidine-5-carboxamide. The mixture was stirred at r.t. for 5 days, then poured into DCM (150 ml) and quenched with 2.4M ammonium chloride solution (50 ml). The organic layer was separated, and the aqueous was further extracted with DCM (150 ml). The combined organic extracts were dried, concentrated in vacuo to give the title compound (0.234 g, 19%). This was carried forward without further purification.

N-Hydroxy 2-{6-[(naphthalene-2-sulfonyl)-(2-pyrrolidin-1-yl-ethyl)amino]-3-azabicyclo[3.1.0]hex-3-yl}pyrimidine-5-carboxamide—Example 46

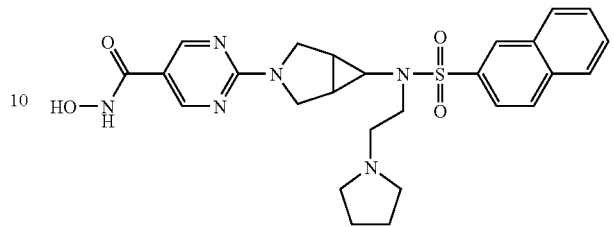

To N-(tetrahydro-2H-pyran-2-yloxy) 2-{6-[(naphthalene-2-sulfonyl)-(2-pyrrolidin-1-ylethyl)amino]-3-azabicyclo[3.1.0]hex-3-yl}pyrimidine-5-carboxamide (0.234 g, 0.38 mmol) was added TFA:DCM:MeOH (6 ml, 1:1:1 mixture). The mixture was stirred for 3 h at r.t. and then concentrated in vacuo. The product was purified by reverse phase HPLC to yield the title compound (60 mg, 30%). LCMS Purity >98%, m/z 523.25 [M+H]$^+$, $^1$H NMR (300 MHz, d$_6$-DMSO) δ: 1.55-1.68 (4H, m), 1.78 (1H, m), 2.25-2.34 (2H, m), 2.35-2.45 (4H, m), 2.55-2.65 (2H, m), 3.25-3.42 (5H, m), 3.54-3.63 (2H, m), 3.73-3.85 (2H, m), 7.65-7.77 (2H, m), 7.86 (1H, d, J=8.5 Hz), 8.06 (1H, d, J=7.3 Hz), 8.17 (1H, d, J=7.3 Hz), 8.24 (1H, d, J=7.3 Hz), 8.55 (1H, s), 8.61 (2H, s), 9.00 (1H, br s), 11.05 (1H, br s).

Example 47

N-Hydroxy 2-{6-[[2-(2-methylimidazol-1-yl)ethyl](naphthalene-2-sulfonyl)amino]-3-azabicyclo[3.1.0]hex-3-yl}pyrimidine-5-carboxamide

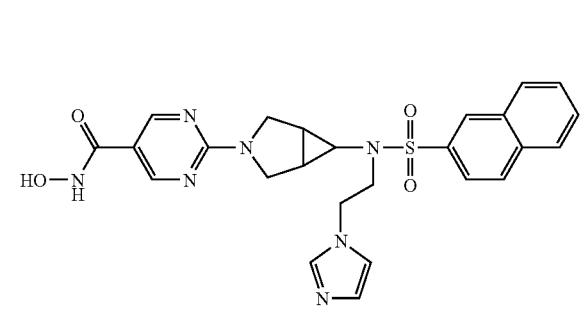

Example 47 was prepared following Method C in Scheme 8.

Ethyl 2-[6-(naphthalene-2-sulfonylamino)-3-azabicyclo[3.1.0]hex-3-yl]-pyrimidine-5-carboxylate

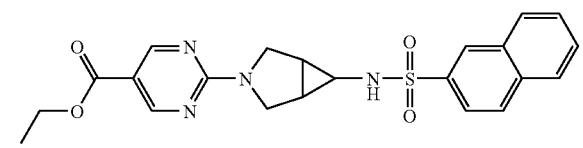

The title compound was prepared as described in example 1.

Ethyl 2-{6-[[2-(2-methylimidazol-1-yl)ethyl](naphthalene-2-sulfonyl)amino]-3-aza-bicyclo[3.1.0]hex-3-yl}pyrimidine-5-carboxylate

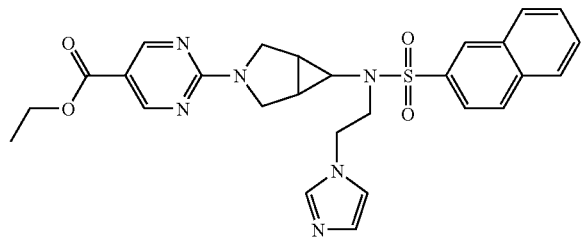

To a solution of ethyl 2-[6-(naphthalene-2-sulfonylamino)-3-aza-bicyclo[3.1.0]hex-3-yl]-pyrimidine-5-carboxylate (0.182 g, 0.47 mmol) in DCM (10 ml) was added triphenylphosphine (0.26 g, 1 mmol) and 1-(2-hydroxyethyl)-2-methylimidazole (0.084 mg, 0.75 mmol). Diisopropylazodicarboxylate (0.167 ml, 0.85 mmol) was then added and the solution stirred overnight. The mixture was loaded directly onto a silica gel column and purified eluting with 2% MeOH/DCM to give the title compound (0.242 g, 90%). $^1$H NMR (300 MHz, CDCl$_3$) δ: 1.36 (3H, t), 1.60-1.80 (3H, m), 2.57 (3H, s), 3.43 (2H, t), 3.48-3.62 (2H, m), 3.70 (2H, d), 4.35 (2H, t), 4.33 (2H, q), 6.90 (1H, d), 6.98 (1H, d), 7.60-7.80 (2H, m) 7.82 (1H, dd), 7.95 (1H, dd), 8.02 (2H, d), 8.43 (1H, s), 8.72 (2H, s).

N-Hydroxy 2-{6-[[2-(2-methylimidazol-1-yl)ethyl](naphthalene-2-sulfonyl)amino]-3-azabicyclo[3.1.0]hex-3-yl}pyrimidine-5-carboxamide—Example 47

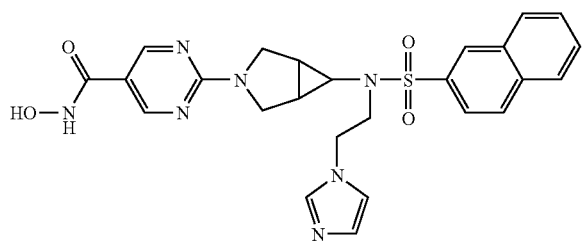

To a solution of ethyl 2-{6-[[2-(2-methylimidazol-1-yl)ethyl](naphthalene-2-sulfonyl)amino]-3-azabicyclo[3.1.0]hex-3-yl}pyrimidine-5-carboxylate (0.211 g, 0.38 mmol) in EtOH (6 ml) in a sealed tube, was added hydroxylamine hydrochloride (0.460 g, 6.6 mmol) and sodium ethoxide (0.358 g, 5.3 mmol). The mixture was heated at 50° C. for 18 h, then water (20 ml) was added, and the product extracted with DCM (3×100 ml) and EtOAc (2×100 ml). The combined organic extracts were dried (MgSO$_4$) and concentrated and the product purified by recrystallisation (MeOH) to give the title compound as a white solid (40 mg, 20%). LCMS Purity >98%, m/z 534 [M+H]$^+$, $^1$H NMR (300 MHz, d$_6$-DMSO) δ: 1.71 (1H, m), 1.82 (2H, m), 2.34 (3H, s), 3.43-3.55 (4H, m), 3.71 (2H, d, J=11.9 Hz), 4.14 (2H, t, J=6.5 Hz), 6.76 (1H, d, J=1.2 Hz), 7.08 (1H, d, J=1.2 Hz), 7.66-7.76 (2H, m), 7.88 (1H, dd, J=1.8, 10.5 Hz), 8.06 (1H, dd, J=2.0, 7.1 Hz), 8.18 (1H, d, J=8.7 Hz), 8.25 (1H, dd, J=2.0, 8.9 Hz), 8.57-8.62 (3H, m), 8.98 (1H, br s), 11.02 (1H, br s).

Example 48

N-Hydroxy 2-(6-{(naphthalene-2-sulfonyl)-[2-(2-oxopyrrolidin-1-yl)ethyl]amino}-3-aza-bicyclo[3.1.0]hex-3-yl)pyrimidine-5-carboxamide

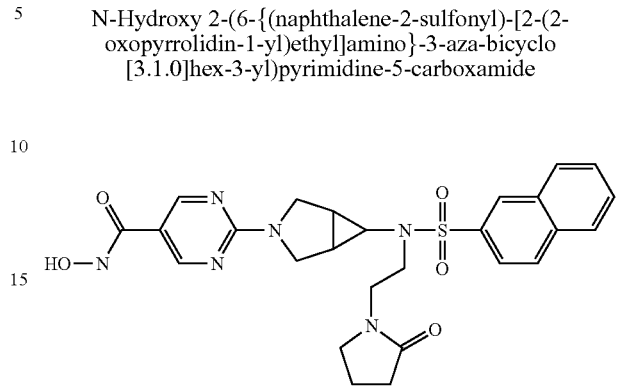

Example 48 was prepared following Method D in Scheme 8.

Ethyl 2-(6-{(naphthalene-2-sulfonyl)-[2-(2-oxopyrrolidin-1-yl)ethyl]amino}-3-aza-bicyclo[3.1.0]hex-3-yl)pyrimidine-5-carboxylate

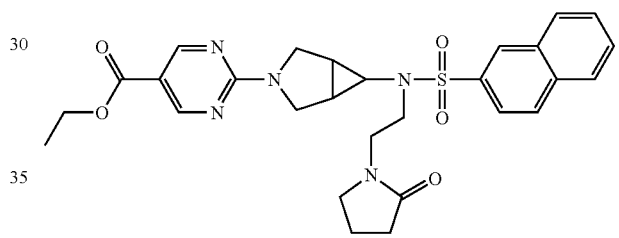

The title compound was prepared as described for method C.

2-(6-{(Naphthalene-2-sulfonyl)-[2-(2oxo-pyrrolidin-1-yl)ethyl]amino}-3-aza-bicyclo[3.1.0]hex-3-yl)-pyrimidine-5-carboxylic acid

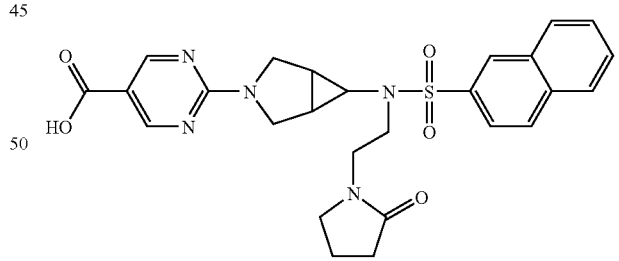

To a solution of ethyl 2-(6-{(naphthalene-2-sulfonyl)-[2-(2-oxopyrrolidin-1-yl)ethyl]amino}-3-azabicyclo[3.1.0]hex-3-yl)pyrimidine-5-carboxylate (0.749 g, 1.4 mmol) in EtOH (8 ml) was added sodium ethoxide (1.08 g, 15.8 mmol) and hydroxylamine hydrochloride (1.30 g, 18.7 mmol). The mixture was stirred at 40° C. for 18 h, then water (20 ml) was added. The product was extracted with DCM (2×100 ml), and the combined organic extracts were dried (MgSO$_4$) and concentrated in vacuo. The expected hydroxamate product was in fact proved not to have formed. The reaction yielded instead the acid. Purification by reverse phase HPLC yielded the title compound (232 mg, 32%). This was used directly in the next step without characterisation.

N-(1-Isobutoxyethoxy) 2-(6-{(naphthalene-2-sulfonyl)-[2-(2-oxopyrrolidin-1-yl)ethyl]-amino}-3-azabicyclo[3.1.0]hex-3-yl)pyrimidine-5-carboxamide

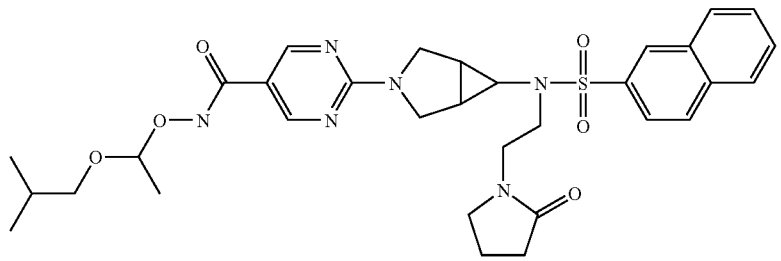

To a solution of 2-(6-{(naphthalene-2-sulfonyl)-[2-(2-oxopyrrolidin-1-yl)ethyl]amino}-3-azabicyclo[3.1.0]hex-3-yl) pyrimidine-5-carboxylic acid (0.170 g, 0.3 mmol) in DMF (2.5 ml) was added HOBt (83 mg, 0.54 mmol) and EDCl (133 mg, 0.7 mmol). Intermediate D (0.4 ml, 3 mmol) and DIPEA (0.4 ml, 2.5 mmol) were then added and the mixture stirred overnight. The DMF was then evaporated, and the crude mixture loaded directly onto a silica gel column. The product was eluted with 2% MeOH/DCM to 4% MeOH/DCM, to give the title compound as an off-white solid (83 mg, 43%). This was used directly in the next step without characterisation.

N-Hydroxy 2-(6-{(naphthalene-2-sulfonyl)-[2-(2-oxopyrrolidin-1-yl)ethyl]amino}-3-aza-bicyclo [3.1.0]hex-3-yl)pyrimidine-5-carboxamide—Example 48

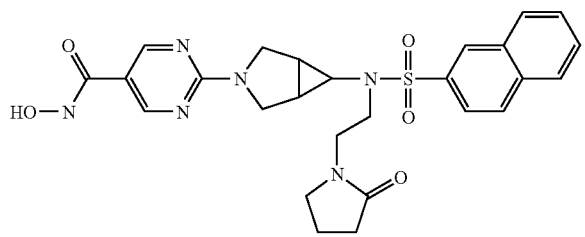

To N-(1-isobutoxyethoxy) 2-(6-{(naphthalene-2-sulfonyl)-[2-(2-oxopyrrolidin-1-yl)ethyl]amino}-3-azabicyclo [3.1.0]hex-3-yl)pyrimidine-5-carboxamide was added TFA:DCM:MeOH (3.5 ml, 1:2:2 mixture). The solution was stirred overnight, and then concentrated in vacuo. The product was purified by reverse phase HPLC to yield the title compound as a white solid (18 mg, 11%). LCMS Purity >98%, m/z 537 [M+H]+, 1H NMR (300 MHz, d6-DMSO) 1.83-1.95 (3H, m), 2.17 (2H, t, J=8.2 Hz), 2.22-2.26 (2H, m), 3.36-3.45 (6H, m), 3.52-3.59 (2H, m), 3.79 (2H, t, J=11.8 Hz), 7.66-7.76 (2H, m), 7.83 (1H, dd, J=1.8, 8.7 Hz), 8.04-8.09 (1H, m), 8.18 (1H, d, J=8.8 Hz), 8.22-8.27 (1H, m), 8.53-8.56 (1H, m), 8.63 (2H, s), 8.99 (1H, br s), 11.03 (1H, br s).

Examples 49 to 55 were prepared according to methods described above:

Example 49

(Method B): N-Hydroxy 2-{6-[(2-hydroxyethyl)(naphthalene-2-sulfonyl)amino]-3-azabicyclo[3.1.0] hex-3-yl}pyrimidine-5-carboxamide

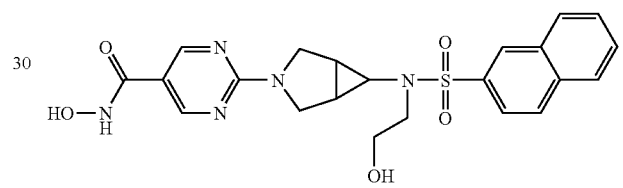

LCMS purity >98%, m/z 470 [M+H]+, 1H NMR (300 MHz, d6-DMSO) δ: 1.75 (1H, m), 2.30 (2H, m), 3.32 (2H, m), 3.50-3.65 (4H, m), 3.78 (2H, d, J=11.9 Hz), 7.64-7.77 (2H, m), 7.85 (1H, dd, J=1.8, 8.6 Hz), 8.05 (1H, dd, J=2.1, 9.2 Hz), 8.16 (1H, d, J=8.8 Hz), 8.28 (1H, dd, J=1.9, 7.1 Hz), 8.53 (1H, m), 8.61 (2H, s), 9.00 (1H, br s), 11.02 (1H, br s).

Example 50

(Method B): N-Hydroxy 2-{6-[(3-dimethylaminopropyl)(naphthalene-2-sulfonyl)amino]-3-azabicyclo [3.1.0]hex-3-yl}pyrimidine-5-carboxamide

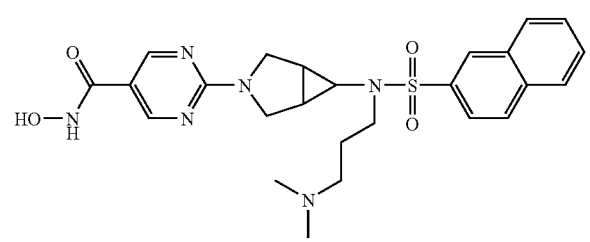

LCMS purity >98%, m/z 511 [M+H]+, 1H NMR (300 MHz, d6-DMSO) δ: 1.55-1.68 (2H, m), 1.76-1.80 (1H, m), 2.05 (6H, s), 2.16 (2H, t, J=6.9 Hz), 2.22-2.29 (2H, m), 3.22-3.33 (2H, m), 3.55-3.64 (2H, m), 3.79 (2H, d, J=11.8 Hz), 7.64-7.75 (2H, m), 7.83 (1H, dd, J=1.8, 8.7 Hz), 8.03-8.08 (1H, m), 8.16 (1H, d, J=8.7 Hz), 8.22-8.25 (1H, m), 8.52-8.54 (1H, m), 8.62 (2H, s), 9.00 (1H, br s), 11.02 (1H, br s).

Example 51

(Method B): N-Hydroxy 2-{6-[2-morpholin-4-yl-ethyl)(naphthalene-2-sulfonyl)amino]-3-azabicyclo[3.1.0]hex-3-yl}pyrimidine-5-carboxamide

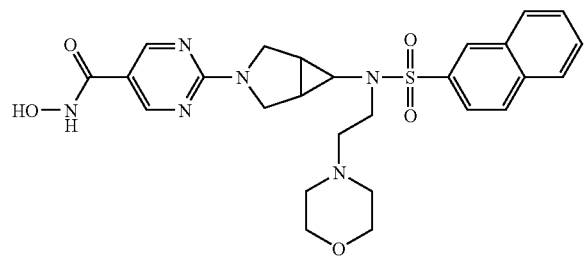

LCMS purity >98%, m/z 539 [M+H]$^+$, $^1$H NMR (300 MHz, d$_6$-DMSO) δ: 1.80-1.83 (1H, m), 2.26-2.39 (6H, m), 2.42-2.50 (2H, m), 3.33-3.42 (2H, m), 3.45-3.60 (6H, m), 3.78 (2H, d, J=11.7 Hz), 7.65-7.75 (2H, m), 7.87 (1H, dd, J=1.8, 8.6 Hz), 8.06 (1H, dd, J=1.9, 7.0 Hz), 8.16 (1H, d, J=8.7 Hz), 8.24 (1H, dd, J=2.1, 6.8 Hz), 8.53-8.56 (1H, m), 8.58 (2H, s).

Example 52

(Method B): N-Hydroxy 2-{6-[(2-dimethylaminoethyl)(naphthalene-2-sulfonyl)-amino]-3-azabicyclo[3.1.0]hex-3-yl}pyrimidine-5-carboxamide

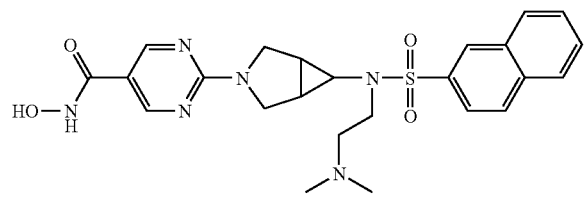

LCMS purity >98%, m/z 496.5 [M+H]$^+$, $^1$H NMR (300 MHz, d$_6$-DMSO) δ: 1.75-1.79 (1H, m), 2.10 (6H, s), 2.25-2.30 (2H, m), 2.36-2.42 (2H, t, J=6.6 Hz), 3.35 (2H, m), 3.52-3.58 (2H, m), 3.76 (2H, d, J=11.6 Hz), 7.65-7.75 (2H, m), 7.86 (1H, dd, J=1.8, 8.7 Hz), 8.06 (1H, dd, J=2.2, 6.5 Hz), 8.18 (1H, d, J=8.7 Hz), 8.24 (1H, dd, J=2.1, 6.8 Hz), 8.52-8.57 (1H, m), 8.56 (2H, s).

Example 53

(Method B): N-Hydroxy 2-{6-[(naphthalene-2-sulfonyl)-(2-piperidin-1-ylethyl)amino]-3-azabicyclo[3.1.0]hex-3-yl}pyrimidine-5-carboxamide

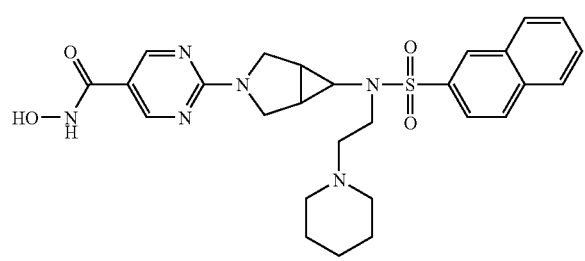

LCMS purity >98%, m/z 537 [M+H]$^+$, $^1$H NMR (300 MHz, d$_6$-DMSO) δ: 1.40-1.51 (2H, m), 1.51-1.60 (4H, m), 1.92 (1H, t, J=1.8 Hz), 2.30-2.35 (2H, m), 2.38-2.50 (4H, m), 2.59 (2H, t, J=7.5 Hz), 3.46 (2H, t, J=7 Hz), 3.59-3.69 (2H, m), 3.92 (2H, d, J=12 Hz), 7.66-7.77 (2H, m), 7.87 (1H, dd, J=1.7, 8.7 Hz), 8.00 (1H, dd, J=2.4, 9.1 Hz), 8.07-8.15 (2H, m), 8.48-8.52 (1H, m), 8.63 (2H, s).

Example 54

(Method C): N-Hydroxy 2-{6-[(naphthalene-2-sulfonyl)-(2-pyridin-2-ylethyl)-amino]-3-azabicyclo[3.1.0]hex-3-yl}pyrimidine-5-carboxamide

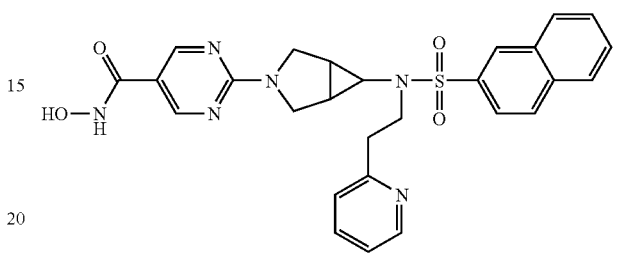

LCMS purity >98%, m/z 531 [M+H]$^+$, $^1$H NMR (300 MHz, d$_6$-DMSO) δ: 2.17-2.23 (1H, m), 2.55-2.63 (2H, m), 3.46 (2H, t, J=7.1 Hz), 3.92-4.0 (2H, m), 4.09 (2H, t, J=7.1 Hz), 4.17 (2H, d, J=11.8 Hz), 7.67-7.80 (2H, m), 8.08-8.17 (2H, m), 8.16-8.29 (2H, m), 8.48 (1H, dd, J=1.4, 8.8 Hz), 8.58 (1H, d, J=8.7 Hz), 8.66 (1H, dd, J=1.4, 7.2 Hz), 8.92-8.99 (2H, m), 9.04 (2H, s), 9.40 (1H, br s), 11.46 (1H, br s).

Example 55

(Method D): N-Hydroxy 2-{6-[[2-(2-oxopyrrolidin-1-yl)ethyl]-(4-trifluoromethoxybenzenesulfonyl)amino]-3-aza-bicyclo[3.1.0]hex-3-yl}pyrimidine-5-carboxamide

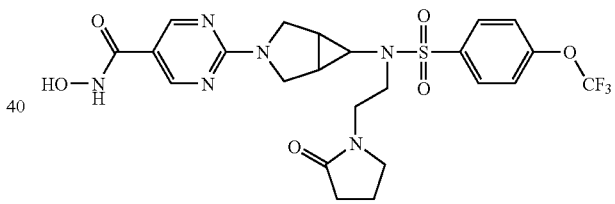

LCMS purity >98%, m/z 571 [M+H]$^+$, $^1$H NMR (300 MHz, d$_6$-DMSO) δ: 1.85-1.97 (3H, m), 2.18 (2H, t, J=8.0 Hz), 2.22-2.24 (2H, m), 3.34-3.44 (6H, m), 3.55-3.62 (2H, m), 3.81 (2H, d, J=11.9 Hz), 7.64 (2H, d, J=8.4 Hz), 7.98 (2H, d, J=8.8 Hz), 8.64 (2H, s), 8.99 (1H, br s), 11.04 (1H, br s).

Example 56

N-Hydroxy 2-{6-[(2-diethylaminoethyl)naphthalen-2-ylmethylamino]-3-aza bicyclo[3.1.0]hex-3-yl}pyrimidine-5-carboxamide

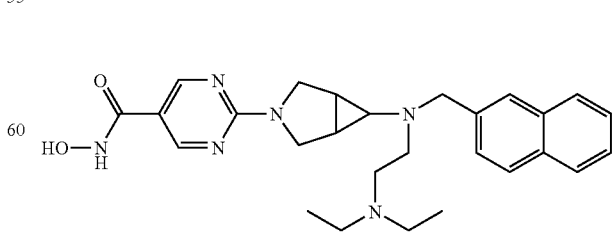

Example 56 was prepared following the methodology described in Scheme 9.

N-(1-Isobutoxyethoxy) 2-{6-[(naphthalen-2-ylm-
ethyl)-amino]-3-azabicyclo[3.1.0]hex-3-
yl}pyrimidine-5-carboxamide

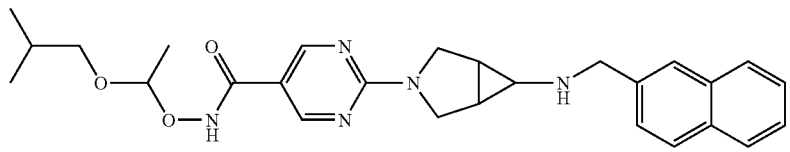

The title compound was prepared as described for example 20.

N-(1-Isobutoxyethoxy) 2-{6-[(2-diethylamino-ethyl)
naphthalen-2-ylmethylamino]-3-azabicyclo[3.1.0]
hex-3-yl}pyrimidine-5-carboxamide

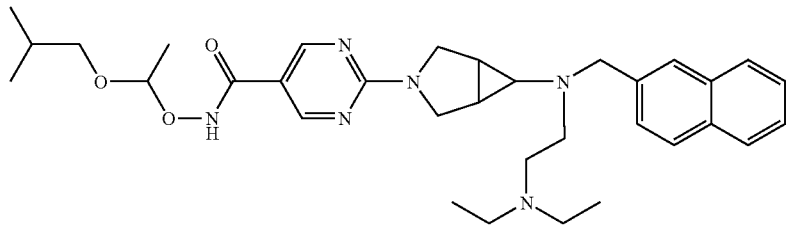

N-(1-Isobutoxyethoxy) 2-{6-[(naphthalen-2-ylmethyl)-amino]-3-azabicyclo[3.1.0]hex-3-yl}-pyrimidine-5-carboxamide (52 mg, 0.11 mmol) was dissolved in anhydrous DMF (2 ml) and cooled over ice. To the solution was added sodium hydride (13 mg, 0.55 mmol-60% dispersion in mineral oil) and the mixture was stirred for 15 min. To the stirring mixture was then added (2-bromoethyl)-N,N-diethylamine (22 mg, 0.12 mmol). After stirring for 30 min, the reaction was quenched by the careful addition of water and stirred for 10 min. The aqueous mixture was extracted with EtOAc (3×20 ml) and the combined organic extracts were washed with brine, dried (MgSO₄) and evaporated to dryness to give the title compound as a white solid (18 mg, 29%). LCMS purity 100%, m/z 575 [M+H]⁺.

N-Hydroxy 2-{6-[(2-diethylaminoethyl)naphthalen-
2-ylmethylamino]-3-aza bicyclo[3.1.0]hex-3-
yl}pyrimidine-5-carboxamide—Example 56

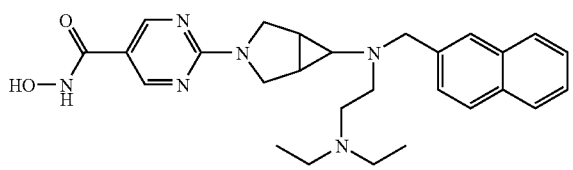

N-(1-Isobutoxyethoxy) 2-{6-[(2-diethylaminoethyl)naphthalen-2-ylmethylamino]-3-azabicyclo[3.1.0]hex-3-yl}pyrimidine-5-carboxamide (18 mg, 0.03 mmol) was dissolved in dry DCM (3 ml) and treated with 4M HCl in dioxane (0.015 ml, 0.06 mmol). A white precipitate immediately formed. This was filtered and washed with DCM to give the title compound as a white solid (8 mg, 57%). LCMS purity 98%, m/z 475 [M+H]⁺, ¹H NMR (300 MHz, CD₃OD) δ: 1.39 (6H, t, J=7.2 Hz), 2.26 (2H, br s), 2.77 (1H, s), 3.37 (4H, m), 3.55 (2H, d, J=10.5 Hz), 3.81 (4H, br s), 3.93 (2H, br d, J=10.5 Hz), 4.71 (2H, br s), 7.61 (2H, m), 7.76 (1H, d, J=8.4 Hz), 7.95-8.04 (3H, m), 8.20 (1H, s), 8.71 (2H, s).

Examples 57 and 58 were prepared in an analogous manner to example 56:

Example 57

N-Hydroxy 2-[6-(bisnaphthalen-2-ylmethylamino)-
3-azabicyclo[3.1.0]hex-3-yl]pyrimidine-5-carboxam-
ide

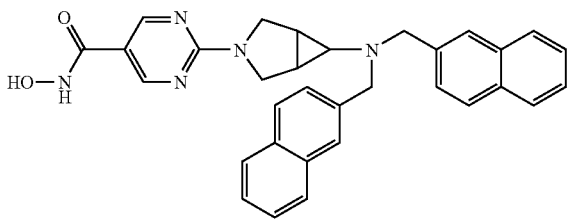

LCMS purity >98%, m/z 516 [M+H]⁺, ¹H NMR (300 MHz, CD₃OD) δ: 1.75 (2H, br s), 2.63 (1H, br s), 3.39 (2H, m), 3.82 (2H, m, J=11.7 Hz) 4.72 (4H, br s), 7.60-7.68 (6H, m), 7.97-8.11 (8H, m), 8.66 (2H, s).

Example 58

N-Hydroxy 2-[6-(naphthalen-2-ylmethylpyridin-3-
ylmethylamino)-3-aza-bicyclo[3.1.0]hex-3-yl]pyri-
midine-5-carboxamide

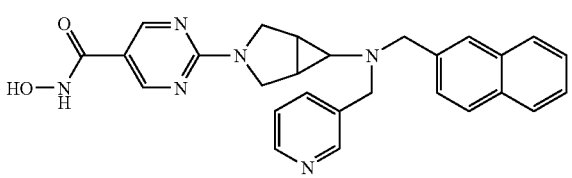

LCMS purity 97%, m/z 467 [M+H]+, 1H NMR (300 MHz, CD3CN/D2O) δ: 1.70 (2H, br s), 2.16 (1H, br s), 3.38 (2H, d, J=11.3 Hz), 3.63 (2H, d, J=11.3 Hz), 4.32 (2H, br s), 4.34 (2H, br s), 7.50 (3H, m), 7.90 (5H, m), 8.45 (1H, d, J=7.6 Hz), 8.55 (2H, s), 8.72 (1H, br s), 8.76 (1H, d, J=5.0 Hz).

Example 59

N-Hydroxy 2-{6-[(3-diethylaminopropionyl)naphthalen-2-ylmethylamino]-3-azabicyclo[3.1.0]hex-3-yl}-pyrimidine-5-carboxamide

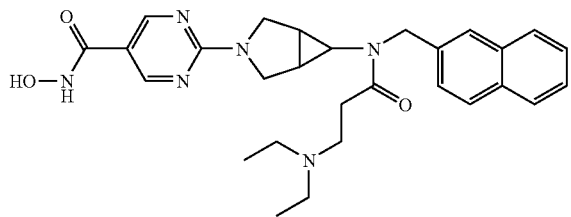

Example 59 was prepared following the methodology described in Scheme 10.

N-(1-Isobutoxyethoxy) 2-{6-[(naphthalen-2-ylmethyl)-amino]-3-azabicyclo[3.1.0]hex-3-yl}pyrimidine-5-carboxamide

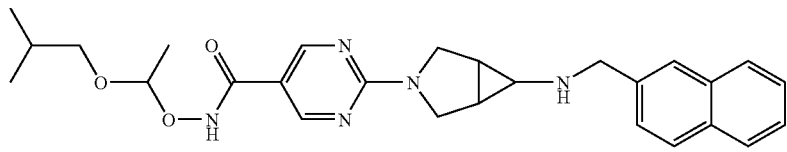

The title compound was prepared as described for example 20.

N-(1-Isobutoxyethoxy) 2-{6-[(3-diethylaminopropionyl)naphthalen-2-ylmethyl-amino]-3-aza-bicyclo[3.1.0]hex-3-yl}pyrimidine-5-carboxamide

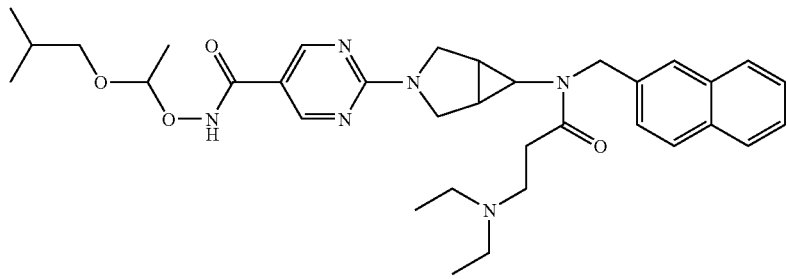

3-N,N-Diethylaminopropionic acid (73 mg, 0.5 mmol) was suspended in oxalyl chloride (1 ml, 11.2 mmol) and DMF (1 drop) was added. The resultant mixture was stirred at r.t. overnight. The reaction mixture was then evaporated under reduced pressure and azeotroped with DCM. The residue was dissolved in DCM (1 ml) and added to an ice-cooled solution of N-(1-isobutoxyethoxy) 2-{6-[(naphthalen-2-ylmethyl)amino]-3-azabicyclo[3.1.0]hex-3-yl}-pyrimidine-5-carboxamide (100 mg, 0.21 mmol) in DCM (3 ml) and triethylamine (0.3 ml, 2.15 mmol). After stirring at 0° C. for 20 min, the resulting mixture was stirred at r.t. overnight. The reaction mixture was partitioned between DCM (5 ml) and water (5 ml). The aqueous layer was extracted twice more with DCM (2×5 ml) and the combined organics washed with brine (2×5 ml), dried (MgSO4) and evaporated to dryness. The title compound was obtained as a white solid (199 mg, quant.). m/z 603 [M+H]+.

N-Hydroxy 2-{6-[(3-diethylaminopropionyl)naphthalen-2-ylmethylamino]-3-azabicyclo[3.1.0]hex-3-yl}pyrimidine-5-carboxamide—Example 59

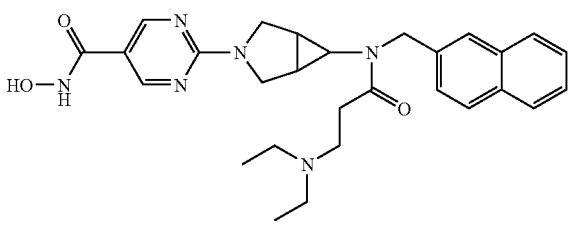

N-(1-Isobutoxyethoxy) 2-{6-[(3-diethylaminopropionyl)naphthalen-2-ylmethyl-amino]-3-azabicyclo[3.1.0]hex-3-yl}pyrimidine-5-carboxamide (199 mg, 0.33 mmol) was dissolved in DCM (3 ml) and treated with a solution of 4M HCl in dioxane (0.5 ml, 2 mmol). The resulting precipitate was filtered and dried to give the title compound as a white solid (94 mg, 57%). LCMS purity 98%, m/z 475 [M+H]+, 1H NMR (300 MHz, CD3OD) δ: 1.39 (6H, t, J=7.2 Hz), 2.26 (2H, br s), 2.77 (1H, s), 3.37 (4H, m), 3.55 (2H, d, J=10.5 Hz), 3.81 (4H, br s), 3.93 (2H, d, J=10.5 Hz), 4.71 (2H, br s), 7.61 (2H, m), 7.76 (1H, d, J=8.4 Hz), 7.95-8.04 (3H, m), 8.20 (1H, s), 8.71 (2H, s).

Examples 60 and 61 were prepared in an analogous manner to example 59:

Example 60

N-Hydroxy 2-[6-(acetylnaphthalen-2-ylmethylamino)-3-azabicyclo[3.1.0]hex-3-yl]pyrimidine-5-carboxamide

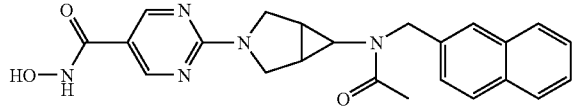

LCMS purity 98%, m/z 418 [M+H]+, $^1$H NMR (300 MHz, CD$_3$OD) δ: 2.32 (2H, br s), 2.37 (3H, s), 2.43 (1H, br s), 3.64 (2H, d, J=11.6 Hz), 3.84 (2H, d, J=11.6 Hz), 7.39 (1H, dd, J=8.5, 1.3 Hz), 7.48 (2H, m), 7.75 (1H, s), 7.85 (3H, m), 8.60 (2H, s).

Example 61

N-Hydroxy 2-{6-[naphthalen-2-ylmethyl-(3-pyridin-3-yl-propionyl)amino]-3-aza-bicyclo[3.1.0]hex-3-yl}pyrimidine-5-carboxamide

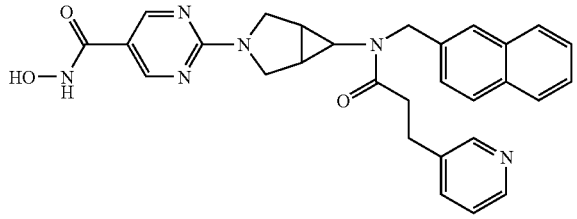

LCMS purity 98%, m/z 509 [M+H]+, $^1$H NMR (300 MHz, CD$_3$OD) δ: 2.32 (2H, br s), 2.43 (1H, br s), 3.24 (4H, m), 3.64 (2H, d, J=11.7 Hz), 3.87 (2H, d, J=11.7 Hz), 4.80 (2H, s), 7.28 (1H, d, J=8.5 Hz), 7.48 (2H, m), 7.67 (1H, br s), 7.82 (3H, m), 7.98 (1H, m), 8.60-8.69 (4H, m), 8.85 (1H, br s).

Example 62

N-Hydroxy 2-(6-morpholin-4-yl-3-azabicyclo[3.1.0]hex-3-yl)pyrimidine-5-carboxamide

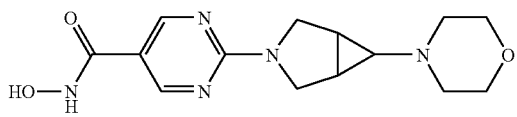

Example 62 was prepared following the methodology described in Scheme 11.

tert-Butyl 6-morpholin-4-yl-3-azabicyclo[3.1.0]hexane-3-carboxylate

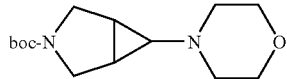

A solution of intermediate B (200 mg, 1.01 mmol) in anhydrous THF (5 ml) was added to a stirring solution of 1-bromo-2-(2-bromoethoxy)ethane (234 mg, 1.01 mmol) in anhydrous THF (15 ml) and triethylamine (323 ml, 2.32 mmol). The mixture was heated to reflux for 48 h. The reaction mixture was cooled to r.t., diluted with water (10 ml) and extracted with EtOAc (3×5 ml). The combined organic extracts were washed with brine (2×5 ml), then dried (MgSO$_4$) and evaporated to dryness. The residue was purified by flash chromatography eluting with 100% DCM to 6% MeOH/DCM to give the title compound as a clear oil (24 mg, 9%). m/z 269 [M+H]+, $^1$H NMR (300 MHz, CDCl$_3$) δ: 1.43 (9H, s), 1.58 (2H, br s), 2.58 (4H, m), 3.33-3.56 (5H, m), 3.65 (4H, m).

Ethyl 2-(6-morpholin-4-yl-3-azabicyclo[3.1.0]hex-3-yl)pyrimidine-5-carboxylate

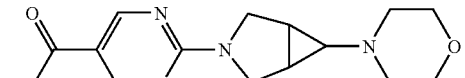

tert-Butyl 6-morpholin-4-yl-3-azabicyclo[3.1.0]hexane-3-carboxylate (24 mg, 0.07 mmol) was dissolved in 4M HCl in dioxane (1 ml) and stirred at r.t. for 1 h. This was then evaporated to dryness under reduced pressure and azeotroped with DCM (3×) before suspending in anhydrous MeCN (2 ml). The suspension was stirred with potassium carbonate (96 mg, 0.7 mmol) and anhydrous DMF was added to aid dissolution of the substrate. Finally intermediate A (16 mg, 0.07 mmol) was added and the reaction mixture was stirred at r.t. for 18 h. The reaction mixture was purified by flash chromatography eluting with 100% DCM to 6% MeOH/DCM to give the title compound as a white solid (16 mg, 57%). LCMS purity 100%, m/z 319 [M+H]+.

2-(6-Morpholin-4-yl-3-azabicyclo[3.1.0]hex-3-yl)pyrimidine-5-carboxylic acid

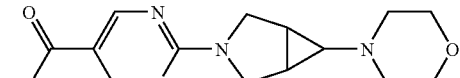

Ethyl 2-(6-morpholin-4-yl-3-azabicyclo[3.1.0]hex-3-yl)pyrimidine-5-carboxylate (16 mg, 0.05 mmol) was dissolved in THF (1 ml) and a solution of 6M NaOH in water (0.5 ml) was added. The reaction was stirred at r.t. for 18 h. More 6M NaOH (0.5 ml) was added and the reaction stirred for a further 24 h. The reaction mixture was evaporated to leave only the aqueous portion, which was acidified to pH~1 using 10% aq. HCl, then evaporated to dryness and used in the next step without further purification. LCMS purity 100%, m/z 291 [M+H]$^+$.

N-(1-Isobutoxyethoxy) 2-(6-morpholin-4-yl-3-azabicyclo[3.1.0]hex-3-yl)pyrimidine-5-carboxamide

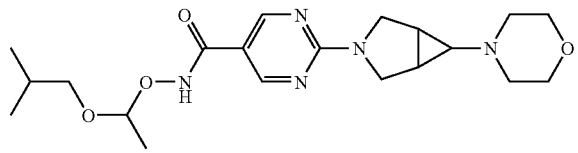

The crude 2-(6-Morpholin-4-yl-3-azabicyclo[3.1.0]hex-3-yl)pyrimidine-5-carboxylic acid was suspended in anhydrous DMF (3 ml) and EDCl (19 mg, 0.1 mmol) and HOBt (11 mg, 0.075 mmol) were added. After stirring for ~5 minutes, triethylamine (35 μl, 0.25 mmol) and intermediate D (58 μl, 0.5 mmol) were added and the resultant mixture was stirred at r.t. for 18 h. The reaction mixture was diluted with water and extracted with EtOAc (3×10 ml) and DCM (2×10 ml). The combined organics were dried (MgSO$_4$) and evaporated onto silica. The residue was purified by flash chromatography eluting with 100% DCM to 15% MeOH/DCM to give the title compound as an off-white solid (10 mg, 51%). LCMS purity 100%, m/z 406 [M+H]$^+$.

N-Hydroxy 2-(6-morpholin-4-yl-3-azabicyclo[3.1.0]hex-3-yl)pyrimidine-5-carboxamide—Example 62

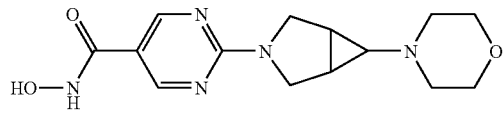

N-(1-Isobutoxyethoxy) 2-(6-morpholin-4-yl-3-aza-bicyclo[3.1.0]hex-3-yl)pyrimidine-5-carboxamide (10 mg, 0.02 mmol) was dissolved in DCM (2 ml) and treated with 4M HCl in dioxane (0.4 ml, 0.1 mmol). The resultant mixture was stirred at r.t. for 30 min, then evaporated under reduced pressure and azeotroped with MeOH (3×5 ml) to give the title compound as a white solid (2.3 mg, 40%). LCMS purity 90%, m/z 306 [M+H]$^+$, $^1$H NMR (300 MHz, CD$_3$OD) δ: 2.49 (2H, br s), 2.85 (1H, br s), 3.55-3.87 (8H, m), 4.10 (4H, m), 8.72 (2H, s).

Examples 63 to 66 were prepared in an analogous manner to example 62:

Example 63

N-Hydroxy 2-(6-piperidin-1-yl-3-azabicyclo[3.1.0]hex-3-yl)pyrimidine-5-carboxamide

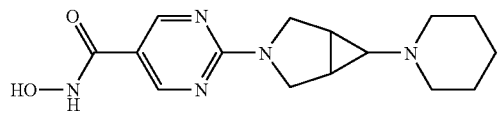

LCMS purity 87%, m/z 304 [M+H]$^+$, $^1$H NMR (300 MHz, d$_6$-DMSO) δ: 1.36 (1H, m), 1.74 (5H, m), 2.42 (2H, br s), 2.71 (1H, m), 2.99 (2H, m), 3.54 (4H, m), 3.91 (2H, d, J=11.5 Hz), 8.68 (2H, s), 10.14 (1H, br s), 11.11 (1H, br s).

Example 64

N-Hydroxy 2-[6-(1,3-dihydro-2H-isoindol-2-yl)-3-azabicyclo[3.1.0]hex-3-yl]pyrimidine-5-carboxamide

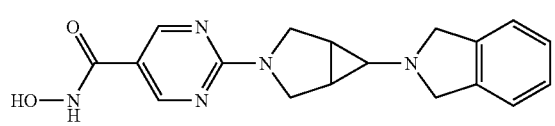

LCMS purity 100%, m/z 338 [M+H]$^+$, $^1$H NMR (300 MHz, d$_6$-DMSO) δ: 3.61 (2H, d, J=11.6 Hz), 3.97 (2H, d, J=11.6 Hz), 4.75 (4H, m), 7.39 (4H, m), 8.68 (2H, s), 11.11 (1H, br s), 11.82 (1H, br s), further 3H under DMSO and water peaks.

Example 65

N-Hydroxy 2-[6-(3-oxo-3,4-dihydroisoquinolin-2(1H)-yl)-3-aza bicyclo[3.1.0]hex-3-yl]pyrimidine-5-carboxamide

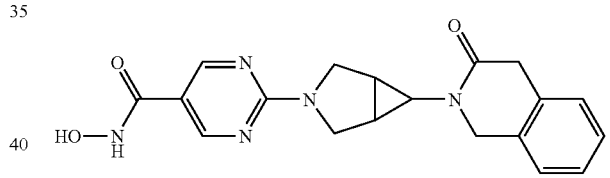

LCMS purity 100%, m/z 366 [M+H]$^+$, $^1$H NMR (300 MHz, CD$_3$OD) δ: 2.17 (2H, br s), 2.51 (1H, t, J=2.1 Hz), 3.62 (2H, s), 3.71 (2H, d, J=10.1 Hz), 4.10 (2H, d, J=10.1 Hz), 4.60 (2H, s), 7.17-7.33 (4H, m), 8.68 (2H, s).

Example 66

N-Hydroxy 2-[6-(3,4-dihydroisoquinolin-2(1H)-yl)-3-azabicyclo[3.1.0]hex-3-yl]pyrimidine-5-carboxamide

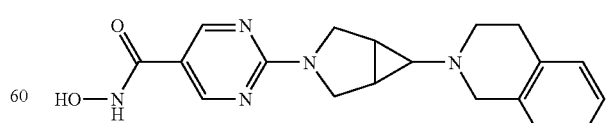

LCMS purity 95%, m/z 352 [M+H]$^+$, $^1$H NMR (300 MHz, CD$_3$OD) δ: 2.54 (2H, br s), 2.88 (1H, br s), 3.25 (2H, m), 3.75 (4H, m), 4.12 (2H, d, J=11.8 Hz), 4.62 (2H, br s), 7.31 (4H, m), 8.70 (2H, s).

Example 67

N-Hydroxy 2-[6-(quinolin-2-ylamino)-3-azabicyclo[3.1.0]hex-3-yl]pyrimidine-5-carboxamide

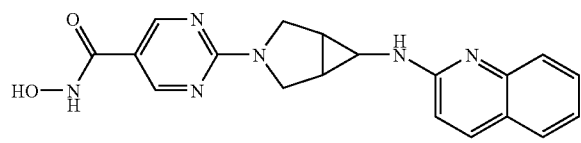

Example 67 was prepared following the methodology described in Scheme 12.

tert-Butyl 6-(quinolin-2-ylamino)-3-azabicyclo[3.1.0]hexane-3-carboxylate

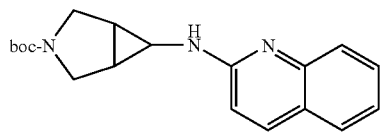

Intermediate B (200 mg, 1.01 mmol) was combined with 2-chloroquiniline (328 mg, 2.02 mmol) and the two solids melted at 100° C. for 16 h. The reaction was then cooled and the residue purified by column chromatography eluting with 0 to 3% MeOH in DCM to give the title compound as a brown oil (320 mg, 97%). LCMS purity 94%, m/z 326 [M+H]$^+$.

(3-Azabicyclo[3.1.0]hex-6-yl)quinolin-2-yl-amine

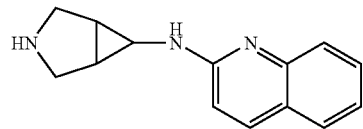

tert-Butyl 6-(quinolin-2-ylamino)-3-azabicyclo[3.1.0]hexane-3-carboxylate (320 mg, 0.98 mmol) was stirred in 4M HCl in dioxane (2 ml) at r.t. under N$_2$ for 15 min. The solvent was then removed in vacuo and the residue dried under high-vacuum and used in the next step without further purification. LCMS purity 91%, m/z 226 [M+H]$^+$.

Ethyl 2-[6-(quinolin-2-ylamino)-3-azabicyclo[3.1.0]hex-3-yl]pyrimidine-5-carboxylate

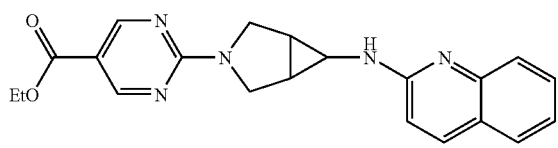

(3-Azabicyclo[3.1.0]hex-6-yl)quinolin-2-yl-amine (0.98 mmol), was stirred in MeCN (10 ml) and DMF (10 ml) at r.t. under N$_2$. K$_2$CO$_3$ (1.35 g, 9.8 mmol) was then added and the mixture stirred for 15 min. Intermediate A (227 mg, 0.98 mmol) was then added to the reaction mixture and stirring continued for 30 min. The reaction was then diluted with H$_2$O (100 ml) and extracted twice with EtOAc (2×100 ml). The combined organic extracts were dried (MgSO$_4$) and solvent removed in vacuo to give the title compound as a light brown solid which was used in the next step without further purification. LCMS purity 82%, m/z 376 [M+H]$^+$.

2-[6-(Quinolin-2-ylamino)-3-azabicyclo[3.1.0]hex-3-yl]pyrimidine-5-carboxylic acid

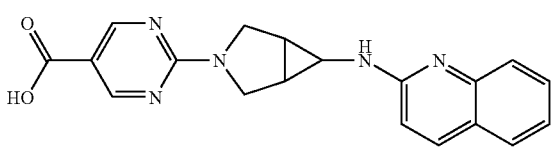

Ethyl 2-[6-(quinolin-2-ylamino)-3-azabicyclo[3.1.0]hex-3-yl]pyrimidine-5-carboxylate (0.98 mmol) was stirred in THF (10 ml) and H$_2$O (10 ml) at r.t. for 64 h. The reaction was then acidified to pH~3 and the solvent removed in vacuo to give a brown solid. The solid was collected and washed with a little H$_2$O to give the title compound as a brown solid (103 mg, 30% over 3 steps). LCMS purity 90%, m/z 348 [M+H]$^+$.

N-(1-Isobutoxyethoxy) 2-[6-(quinolin-2-ylamino)-3-azabicyclo[3.1.0]hex-3-yl]-pyrimidine-5-carboxyamide

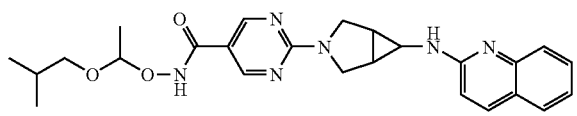

2-[6-(Quinolin-2-ylamino)-3-azabicyclo[3.1.0]hex-3-yl]pyrimidine-5-carboxylic acid (103 mg, 0.29 mmol) was stirred in DMF (10 ml) at r.t. under N$_2$. EDCl (67 mg, 0.35 mmol) and HOBt (47 mg, 0.35 mmol) were added and the mixture stirred for 10 min. Intermediate D (200 µl, 1.45 mmol) and triethylamine (202 µl, 1.45 mmol) were then added and the reaction stirred for 16 h. The reaction was then diluted with H$_2$O (100 ml) and extracted with DCM (2×100 ml). The combined organic extracts were dried (MgSO$_4$) and solvent removed in vacuo. The residue was purified by column chromatography eluting with 0 to 10% MeOH in DCM to give the title compound as a white solid (48 mg, 36%). LCMS purity 85%, m/z 463 [M+H]$^+$.

N-Hydroxy 2-[6-(quinolin-2-ylamino)-3-azabicyclo[3.1.0]hex-3-yl]pyrimidine-5-carboxamide—Example 67

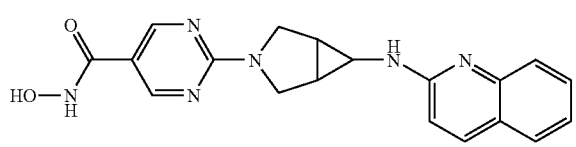

N-(1-Isobutoxyethoxy) 2-[6-(quinolin-2-ylamino)-3-azabicyclo[3.1.0]hex-3-yl]-pyrimidine-5-carboxamide (48 mg, 0.1 mmol) was stirred in DCM (2 ml) at r.t. under $N_2$. 4M HCl in dioxane (20 μl, 0.2 mmol) was added, immediately causing a solid to precipitate. The reaction was stirred for 10 min and then solvent removed in vacuo. DCM (~10 ml) was added to the residue and the solid filtered and dried to give the title compound as a white solid (21 mg, 58%). LCMS purity 98%, m/z 363 [M+H]$^+$, (300 MHz, $d_6$-DMSO) δ: 2.19 (2H, br s), 2.99 (1H, m), 3.63 (2H, dm, J=11.7 Hz), 4.27 (2H, d, J=11.7 Hz), 7.15 (1H, d, J=8.8 Hz), 7.53 (1H, t, J=7.6 Hz), 7.81 (1H, t, J=7.6 Hz), 7.94 (1H, d, J=8.0 Hz), 8.09 (1H, d, J=8.0 Hz), 8.33 (1H, d, J=8.8 Hz), 8.28 (2H, s), 10.24 (1H, br s), 11.12 (1H, br s), 12.96 (1H, br s).

Example 68 was prepared in an analogous manner to example 67:

Example 68

N-Hydroxy 2-[6-(isoquinolin-1-ylamino)-3-azabicyclo[3.1.0]hex-3-yl]pyrimidine-5-carboxamide

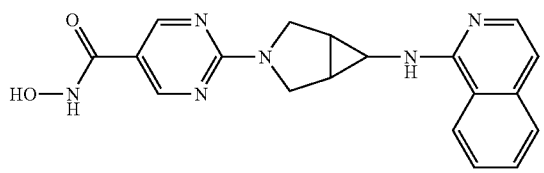

LCMS purity 99%, m/z 363 [M+H]$^+$, $^1$H NMR (300 MHz, $d_6$-DMSO) δ: 2.35 (2H, br s), 2.84 (1H, m), 3.65 (2H, dm, J=11.7 Hz), 4.33 (2H, d, J=11.7 Hz), 7.34 (1H, d, J=6.9 Hz), 7.74-7.82 (2H, m), 7.95-8.02 (2H, m), 8.73 (2H, s), 8.80 (1H, d, J=8.4 Hz), 10.12 (1H, br s), 11.15 (1H, br s), 12.81 (1H, br s).

Example 69

N-Hydroxy 2-{[3-(2-naphthylsulfonyl)-3-azabicyclo[3.1.0]hex-6-yl]amino}pyrimidine-5-carboxamide

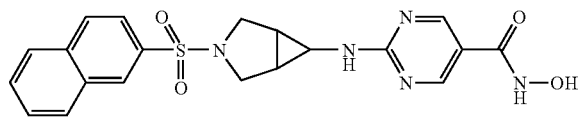

Example 69 was prepared following the methodology described in Scheme 13.

tert-Butyl 6-{[5-(ethoxycarbonyl)pyrimidin-2-yl]amino}-3-azabicyclo[3.1.0]hexane-3-carboxylate

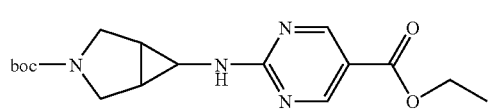

To a solution of intermediate B (150 mg, 0.76 mmol) in MeCN (0.7 ml) was added $K_2CO_3$. To this, a solution of intermediate A (174 mg, 0.76 mmol) in MeCN (0.7 ml) was added dropwise resulting in a white suspension. Stirring at r.t. was continued for 30 min after which the white suspension turned pale yellow. The reaction mixture was evaporated, are dissolved in EtOAc (10 ml) and washed with water (5 ml). The EtOAc layer was dried ($Na_2SO_4$) filtered and concentrated to dryness. Purification by flash chromatography (100% DCM to 2% MeOH/DCM) gave the title compound as an off-white solid (0.15 g, 57%). LCMS purity 89%, m/z 349 [M+H]$^+$.

Ethyl 2-(3-azabicyclo[3.1.0]hex-6-ylamino)pyrimidine-5-carboxylate trifluoroacetate

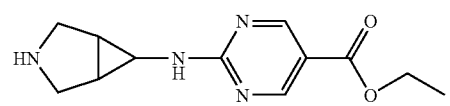

A solution of tert-butyl 6-{[5-(ethoxycarbonyl)pyrimidin-2-yl]amino}-3-azabicyclo[3.1.0]hexane-3-carboxylate (0.15 g) was allowed to stand in 20% TFA/DCM (10 ml) at r.t. for 1 h. The reaction mixture was concentrated to dryness giving the title product as the TFA salt (0.17 g). LCMS purity 76%, m/z 249 [M+H]$^+$. The product was used in the next stage without purification.

Ethyl 2-{[3-(napthylsulfonyl)-3-azabicyclo[3.1.0]hex-6-yl]amino}pyrimidine-5-carboxylate

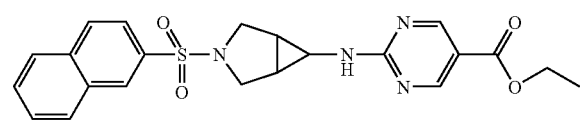

To a solution of ethyl 2-(3-azabicyclo[3.1.0]hex-6-ylamino)pyrimidine-5-carboxylate (107 mg, 0.4 mmol) in dry DCM (5 ml) was added $Et_3N$ (0.18 ml, 1.2 mmol). A solution of naphthalene-2-sulfonyl chloride (98 mg, 0.4 mmol) in DCM (5 ml) was added slowly under $N_2$. The mixture was stirred at r.t. for 1 h, and was then diluted with DCM (30 ml) and washed with sat. aq. $NaHCO_3$ (2×20 ml) followed by water (10 ml) and brine (10 ml). The DCM was dried ($Na_2SO_4$), filtered and evaporated to dryness to give a pale yellow solid. Purification by flash column (DCM to 2% MeOH/DCM) afforded the title compound as a white solid (128 mg, 73%—over two steps). LCMS purity 100%, m/z 439 [M+H]$^+$.

2-{[3-(2-Naphthylsulfonyl)-3-azabicyclo[3.1.0]hex-6-yl]amino}pyrimidine-5-carboxylic acid

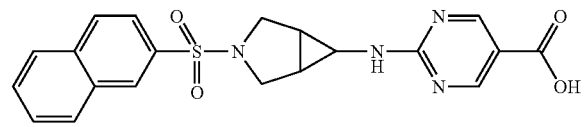

To a solution of ethyl 2-{[3-(napthylsulfonyl)-3-azabicyclo[3.1.0]hex-6-yl]amino}pyrimidine-5-carboxylate (127 mg, 0.29 mmol) in THF (5 ml) and MeOH (1 ml) was added 1M NaOH (4 ml). The solution was stirred at r.t. for 2.5 h. The reaction mixture was acidified to pH~5/6 with 2M HCl to give a white precipitate which was collected by filtration, washed with water and dried in vacuo to give the title compound as a white solid (105 mg, 88%). LC-MS purity 100%, m/z 411 [M+H]+.

N-(Tetrahydro-2H-pyran-2-yloxy) 2-{[3-(2-napthyl-sulphonyl)-3-azabicyclo[3.1.0]hex-6-yl]amino}pyrimidine-5-carboxamide

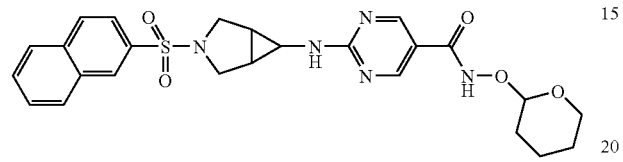

To a solution of 2-{[3-(2-naphthylsulfonyl)-3-azabicyclo[3.1.0]hex-6-yl]amino}pyrimidine-5-carboxylic acid (105 mg, 0.26 mmol) in DCM (5 ml) and THF (5 ml) was added EDCl (59 mg, 0.3 mmol). Et₃N (0.08 ml, 0.8 mmol) was added followed by HOBt (42 mg, 0.3 mmol) and O-(tetrahydro-pyran-2-yl)-hydroxylamine (36 mg, 0.3 mmol). The suspension was stirred at r.t. for 3 days. Further EDCl (14 mg), Et₃N (0.02 ml), HOBt (11 mg), and O-(tetrahydro-pyran-2-yl)-hydroxylamine (9 mg) were added and stirring at r.t. continued for a further 3 days. The reaction mixture was evaporated to dryness, re-dissolved in EtOAc (20 ml) and washed with sat. aq. NaHCO₃ (10 ml) and water (10 ml). The EtOAc layer was dried (Na₂SO₄), filtered and concentrated to dryness to afford the title compound as a white solid (110 mg, 83%). LCMS purity 90%, m/z 511 [M+H]+.

N-Hydroxy 2-{[3-(2-naphthylsulfonyl)-3-azabicyclo[3.1.0]hex-6-yl]amino}pyrimidine-5-carboxamide—Example 69

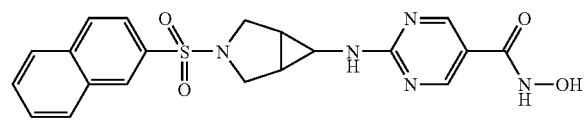

To a solution of N-(tetrahydro-2H-pyran-2-yloxy) 2-{[3-(2-napthylsulphonyl)-3-azabicyclo[3.1.0]hex-6-yl]amino}pyrimidine-5-carboxamide (110 mg, 0.21 mmol) in MeOH (15 ml) and DCM (15 ml), was added TFA (1.5 ml) at r.t. The mixture was stirred for 8 h before removal of solvent in vacuo. Excess TFA was removed by re-dissolving in DCM (5 ml×2) and concentration to dryness under reduced pressure. Purification by preparative HPLC gave the title compound as a white solid (25.1 mg, 21%). LCMS purity 100%, m/z 426 [M+H]+, ¹H NMR (400 MHz, d₆-DMSO) δ: 1.15 (2H, s), 2.55 (1H, s), 3.20 (2H, d), 3.65 (2H, d), 7.65 (2H, m), 7.75 (1H, d), 7.90 (1H, m), 8.15-8.30 (3H, m), 8.50 (1H, s), 8.65 (2H, s).

Example 70

N-Hydroxy 2-{3-[(2-naphthylsulfonyl)amino]azetidin-1-yl}pyrimidine-5-carboxamide

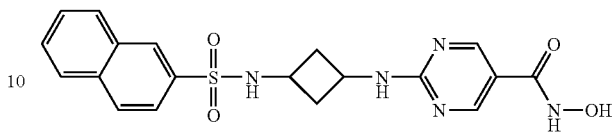

Example 70 was prepared following the methodology described in Scheme 14.

Ethyl 2-{3-[(tert-butoxycarbonyl)amino]azetidin-1-yl}pyrimidine-5-carboxylate

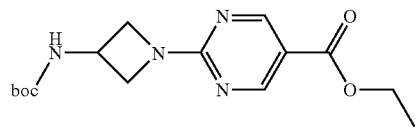

Intermediate A (267 mg, 1.16 mmol) was added to tert-butyl azetidin-3-yl-carbamic acid (200 mg, 1.16 mmol) and K₂CO₃ (481 mg, 3.48 mmol) in MeCN (10 ml) at r.t. under N₂. The resultant white suspension was stirred at r.t. for 4 h. The reaction mixture was diluted with water (50 ml) and extracted into EtOAc (3×50 ml). The combined organic phases were washed with water (2×50 ml), brine (50 ml), dried (MgSO₄) and concentrated in vacuo to give the title compound as a white solid (323 mg, 86%). LCMS purity 100%, m/z 323 [M+H]+, ¹H NMR (400 MHz, CDCl₃) δ: 1.37 (3H, t), 1.46 (9H, s), 4.04 (2H, m), 4.34 (2H, q), 4.53 (2H, t), 4.64 (1H, br s), 5.02 (1H, br s), 8.84 (2H, s).

Ethyl 2-(3-aminoazetidin-1-yl)pyrimidine-5-carboxylate hydrochloride

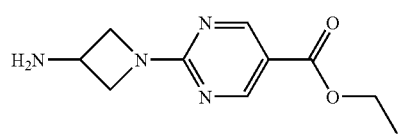

4M HCl in dioxane (15 ml) was added to ethyl 2-{3-[(tert-butoxycarbonyl)amino]azetidin-1-yl}pyrimidine-5-carboxylate (323 mg, 1 mmol) and the reaction stirred at r.t. for 30 min. The suspension was concentrated in vacuo to give the title compound as a white solid (323 mg, quant.). LCMS purity 78%, m/z 223 [M+H]+.

Ethyl 2-{3-[2-naphthylsulfonyl)amino]azetidin-1-yl}pyrimidine-5-carboxylate

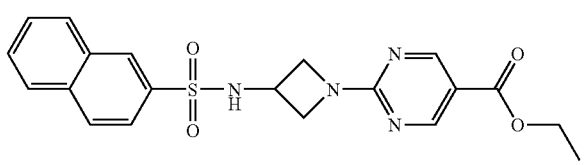

Et₃N (0.51 ml, 3.68 mmol) was added to a stirred suspension of ethyl 2-(3-aminoazetidin-1-yl)pyrimidine-5-carboxylate hydrochloride (317 mg, 1.23 mmol) in DCM (15 ml) at r.t. under N₂. Naphthalenesulfonyl chloride (306 mg, 1.35 mmol) was added in one portion at r.t. and the solution stirred at r.t. overnight. The reaction mixture was diluted with DCM (50 ml) and washed with sat. NaHCO₃ (2×50 ml), water (50 ml), brine (50 ml), dried (MgSO₄) and concentrated in vacuo to give a cream solid. Purification by flash column chromatography (2% MeOH/DCM) afforded the title compound as a white solid (354 mg, 70%). LCMS purity 97%, m/z 413 [M+H]⁺, ¹H NMR (400 MHz, CDCl₃) δ: 1.32 (3H, t), 3.87 (2H, m), 4.29-4.38 (5H, m), 5.18 (1H, d), 7.65-7.70 (2H, m), 7.83 (1H, d), 7.93-8.02 (3H, m), 8.45 (1H, s), 8.76 (2H, s).

2-{3-[(2-Naphthylsulfonyl)amino]azetidin-1-yl}pyrimidine-5-carboxylic acid

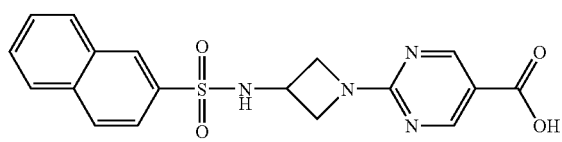

1M NaOH (10 ml) was added to a solution of ethyl 2-{3-[(2-naphthylsulfonyl)amino]azetidin-1-yl}pyrimidine-5-carboxylate (347 mg, 0.84 mmol) in THF (10 ml) and MeOH (2 ml) and the reaction stirred at r.t. overnight. The reaction mixture was acidified to pH~2 (2M HCl) before adjusting to pH~7 with sat. NaHCO₃ giving a white precipitate. The reaction was cooled to 0° C. and the precipitate isolated by filtration affording the title compound as a white solid (303 mg, 94%). LCMS purity 97%, m/z 385 [M+H]⁺.

N-(Tetrahydro-2H-pyran-2-yloxy) 2-{3-[(2-napthylsulfonyl)amino]azetidin-1-yl}pyrimidine-5-carboxamide

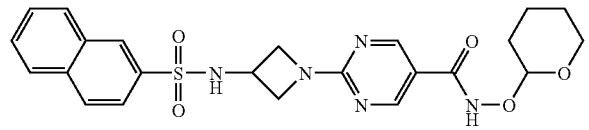

EDCl (90 mg, 0.47 mmol) was added to a solution of 2-{3-[(2-naphthylsulfonyl)amino]azetidin-1-yl}pyrimidine-5-carboxylic acid (150 mg, 0.39 mmol) in DCM (10 ml) and THF (10 ml) at r.t. under N₂. Et₃N (0.14 ml, 1.02 mmol), HOBt (63 mg, 0.47 mmol) and O-(tetrahydro-pyran-2-yl)-hydroxylamine (55 mg, 0.47 mmol) were added and the reaction stirred at r.t. overnight. The reaction mixture was concentrated in vacuo giving a colourless oil which was dissolved in DCM (20 ml), washed with water (3×20 ml), dried (Na₂SO₄) and concentrated in vacuo to give the title compound as a white solid (162 mg, 86%). LCMS purity 93%, m/z 484 [M+H]⁺.

N-Hydroxy 2-{3-[(2-naphthylsulfonyl)amino]azetidin-1-yl}pyrimidine-5-carboxamide—Example 70

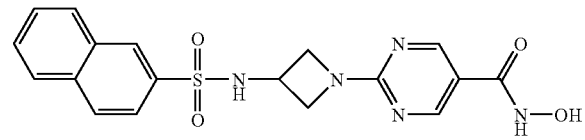

TFA (0.60 ml) was added to a solution of N-(tetrahydro-2H-pyran-2-yloxy) 2-{3-[(2-napthylsulfonyl)amino]azetidin-1-yl}pyrimidine-5-carboxamide (156 mg, 0.32 mmol) in DCM (10 ml) and MeOH (10 ml) at r.t. and the solution stirred at r.t. for 24 h. Further TFA (0.40 ml) was added and stirring continued for a further 18 h. The reaction mixture was concentrated in vacuo and the TFA was removed by azeotroping with DCM to yield a white foam. Trituration in hot DCM (15 ml) and MeOH (1 ml) gave a white precipitate which upon cooling to r.t. was isolated by filtration affording the title compound as a white solid (82 mg, 50%). LCMS purity 100%, m/z 400 [M+H]⁺, ¹H NMR (400 MHz, d₅-DMSO) δ: 3.64 (2H, m), 4.12 (2H, t), 4.31 (1H, br s), 7.71-7.76 (2H, m), 7.84 (1H, d), 8.09 (1H, d), 8.18-8.22 (2H, m), 8.49 (1H, s), 8.57 (3H, s), 9.01 (1H, s), 11.07 (1H, s).

Example 71

N-Hydroxy 2-{6-[(naphthalen-2-ylmethylamino)methyl]-3-azabicyclo[3.1.0]hex-3-yl}pyrimidine-5-carboxamide

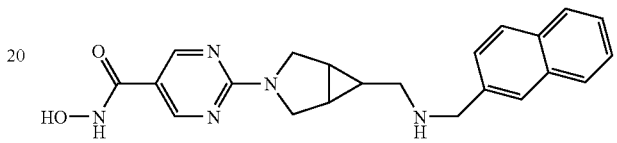

Example 71 was prepared following the methodology described in Scheme 15.

Ethyl 2-(6-{[(tert-butoxycarbonyl)amino]methyl}-3-azabicyclo[3.1.0]hex-3-yl)pyrimidine-5-carboxylate

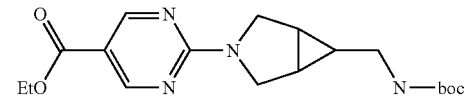

Intermediate C (2.27 g, 10.7 mmol) was stirred in MeCN/DMF (60 ml, 1:1) with K₂CO₃ (4.44 g, 32.1 mmol) at r.t. under N₂ for 10 min. Intermediate A (2.48 g, 10.7 mmol) was then added and the reaction stirred for 30 min. The reaction was then diluted with H₂O (100 ml) and extracted with EtOAc (2×100 ml). The combined organic extracts were dried (MgSO₄) and the solvent removed in vacuo. The residue was purified by column chromatography eluting with 0 to 5% MeOH in DCM to give the title compound as a white solid (3.5 g, 90%). LCMS purity 97%, m/z 363 [M+H]⁺, ¹H NMR (300 MHz, d₆-DMSO) δ: 0.70 (1H, m), 1.28 (3H, t, J=7.2 Hz), 1.38 (9H, s), 1.61 (2H, m), 2.93 (2H, m), 3.54 (2H, d, J=11.7 Hz), 3.82 (2H, d, J=11.7 Hz), 4.26 (2H, q, J=7.2 Hz), 6.92 (1H, m), 8.76 (2H, s).

Ethyl 2-[6-(aminomethyl)-3-azabicyclo[3.1.0]hex-3-yl]pyrimidine-5-carboxylate

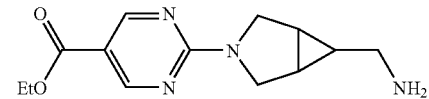

Ethyl 2-(6-{[(tert-butoxycarbonyl)amino]methyl}-3-azabicyclo[3.1.0]hex-3-yl)pyrimidine-5-carboxylate (1.7 g, 4.7 mmol) was stirred in DCM (20 ml) at r.t. under N₂. 4M HCl in dioxane (2.35 ml, 9.4 mmol) was added, immediately causing a solid to precipitate. The reaction was left to stir for 30 min and then the solvent was removed in vacuo. The residue was dissolved in DCM (100 ml) and washed with sat. aq. NaHCO₃ (100 ml). The organic layer was then dried (Na₂SO₄) and the solvent removed in vacuo to give the title compound as an orange solid (1.2 g, 97%). LCMS purity 97%, m/z 263 [M+H]⁺, ¹H NMR (300 MHz, d₆-DMSO) δ: 0.64 (1H, m), 1.29 (3H, t, J=7.2 Hz), 1.58 (2H, m), 3.33 (4H, m), 3.55 (2H, d, J=11.7 Hz), 3.82 (2H, d, J=11.7 Hz), 4.26 (2H, q, J=7.2 Hz), 8.76 (2H, s).

Ethyl 2-(6-{[(naphthalen-2-ylmethyl)amino]methyl}-3-aza-bicyclo[3.1.0]hex-3-yl)-pyrimidine-5-carboxylate

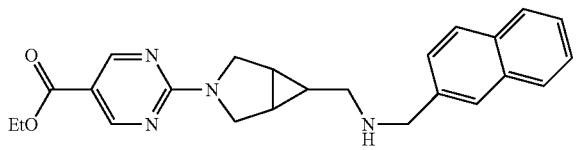

Ethyl 2-[6-(aminomethyl)-3-azabicyclo[3.1.0]hex-3-yl]pyrimidine-5-carboxylate (200 mg, 0.76 mmol) was stirred with 2-naphthaldehyde (119 mg, 0.76 mmol) in MeOH (10 ml) at r.t. under N₂ for 16 h. NaBH₄ (46 mg, 1.22 mmol) was then added and the mixture stirred for 10 min. Sat. aq. NH₄Cl (20 ml) was added and the mixture stirred for 20 min. The reaction was then diluted with H₂O (50 ml) and extracted with Et₂O (2×100 ml). The combined organic layers were dried (MgSO₄) and the solvent removed in vacuo to give the title compound as a yellow oil which was used in the next step without further purification. LCMS purity 92%, m/z 403 [M+H]⁺.

2-(6-{[(Naphthalen-2-ylmethyl)amino]methyl}-3-azabicyclo[3.1.0]hex-3-yl)pyrimidine-5-carboxylic acid

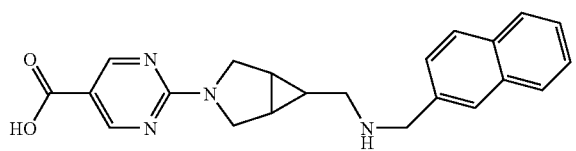

Ethyl 2-(6-{[(naphthalen-2-ylmethyl)amino]methyl}-3-aza-bicyclo[3.1.0]hex-3-yl)-pyrimidine-5-carboxylate (0.76 mmol) was stirred in THF (6 ml) and 1M NaOH (6 ml) at r.t. for 16 h. The reaction was then acidified to pH~3 with 2M HCl, causing a solid to precipitate. This was collected and dried to give the title compound as a white solid (72 mg, 25% over two steps) which was used in the next step without further purification. LCMS purity 96%, m/z 375 [M+H]⁺.

N-(1-Isobutoxyethoxy) 2-(6-{[(naphthalen-2-ylmethyl)amino]methyl}-3-aza-bicyclo[3.1.0]hex-3-yl) pyrimidine-5-carboxamide

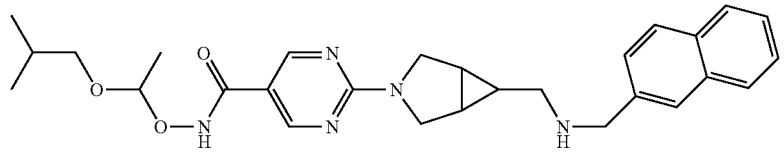

2-(6-{[(Naphthalen-2-ylmethyl)-amino]-methyl}-3-azabicyclo[3.1.0]hex-3-yl)-pyrimidine-5-carboxylic acid (72 mg, 0.19 mmol) was stirred with EDCl (44 mg, 0.23 mmol) and HOBt (31 mg, 0.23 mmol) in DMF (10 ml) at r.t. under N₂ for 10 min. Intermediate D (131 µl, 0.95 mmol) was then added followed by triethylamine (132 µl, 0.95 mmol) and the reaction allowed to stir for 64 h. The reaction was then diluted with H₂O (50 ml) and extracted with DCM (2×100 ml). The combined organic layers were dried (MgSO₄) and the solvent removed in vacuo. The residue was purified by column chromatography eluting with 0 to 10% MeOH in DCM to give the title compound as a colourless oil (43 mg, 46%). LCMS purity 97%, m/z 490 [M+H]⁺.

N-Hydroxy 2-{6-[(naphthalen-2-ylmethylamino)methyl]-3-azabicyclo[3.1.0]hex-3-yl}-pyrimidine-5-carboxamide—Example 71

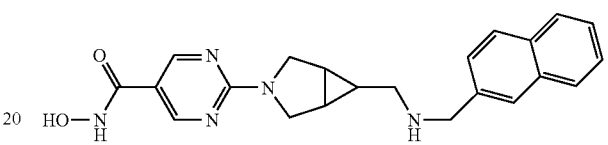

N-(1-Isobutoxyethoxy) 2-(6-{[(naphthalen-2-ylmethyl)amino]methyl}-3-azabicyclo[3.1.0]hex-3-yl)pyrimidine-5-carboxamide (43 mg, 0.09 mmol) was stirred in DCM (2 ml) at r.t. under N₂ and 4M HCl in dioxane (45 µl, 0.18 mmol) was added. This immediately caused a solid to precipitate. The reaction was allowed to stir for 10 min and then the solvent was removed in vacuo to give the title compound as a white solid (16 mg, 50%). LCMS purity 98%, m/z 390 [M+H]⁺, ¹H NMR (300 MHz, d₆-DMSO) δ: 1.91 (2H, m), 2.50 (1H, m), 2.99 (2H, m), 3.55 (2H, m), 3.88 (2H, d, J=11.7 Hz), 4.34 (2H, m), 7.58 (2H, m), 7.68 (1H, m), 7.95 (2H, m), 8.03 (2H, m), 8.66 (2H, s), 9.11 (2H, br s), 11.07 (1H, br s).

Examples 72 to 75 were prepared in an analogous manner to example 71:

Example 72

N-Hydroxy 2-{6-[(benzylamino)methyl]-3-azabicyclo[3.1.0]hex-3-yl}pyrimidine-5-carboxamide

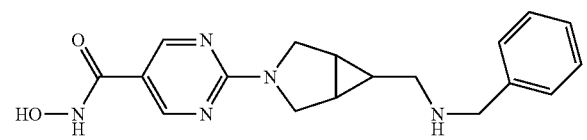

LCMS purity >99%, m/z 340 [M+H]⁺, ¹H NMR (300 MHz, CD₃OD) δ: 0.79 (1H, m), 1.65 (2H, br s), 2.74 (2H, d, J=7.2 Hz), 3.49 (2H, dm, J=11.4 Hz), 3.84 (2H, d, J=11.4 Hz), 3.94 (2H, s), 7.24-7.35 (5H, m), 8.54 (2H, s), no peaks for NH/NHOH due to MeOD.

Example 73

N-Hydroxy 2-(6-{[(4-chlorobenzyl)amino]methyl}-3-azabicyclo[3.1.0]hex-3-yl)pyrimidine-5-carboxamide

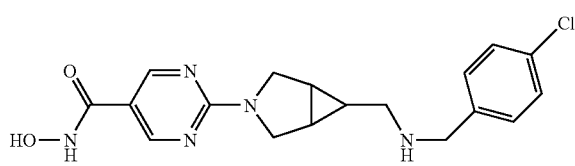

LCMS purity 99%, m/z 374 [M+H]+, 1H NMR (300 MHz, CD3OD) δ: 0.98 (1H, br s), 1.88 (2H, br d), 3.09 (2H, d, J=6.9 Hz), 3.62 (2H, d, J=11.7 Hz), 3.99 (2H, d, J=11.7 Hz), 4.24 (2H, s), 7.50 (4H, br s), 8.66 (2H, m), no peaks for NHOH/NH due to MeOD.

Example 74

N-Hydroxy 2-(6-{[(quinolin-2-ylmethyl)amino]methyl}-3-azabicyclo[3.1.0]hex-3-yl)pyrimidine-5-carboxamide

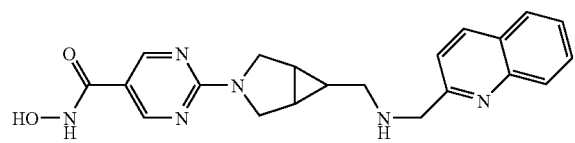

LCMS purity 98%, m/z 391 [M+H]+, 1H NMR (300 MHz, CD3OD) δ: 1.09 (1H, br s), 1.95 (2H, br s), 3.33 (2H, m), 3.64 (2H, d, J=11.7 Hz), 4.01 (2H, d, J=11.7 Hz), 4.64 (2H, s), 7.52 (1H, d, J=8.7 Hz), 7.66 (1H, t, J=7.2 Hz), 7.83 (1H, t, J=7.2 Hz), 7.99 (1H, d, J=8.7 Hz), 8.12 (1H, d, J=8.7 Hz), 8.41 (1H, d, J=8.7 Hz), 8.67 (2H, s), no peaks for NHOH/NH due to MeOD.

Example 75

N-Hydroxy 2-(6-{[(6-fluoroquinolin-2-ylmethyl)amino]methyl}-3-aza-bicyclo[3.1.0]hex-3-yl)pyrimidine-5-carboxamide

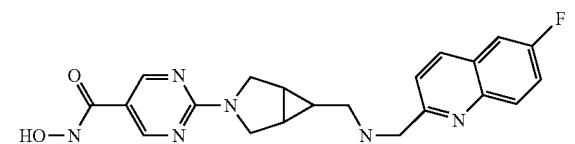

LCMS purity 99%, m/z 409 [M+H]+, 1H NMR (300 MHz, CD3OD) δ: 1.09 (1H, m), 1.95 (2H, br s), 3.25 (1H, d, J=7.2 Hz), 3.64 (2H, d, J=11.7 Hz), 4.01 (2H, d, J=11.7 Hz), 4.64 (2H, s), 7.56 (1H, d, J=8.4 Hz), 7.65 (2H, m), 8.17 (1H, dd, J=3.6, 5.4 Hz), 8.39 (1H, d, J=8.4 Hz), 8.68 (2H, s), no peaks for NHOH/NH due to MeOD.

Example 76

N-Hydroxy 2-[5-(naphthalene-2-sulfonyl)hexahydropyrrolo[3,4-c]pyrrol-2(1H)-yl]pyrimidine-5-carboxamide

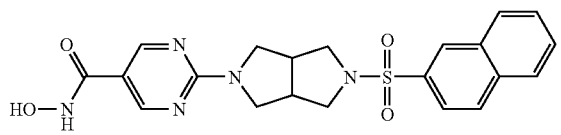

Example 76 was prepared following the methodology described in Scheme 16.

Ethyl 2-[5-(tert-butoxycarbonyl)hexahydropyrrolo[3,4-c]pyrrol-2(1H)-yl]pyrimidine-5-carboxylate

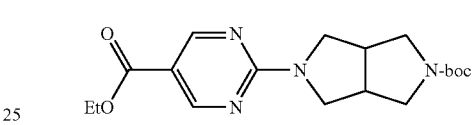

To a solution of tert-butyl hexahydro-pyrrolo[3,4-c]pyrrole-2-carboxylate (0.396 g, 1.86 mmol) in MeCN (10 ml) was added K2CO3 (0.377 g, 2.72 mmol) and then intermediate A (0.48 g, 2.08 mmol). The mixture was stirred for 90 min, and then poured into water (20 ml). The product was collected by filtration, then dried under vacuum to give the title compound as an off-white solid (0.437 g, 58%). 1H NMR (300 MHz, CDCl3) δ: 1.39 (3H, t), 1.47 (9H, s), 3.02 (2H, m), 3.22-3.41 (2H, m), 3.55-3.65 (4H, m), 3.80-3.97 (2H, m), 4.36 (2H, t), 8.88 (2H, s).

Ethyl 2-hexahydropyrrolo[3,4-c]pyrrol-2(1H)-ylpyrimidine-5-carboxylate

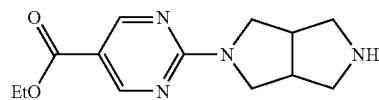

To ethyl 2-[5-(tert-butoxycarbonyl)hexahydropyrrolo[3,4-c]pyrrol-2(1H)-yl]pyrimidine-5-carboxylate (0.345 g, 0.9 mmol) was added 4M HCl in dioxane (2 ml, 8 mmol). The mixture was stirred at r.t. for 1 h, then evaporated to dryness. The residue was dissolved in methanol, loaded onto a SCX-2 cartridge, washed with methanol (100 ml), then eluted with 2M ammonia in methanol to give the title compound (0.285 g, 100%). LCMS purity >95%, m/z 263 [M+H]+.

Route I

Sulfonamide Preparation

Ethyl 2-[5-(naphthalene-2-sulfonyl)hexahydropyrrolo[3,4-c]pyrrol-2(1H)-yl]pyrimidine-5-carboxylate

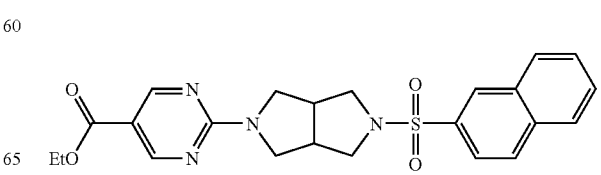

To a suspension of ethyl 2-hexahydropyrrolo[3,4-c]pyrrol-2(1H)-ylpyrimidine-5-carboxylate (0.271 g, 1.0 mmol) in pyridine (5 ml) was added 2-naphthalene sulfonyl chloride (0.269 g, 1.18 mmol). The mixture was stirred for 3 h, then water (25 ml) was added and the product collected by filtration. The product was washed with further water and then dried overnight under vacuum to give the title compound (0.231 g, 51%). $^1$H NMR (300 MHz, CDCl$_3$) δ: 1.39 (3H, t, J=6.9 Hz), 2.92-3.07 (2H, m), 3.29 (2H, dd, J=3.9, 10.2 Hz), 3.45 (2H, dd, J=3.9, 12.3 Hz), 3.59 (2H, dd, J=7.2, 10.2 Hz), 4.35 (2H, q, J=7.2 Hz), 7.58-7.75 (2H, m), 7.82 (1H, dd, J=1.8, 8.7 Hz), 7.90-8.05 (2H, m), 8.40 (1H, s), 8.77 (2H, s).

Route II

Amide Preparation

Ethyl 2-[5-(naphthalene-2-carbonyl)hexahydropyrrolo[3,4-c]pyrrol-2(1H)-yl]pyrimidine-5-carboxylate

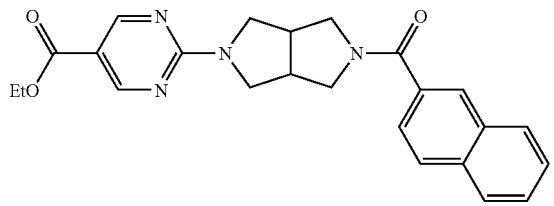

To a suspension of ethyl 2-hexahydropyrrolo[3,4-c]pyrrol-2(1H)-ylpyrimidine-5-carboxylate (0.156 g, 0.59 mmol) in pyridine (2 ml) was added 2-naphthalene carbonyl chloride (0.136 g, 0.71 mmol). The mixture was stirred for 3 h, then water (10 ml) was added and the product collected by filtration. The product was washed with further water and then dried overnight under vacuum to yield the title compound (0.217 g, 71%).

Route III

Amine Preparation

Ethyl 2-(5-naphthalen-2-ylmethylhexahydropyrrolo[3,4-c]pyrrol-2(1H)-yl)pyrimidine-5-carboxylate

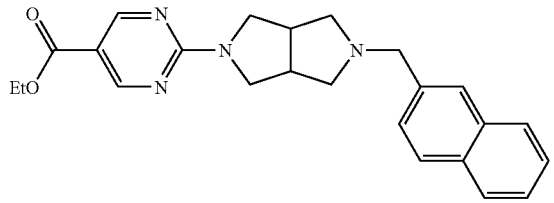

To a solution of ethyl 2-hexahydropyrrolo[3,4-c]pyrrol-2 (1H)-ylpyrimidine-5-carboxylate (0.187 g, 0.71 mmol) in DCE (2 ml) was added 2-naphthaldehyde (0.205 g, 1.31 mmol) and sodium triacetoxyborohydride (0.274 g, 1.25 mmol). The mixture was stirred for 3 h, then poured into DCM (100 ml). Sat. NaHCO$_3$ (100 ml) was added, and extracted with further DCM (100 ml). The combined organic extracts were dried (MgSO$_4$), concentrated and purified by flash column chromatography to yield the title compound (0.266 g, 99%). $^1$H NMR (300 MHz, CDCl$_3$) δ: 1.39 (3H, t, J=6.9 Hz), 2.59 (2H, d, J=6.9 Hz), 2.73-2.90 (2H, m), 2.94-3.10 (2H, m), 3.67 (2H, d, J=11.7 Hz), 3.82 (2H, s), 3.90 (2H, dd, J=8.1, 12 Hz), 4.37 (2H, q, J=7.2 Hz), 7.41-7.43 (3H, m), 7.74 (1H, s), 7.76-7.89 (3H, m), 8.88 (2H, s).

The following steps are described for example 76 (a sulphonamide) but they are equally applicable to amides and amines.

2-[5-(Naphthalene-2-sulfonyl)hexahydropyrrolo[3,4-c]pyrrol-2(1H)-yl]pyrimidine-5-carboxylic acid

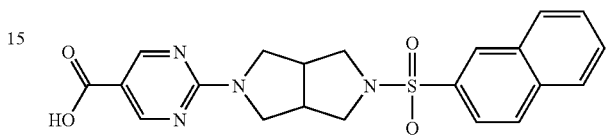

To a suspension of ethyl 2-[5-(naphthalene-2-sulfonyl)-hexahydro-pyrrolo[3,4-c]pyrrol-2-yl]-pyrimidine-5-carboxylate (0.201 g, 0.44 mmol) in ethanol (2 ml) was added 6M NaOH solution (2 ml, 12 mmol). The reaction was heated at 80° C. for 2 h, then cooled to r.t. The pH was adjusted to ~5 by addition of 2M HCl. The solution was allowed to stand overnight, and the product was collected by filtration to give the title compound (0.154 g, 82%). $^1$H NMR (300 MHz, d$_6$-DMSO) δ: 2.80-2.95 (2H, m), 3.17 (2H, dd, J=3.6, 10.2 Hz), 3.20-3.30 (2H, m), 3.46 (2H, dd J=7.2, 10.5 Hz), 3.61 (2H, dd, J=6.9, 11.7 Hz), 7.60-7.78 (2H, m), 7.82 (1H, dd, J=1.8, 8.7 Hz), 8.06 (1H, d, J=8.1 Hz), 8.13 (1H, d, J=8.7 Hz), 8.18 (1H, d, J=7.8 Hz), 8.47 (1H, s), 8.59 (2H, s).

N-(1-Isobutoxyethoxy) 2-[5-(naphthalene-2-sulfonyl)hexahydropyrrolo[3,4-c]pyrrol-2(1H)-yl]pyrimidine-5-carboxamide

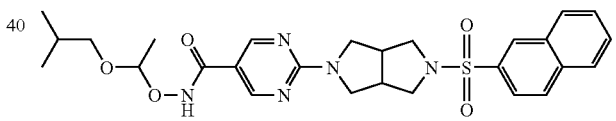

To a solution of 2-[5-(naphthalene-2-sulfonyl)-hexahydropyrrolo[3,4-c]pyrrol-2-yl]-pyrimidine-5-carboxylic acid (0.266 g, 0.71 mmol) in DMF (2 ml) was added EDCl (0.204 g, 1.06 mmol), HOBt (0.171 g, 1.1 mmol), intermediate D (1 ml, 7 mmol) and DIPEA (2 ml, 11 mmol). The reaction was stirred for 24 h, then loaded directly onto a silica gel column. The product was eluted with 2% MeOH/DCM to 5% MeOH/DCM to yield the title compound (0.255 g, 66%). This was carried onto the next step without characterisation.

N-Hydroxy 2-[5-(naphthalene-2-sulfonyl)hexahydropyrrolo[3,4-c]pyrrol-2(1H)-yl]pyrimidine-5-carboxamide—Example 76

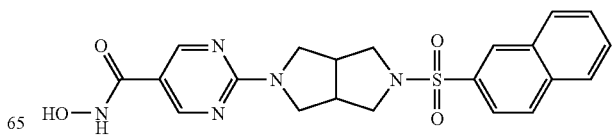

To N-(1-isobutoxyethoxy) 2-[5-(naphthalene-2-sulfonyl)-hexahydropyrrolo[3,4-c]pyrrol-2(1H)-yl]-pyrimidine-5-carboxamide (0.255 g, 0.5 mmol) was added TFA/DCM/MeOH (5 ml, 1:2:2 mixture). The solution was stirred for 2 h, then concentrated under vacuum. The residue was purified by reverse phase HPLC to yield the desired product (95 mg, 50%). LCMS purity >98%, m/z 440 [M+H]$^+$, $^1$H NMR (300 MHz, d$_6$-DMSO) δ: 2.90 (2H, br s), 3.24 (4H, dd, J=3.3, 10 Hz), 3.45 (2H, dd, J=6.8, 9.8 Hz), 3.61 (2H, dd, J=6.7, 11.4 Hz), 7.62-7.77 (2H, m), 7.83 (1H, dd, J=1.1, 8.5 Hz), 8.06 (1H, d, J=7.8 Hz), 8.13 (1H, d, J=8.8 Hz), 8.17 (1H, d, J=8.2 Hz), 8.47 (1H, s), 8.55 (2H, s), 11.02 (1H, s).

Examples 77 to 85 were prepared in an analogous manner to example 76:

Example 77

N-Hydroxy 2-[5-(naphthalene-2-carbonyl)hexahydropyrrolo[3,4-c]pyrrol-2(1H)-yl]pyrimidine-5-carboxamide

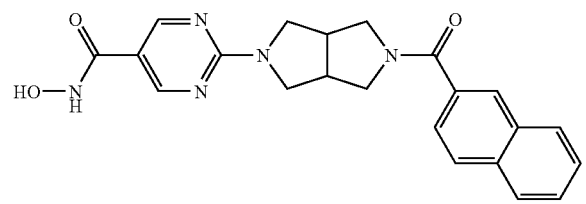

LCMS purity 98%, m/z 404 [M+H]$^+$, $^1$H NMR (300 MHz, d$_6$-DMSO) δ: 2.95-3.15 (2H, m), 3.25-3.63 (4H, m), 3.65-3.95 (4H, m), 7.52-7.68 (3H, m), 7.90-8.05 (3H, m), 8.13 (1H, s), 8.68 (2H, s), 8.99 (1H, br s), 11.07 (1H, br s).

Example 78

N-Hydroxy 2-[5-(4-phenoxybutyryl)hexahydropyrrolo[3,4-c]pyrrol-2(1H)-yl]pyrimidine-5-carboxamide

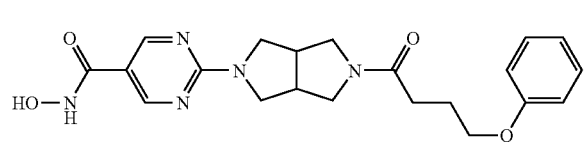

LCMS purity >98%, m/z 412 [M+H]$^+$, $^1$H NMR (300 MHz, CD$_3$OD) δ: 2.05-2.15 (2H, m), 2.46-2.67 (2H, m), 3.0-3.22 (2H, m), 3.38-3.58 (4H, m), 3.70-3.95 (4H, m), 3.97-4.08 (2H, m), 6.88-6.93 (3H, m), 7.22 (2H, dd, J=7.8, 7.8 Hz), 8.68 (2H, s).

Example 79

N-Hydroxy 2-(5-naphthalen-2-ylmethylhexahydropyrrolo[3,4-c]pyrrol-2(1H)-yl)pyrimidine-5-carboxamide

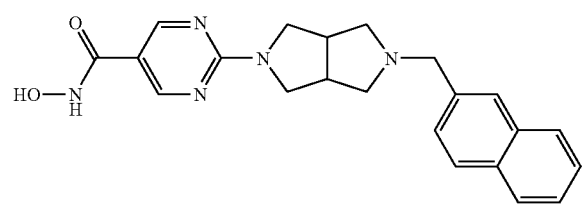

LCMS purity >98%, m/z 390 [M+H]$^+$, $^1$H NMR (300 MHz, d$_6$-DMSO) δ: 3.30-3.40 (2H, m), 3.40-3.90 (8H, m), 4.57 (2H, s), 7.61 (2H, s), 7.90-8.13 (3H, m), 8.65-8.75 (2H, m), 9.04 (1H, br s), 10.09 (1H, br s), 11.12 (1H, br s).

Example 80

N-Hydroxy 2-[5-(5-methoxyindan-1-yl)hexahydropyrrolo[3,4-c]pyrrol-2(1H)-yl]pyrimidine-5-carboxamide

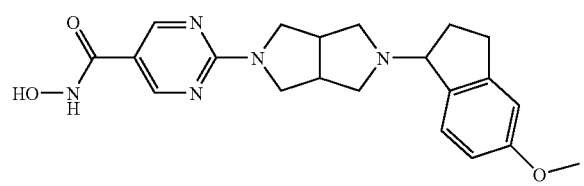

LCMS purity >98%, m/z 396 [M+H]$^+$, $^1$H NMR (300 MHz, CD$_3$OD) δ: 2.34-2.63 (2H, m), 2.88-3.05 (1H, m), 3.0-3.5 (9H, m), 3.53-3.80 (5H, m), 4.52-4.60 (1H, m), 6.87 (1H, d, J=7.7 Hz), 6.95 (1H, s), 7.48 (1H, d, J=8.2 Hz), 8.67 (2H, s).

Example 81

N-hydroxy 2-[5-(3,5-bistrifluoromethylbenzenesulfonyl)hexahydropyrrolo[3,4-c]pyrrol-2(1H)-yl]-pyrimidine-5-carboxamide

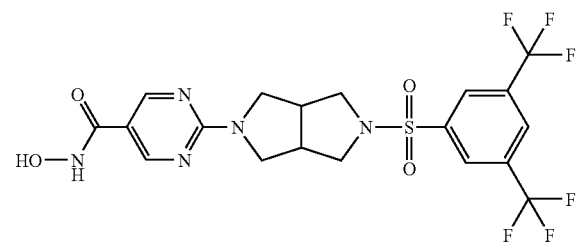

LCMS purity >98%, m/z 526 [M+H]$^+$, $^1$H NMR (300 MHz, d$_6$-DMSO) δ: 2.93-3.05 (2H, m), 3.20-3.28 (4H, m), 3.50 (2H, dd, J=6.4, 9.8 Hz) 3.63 (2H, dd, J=7.3, 11.9 Hz), 8.34 (2H, s), 8.52 (1H, s), 8.63 (2H, s), 8.99 (1H, br s), 11.06 (1H, br s).

Example 82

N-Hydroxy 2-[5-{[4-(trifluoromethoxy)phenyl]sulfonyl}hexahydropyrrolo[3,4-c]pyrrol-2(1H)-yl]pyrimidine-5-carboxamide

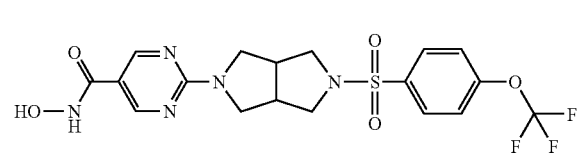

LCMS purity >98%, m/z 474 [M+H]⁺, ¹H NMR (300 MHz, d₆-DMSO) δ: 2.87-3.00 (2H, m), 3.13 (2H, dd, J=3.6, 10.1 Hz), 3.21 (2H, dd, J=3.5, 11.7 Hz), 3.33-3.46 (2H, dd, J=7.0, 10.3 Hz), 3.65 (2H, dd, J=6.9, 11.5 Hz), 7.60 (2H, d, J=8.0 Hz), 7.95 (2H, d, J=8.8 Hz), 8.64 (2H, s), 8.97 (1H, br s), 11.05 (1H, br s).

Example 83

N-Hydroxy 2-[5-(3,5-difluorobenzyl)hexahydropyrrolo[3,4-c]pyrrol-2(1H)-yl]pyrimidine-5-carboxamide

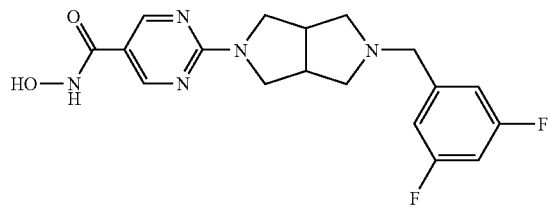

LCMS purity >98%, m/z 376 [M+H]⁺, ¹H NMR (300 MHz, d₆-DMSO) δ: 3.00-3.15 (2H, m), 3.42-3.51 (2H, m), 3.53-3.65 (2H, m), 3.65-3.88 (4H, m), 4.42 (2H, s), 7.22-7.33 (2H, m), 7.39 (1H, t, J=9.3 Hz), 8.70 (2H, s), 11.21 (1H, br s), 11.10 (1H, br s).

Example 84

N-Hydroxy 2-[5-(4-methoxybenzyl)hexahydropyrrolo[3,4-c]pyrrol-2(1H)-yl]pyrimidine-5-carboxamide

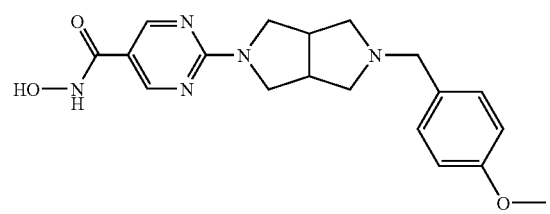

LCMS purity >98%, m/z 370 [M+H]⁺, ¹H NMR (300 MHz, d₆-DMSO) δ: 2.9-3.1 (2H, m), 3.25-3.45 (2H, m), 3.52-3.85 (6H, m), 3.78 (3H, s), 4.28-4.35 (2H, m), 6.97-7.05 (2H, m), 7.39-7.48 (2H, m), 8.67-8.73 (2H, m), 9.88 (1H, br s), 11.10 (1H, br s).

Example 85

N-Hydroxy 2-[5-(4-chlorobenzyl)hexahydropyrrolo[3,4-c]pyrrol-2(1H)-yl]pyrimidine-5-carboxamide

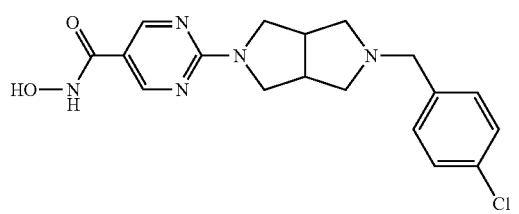

LCMS purity >98%, m/z 374 [M+H]⁺, ¹H NMR (300 MHz, d₆-DMSO) δ: 2.98-3.12 (2H, m), 3.28-3.50 (2H, m), 3.52-3.71 (4H, m), 3.72-3.86 (2H, m), 4.36-4.45 (2H, m), 7.50-7.58 (4H, m), 8.66-8.75 (2H, m), 10.08 (1H, br s), 11.11 (1H, br s).

Example 86

N-Hydroxy 2-[9-(naphthalene-2-sulfonyl)-3,9-diazaspiro[5.5]undec-3-yl]pyrimidine-5-carboxamide

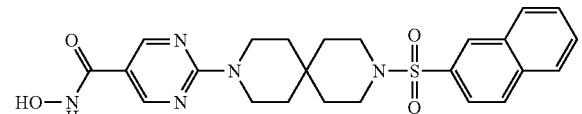

Example 86 was prepared following the methodology described in Scheme 17.

The title compound was prepared from tert-butyl 3,9-diaza-spiro[5.5]undecane-3-carboxylate using the same methodology described for example 76. LCMS purity 90%, m/z 482 [M+H]⁺, ¹H NMR (300 MHz, d₆-DMSO) δ: 1.30 (4H, m), 1.58 (4H, m), 3.03 (4H, m), 3.70 (4H, m), 7.69 (1H, dd, J=1.3, 6.9 Hz), 7.74 (1H, dd, J=1.9, 8.1 Hz), 7.78 (1H, dd, J=2.1, 8.7 Hz), 8.10 (2H, d, J=7.8 Hz), 8.15 (1H, d, J=8.7 Hz), 8.22 (2H, d, J=5.2 Hz), 8.45 (2H, br s), 8.60 (2H, s).

Example 87

N-Hydroxy 6-(5-naphthalen-2-ylmethyl-hexahydropyrrolo[3,4-c]pyrrol-2-yl)-pyridine-5-carboxamide

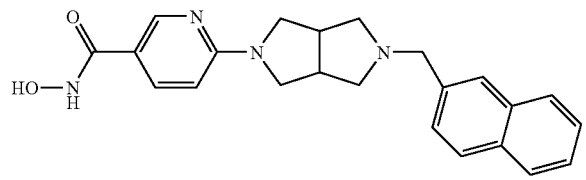

Example 87 was prepared following the methodology described in Scheme 18.

Ethyl 2-[5-(tert-butoxycarbonyl)hexahydropyrrolo[3,4-c]pyrrol-2(1H)-yl]pyridine-5-carboxylate

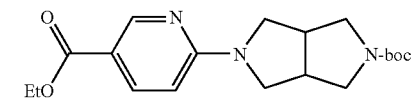

To a solution of tert-butyl hexahydro-pyrrolo[3,4-c]pyrrole-2-carboxylate (1.11 g, 5.23 mmol) in dioxane were added ethyl 6-chloronicotinate (1.28 g, 6.9 mmol) and DIPEA (2 ml, 11.6 mmol). The mixture was heated at 75° C. for 3 days. The mixture was then poured into EtOAc (100 ml) and washed with saturated ammonium chloride (50 ml), water (50 ml) and brine (50 ml). The organic fraction was dried (MgSO₄), concentrated and purified by flash column chromatography (5% MeOH-DCM) to yield the title compound (1.429 g, 75%). m/z 362.25 [M+H]⁺; ¹H NMR (300 MHz, CDCl₃) δ: 8.32 (1H, dd, J=0.6, 2.1 Hz), 8.03 (1H, dd, J=2.4, 9.0 Hz), 6.32 (1H, d, J=8.7 Hz), 4.34 (2H, q, J=6.9 Hz), 3.24-3.85 (8H, m), 3.03 (2H, m), 1.47 (9H, s), 1.38 (3H, t, J=7.2 Hz).

Ethyl 2-hexahydropyrrolo[3,4-c]pyrrol-2(1H)-ylpyridine-5-carboxylate hydrochloride

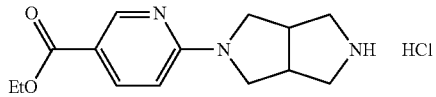

To ethyl 2-[5-(tert-butoxycarbonyl)hexahydropyrrolo[3,4-c]pyrrol-2(1H)-yl]pyridine-5-carboxylate (1.429 g, 3.92 mmol) was added 4M HCl in dioxane (10 ml, 40 mmol). The mixture was stirred for 2 h, then Et₂O (50 ml) was added. The product was collected by filtration and washed with further Et₂O (50 ml) to yield the title compound (1.19 g, quant.). ¹H NMR (300 MHz, d₆-DMSO) δ: 9.95 (1H, br s), 9.84 (1H, br s), 8.44 (1H, d, J=1.8 Hz), 8.20 (1H, dd, J=2.1, 9.3 Hz), 7.01 (1H, d, J=9.3 Hz), 4.31 (2H, q, J=7.2 Hz), 3.0-4.05 (10H, m), 1.31 (3H, t, J=7.2 Hz).

Ethyl 6-(5-naphthalen-2-ylmethyl-hexahydro-pyrrolo[3,4-c]pyrrol-2-yl)pyridine-5-carboxamide

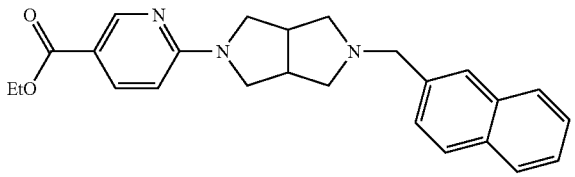

To a suspension of ethyl 2-hexahydropyrrolo[3,4-c]pyrrol-2(1H)-ylpyridine-5-carboxylate hydrochloride (0.54 g, 1.81 mmol) in DCE (5 ml) were added 2-naphthaldehyde (0.57 g, 3.64 mmol) and sodium triacetoxyborohydride (0.78 g, 3.68 mmol). The mixture was stirred overnight, and then poured into saturated sodium bicarbonate (100 ml). The product was extracted with DCM (2×100 ml), and the combined extracts were dried (MgSO₄), concentrated and purified by flash column chromatography (4% MeOH-DCM) to yield the title compound (0.255 g, 35%). ¹H NMR (300 MHz, d₆-DMSO) δ: 8.63 (1H, d, J=2.1 Hz), 7.92 (1H, dd, J=2.4, 9.0 Hz), 7.75-7.89 (3H, m), 7.44-7.49 (3H, m), 6.53 (1H, d, J=8.7 Hz), 4.25 (2H, q, J=7.2 Hz), 3.65-3.74 (4H, m), 3.35-3.41 (2H, m), 2.94 (2H, m), 2.57-2.64 (2H, m), 1.29 (3H, t, J=7.2 Hz).

6-(5-Naphthalen-2-ylmethyl-hexahydro-pyrrolo[3,4-c]pyrrol-2-yl)pyridine-5-carboxylic acid

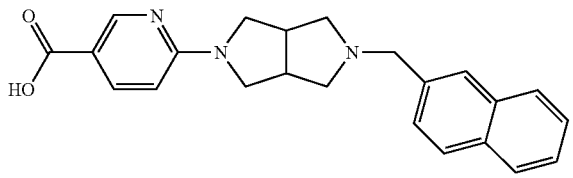

To a suspension of ethyl 6-(5-naphthalen-2-ylmethyl-hexahydro-pyrrolo[3,4-c]pyrrol-2-yl)pyridine-5-carboxamide (0.255 g, 0.63 mmol) in EtOH (2 ml) was added 6M NaOH (2 ml, 12 mmol). The mixture was heated at 80° C. for 90 min and then cooled to r.t. Concentrated HCl was then added until a precipitate formed, and the solid was collected by filtration (240 mg, quant.). The compound was carried onto the next step without characterization.

N-(1-Isobutoxyethoxy) 6-(5-naphthalen-2-ylmethyl-hexahydro-pyrrolo[3,4-c]pyrrol-2-yl)pyridine-5-carboxamide

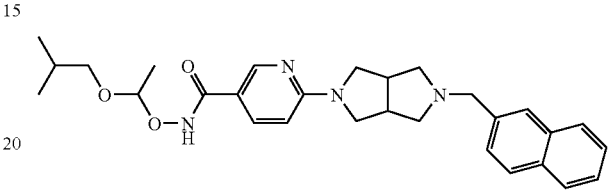

To a solution of 6-(5-naphthalen-2-ylmethyl-hexahydro-pyrrolo[3,4-c]pyrrol-2-yl)pyridine-5-carboxylic acid (0.24 g, 0.6 mmol) in DMF (5 ml) were added HOBt (0.26 g, 1.7 mmol), EDCl (0.303 g, 1.6 mmol), DIPEA (1 ml, 5.8 mmol), and intermediate D (1 ml, 7.4 mmol). The mixture was stirred overnight and then poured into Et₂O (250 ml). This was washed with water (50 ml), saturated sodium bicarbonate (50 ml), water (50 ml) and brine (50 ml). The extract was then dried (MgSO₄), concentrated and purified by flash column chromatography (4% MeOH-DCM) to yield the title compound (0.199 g, 58%). ¹H NMR (300 MHz, d₆-DMSO) δ: 11.17 (1H, br s), 8.50 (1H, d, J=2.1 Hz), 7.81-7.90 (4H, m), 7.77 (1H, s), 7.42-7.50 (3H, m), 6.52 (1H, d, J=8.8 Hz), 4.95 (2H, q, J=7.0 Hz), 3.61-3.74 (6H, m), 2.88-2.99 (2H, m), 2.60-2.69 (2H, m), 1.72-1.84 (1H, m), 1.31 (3H, d, J=5.1 Hz), 0.86 (6H, d, J=6.6 Hz).

N-Hydroxy 6-(5-naphthalen-2-ylmethyl-hexahydro-pyrrolo[3,4-c]pyrrol-2-yl)pyridine-5-carboxamide—Example 87

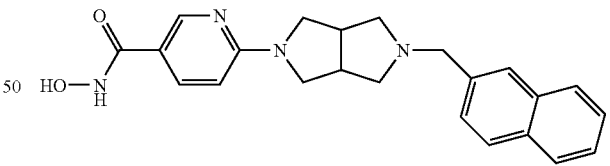

To N-(1-isobutoxyethoxy) 6-(5-naphthalen-2-ylmethyl-hexahydro-pyrrolo[3,4-c]pyrrol-2-yl)pyridine-5-carboxamide (0.199 g, 0.4 mmol) was added TFA:DCM:MeOH (8 ml, 1:2:2). The solution was stirred for 6 h and then concentrated under vacuum. The residue was suspended in MeOH and poured into EtOH (250 ml). The mixture was washed with 1:1 saturated sodium bicarbonate/1M NaOH (100 ml), and water (50 ml). The organic fraction was dried (Na₂SO₄), concentrated and purified by reverse phase HPLC to yield the title compound (9 mg, 5%). m/z 389.25 [M+H]⁺; ¹H NMR (300 MHz, CD₃OD) δ: 2.64 (2H, d, J=5.3 Hz), 2.90-3.07 (4H, m), 3.37-3.58 (4H, m), 3.89 (2H, s), 6.46 (1H, d, J=8.9 Hz), 7.33-7.44 (3H, m), 7.70-7.80 (5H, m), 8.37 (1H, d, J=2.2 Hz).

Example 88

N-Hydroxy 4-{6-[(naphthalen-2-ylmethyl)-amino]-3-azabicyclo[3.1.0]hex-3-yl}-benzamide

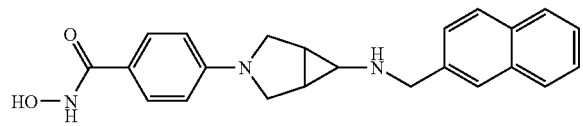

Example 88 was prepared following the methodology described in Scheme 19.

tert-Butyl 6-(naphthalene-2-methylamino)-3-azabicyclo[3.1.0]hexane-3-carboxylate

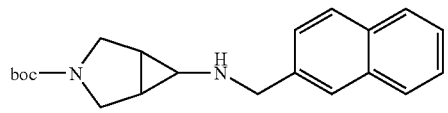

The title compound was prepared as described in example 20.

6-(Naphthalene-2-methylamino)-3-azabicyclo[3.1.0]hexane

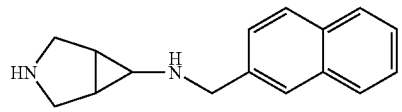

tert-Butyl 6-(naphthalene-2-methylamino)-3-azabicyclo[3.1.0]hexane-3-carboxylate (800 mg, 2.37 mmol) was stirred in 4M HCl in dioxane (10 ml) at r.t. for 1 h and then at 40° C. for a further 1.5 h. The solvent was then removed in vacuo and the residue dried and used in the next step without further purification. LCMS purity 90%, m/z 239 [M+H]⁺.

Ethyl 4-{6-[(naphthalen-2-ylmethyl)-amino]-3-azabicyclo[3.1.0]hex-3-yl}-benzoate

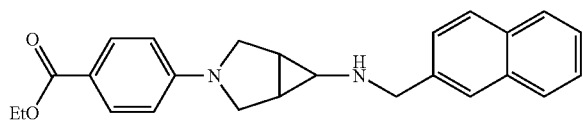

6-(Naphthalene-2-methylamino)-3-azabicyclo[3.1.0]hexane (2.37 mmol) was stirred in DMSO (30 ml) at r.t. under N₂. K₂CO₃ (3.27 g, 23.70 mmol) and ethyl 4-fluorobenzoate were then added and the reaction stirred at 100° C. for 3 days. The reaction was then allowed to cool to r.t. and poured into H₂O (100 ml). This was extracted with DCM (2×100 ml), the combined organic layers dried (MgSO₄) and the solvent removed in vacuo to give the title product as an orange oil which was used in the next step without further purification. LCMS purity 70%, m/z 387 [M+H]⁺.

4-{6-[(Naphthalen-2-ylmethyl)-amino]-3-aza-bicyclo[3.1.0]hex-3-yl}-benzoic acid trimethylsylanoate

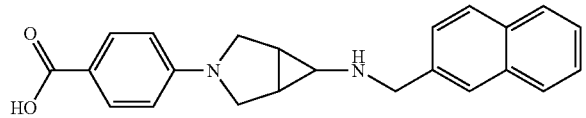

Ethyl 4-{6-[(naphthalen-2-ylmethyl)-amino]-3-aza-bicyclo[3.1.0]hex-3-yl}-benzoate (500 mg, 1.29 mmol) was stirred in THF (30 ml) with potassium trimethylsilanolate (332 mg, 2.58 mmol) at r.t. under N₂ for 6 h. More potassium trimethylsilanolate (332 mg, 2.58 mmol) was added and the reaction stirred at 50° C. for 4 days. The reaction was allowed to cool to r.t. and a precipitate formed. This was isolated by filtration, dried and used in the next step without further purification. LCMS purity 60%, m/z 359 [M+H]⁺.

N-(1-Isobutoxyethoxy) 4-{6-[(naphthalen-2-ylmethyl)-amino]-3-aza-bicyclo[3.1.0]hex-3-yl}-benzamide

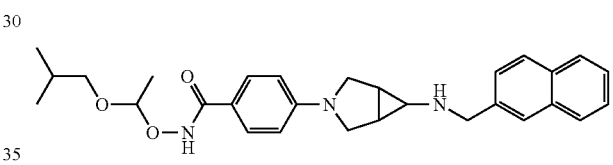

4-{6-[(Naphthalen-2-ylmethyl)-amino]-3-aza-bicyclo[3.1.0]hex-3-yl}-benzoic acid trimethylsylanoate (1.29 mmol) was stirred in DMF (30 ml) at r.t. under N₂. EDCl (297 mg, 1.55 mmol), HOBt (209 mg, 1.55 ml), intermediate D (89 µl, 6.45 mmol) and NEt₃ (899 µl, 6.45 mmol) were added and the reaction stirred at 50° C. for 24 h. After this time the reaction was cooled to r.t. and diluted with water (100 ml). It was then extracted with DCM (2×100 ml), the organic layer dried (MgSO₄) and concentrated in vacuo. The residue was purified by column chromatography (10% MeOH in DCM) to give the title compound as an orange oil (117 mg, 19%). LCMS purity 70%, m/z 474 [M+H]⁺.

N-Hydroxy 4-{6-[(naphthalen-2-ylmethyl)-amino]-3-aza-bicyclo[3.1.0]hex-3-yl}-benzamide—Example 88

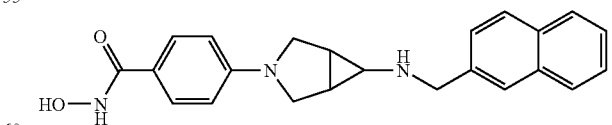

N-(1-Isobutoxyethoxy) 4-{6-[(naphthalen-2-ylmethyl)-amino]-3-aza-bicyclo[3.1.0]hex-3-yl}-benzamide (117 mg, 0.25 mmol) was stirred in DCM (10 ml) at r.t. and 4M HCl in dioxane (0.5 ml) was added. The reaction was allowed to stir for 30 min and then the solvent was removed in vacuo. The residue was purified by Gilson HPLC to give the title compound as a pink solid (13 mg, 14%). LCMS purity 98%, m/z 374 [M+H]+. $^1$H NMR (300 MHz, CD$_3$OD) δ: 2.25 (2H, br s), 2.71 (1H, s), 3.32 (2H, m), 3.71 (2H, d, J=9.3 Hz), 4.54 (2H, s), 6.61 (2H, d, J=8.1 Hz), 7.62 (5H, m), 7.95 (4H, m), no peaks for NH/NHOH due to CD$_3$OD.

Measurement of Biological Activities

Histone Deacetylase Activity

The ability of compounds to inhibit histone deacetylase activities was measured using the commercially available HDAC fluorescent activity assay from Biomol. In brief, the Fluor de Lys™ substrate, a lysine with an epsilon-amino acetylation, is incubated with the source of histone deacetylase activity (HeLa nuclear extract) in the presence or absence of inhibitor. Deacetylation of the substrate sensitises the substrate to Fluor de Lys™ developer, which generates a fluorophore. Thus, incubation of the substrate with a source of HDAC activity results in an increase in signal that is diminished in the presence of an HDAC inhibitor.

Data are expressed as a percentage of the control, measured in the absence of inhibitor, with background signal being subtracted from all samples, as follows:—

% activity=$[(S^i-B)/(S^o-B)]\times100$ where $S^i$ is the signal in the presence of substrate, enzyme and inhibitor, $S^o$ is the signal in the presence of substrate, enzyme and the vehicle in which the inhibitor is dissolved, and B is the background signal measured in the absence of enzyme.

IC50 values were determined by non-linear regression analysis, after fitting the results of eight data points to the equation for sigmoidal dose response with variable slope (% activity against log concentration of compound), using Graphpad Prism software.

Histone deacetylase activity from crude nuclear extract derived from HeLa cells was used for screening. The preparation, purchased from 4C (Seneffe, Belgium), was prepared from HeLa cells harvested whilst in exponential growth phase. The nuclear extract is prepared according to Dignam JD1983 Nucl. Acid. Res. 11, 1475-1489, snap frozen in liquid nitrogen and stored at −80° C. The final buffer composition was 20 mM Hepes, 100 mM KCl, 0.2 mM EDTA, 0.5 mM DTT, 0.2 mM PMSF and 20% (v/v) glycerol.

IC50 results were allocated to one of 3 ranges as follows:
Range A: IC50<100 nM,
Range B: IC50 from 101 nM to 1000 nM;
and Range C: IC50>1000 nM.

U937 and HUT Cell Inhibition Assay

Cancer cell lines (U937 and HUT) growing in log phase were harvested and seeded at 1000-2000 cells/well (100 µl final volume) into 96-well tissue culture plates. Following 24 h of growth cells were treated with compound. Plates were then re-incubated for a further 72-96 h before a WST-1 cell viability assay was conducted according to the suppliers (Roche Applied Science) instructions.

Data were expressed as a percentage inhibition of the control, measured in the absence of inhibitor, as follows:—

% inhibition=$100-[(S^i/S^o)\times100]$ where $S^i$ is the signal in the presence of inhibitor and $S^o$ is the signal in the presence of DMSO.

Dose response curves were generated from 8 concentrations (top final concentration 10 µM, with 3-fold dilutions), using 6 replicates.

IC50 values were determined by non-linear regression analysis, after fitting the results to the equation for sigmoidal dose response with variable slope (% activity against log concentration of compound), using Graphpad Prism software.

IC50 results were allocated to one of 3 ranges as follows:
Range A: IC50<330 nM,
Range B: IC50 from 331 nM to 3300 nM;
and Range C: IC50>3300 nM.

HeLa Cell Inhibition Assay

HeLa cells growing in log phase were harvested and seeded at 1000 cells/well (200 µl final volume) into 96-well tissue culture plates. Following 24 h of cell growth cells were treated with compounds (final concentration of 20 µM). Plates were then re-incubated for a further 72 h before a sulphorhodamine B (SRB) cell viability assay was conducted according to Skehan 1990 J Natl Canc Inst 82, 1107-1112.

Data were expressed as a percentage inhibition of the control, measured in the absence of inhibitor, as follows:—

% inhibition=$100-[(S^i/S^o)\times100]$ where $S^i$ is the signal in the presence of inhibitor and $S^o$ is the signal in the presence of DMSO.

IC50 values were determined by non-linear regression analysis, after fitting the results of eight data points to the equation for sigmoidal dose response with variable slope (% activity against log concentration of compound), using Graphpad Prism software.

IC50 results were allocated to one of 3 ranges as follows:
Range A: IC50<330 nM,
Range B: IC50 from 331 nM to 3300 nM;
and Range C: IC50>3300 nM.

Results Table

| Example No. | HDAC activity | HeLa activity | U937 activity | HUT activity |
|---|---|---|---|---|
| 1 | A | A | A | A |
| 2 | A | C | C | C |
| 3 | A | B | A | A |
| 4 | A | B | A | A |
| 5 | A | B | B | A |
| 6 | A | C | C | C |
| 7 | A | B | B | B |
| 8 | A | B | B | A |
| 9 | A | B | B | B |
| 10 | A | B | B | B |
| 11 | A | B | C | B |
| 12 | A | B | B | B |
| 13 | A | B | B | B |
| 14 | A | B | B | B |
| 15 | A | B | B | B |
| 16 | A | B | B | A |
| 17 | A | B | B | A |
| 18 | A | C | C | B |
| 19 | A | A | A | A |
| 20 | A | B | A | A |
| 21 | A | B | A | A |
| 22 | A | A | A | A |
| 23 | A | B | B | A |
| 24 | A | B | A | A |
| 25 | A | A | A | A |
| 26 | A | A | A | A |
| 27 | A | A | A | A |
| 28 | A | A | A | A |
| 29 | A | A | A | A |
| 30 | A | A | A | A |
| 31 | A | B | A | A |
| 32 | A | A | A | A |
| 33 | A | A | A | A |
| 34 | A | B | A | A |
| 35 | A | A | A | A |
| 36 | A | n/d | A | A |
| 37 | A | A | A | A |
| 38 | A | B | B | A |
| 39 | A | B | A | A |
| 40 | A | B | B | A |

Results Table

| Example No. | HDAC activity | HeLa activity | U937 activity | HUT activity |
|---|---|---|---|---|
| 41 | A | B | A | A |
| 42 | A | B | B | A |
| 43 | A | A | A | A |
| 44 | A | A | A | A |
| 45 | A | B | B | A |
| 46 | A | A | A | A |
| 47 | A | B | B | B |
| 48 | A | B | B | B |
| 49 | A | B | B | B |
| 50 | A | n/d | A | A |
| 51 | A | A | A | A |
| 52 | A | B | B | A |
| 53 | A | A | A | A |
| 54 | A | B | B | B |
| 55 | A | C | B | B |
| 56 | A | A | B | A |
| 57 | C | C | C | C |
| 58 | B | B | B | B |
| 59 | A | A | A | A |
| 60 | A | A | A | A |
| 61 | A | B | B | A |
| 62 | B | C | C | B |
| 63 | B | C | C | B |
| 64 | A | B | B | A |
| 65 | A | B | B | B |
| 66 | A | B | B | B |
| 67 | A | B | B | A |
| 68 | A | A | A | A |
| 69 | A | C | C | B |
| 70 | A | C | C | B |
| 71 | A | B | B | A |
| 72 | A | B | B | A |
| 73 | A | B | B | A |
| 74 | A | B | B | A |
| 75 | B | B | B | B |
| 76 | A | B | B | A |
| 77 | A | A | B | A |
| 78 | A | C | B | B |
| 79 | A | A | A | A |
| 80 | A | A | B | A |
| 81 | A | C | B | B |
| 82 | A | B | B | B |
| 83 | A | B | A | A |
| 84 | A | B | B | A |
| 85 | A | B | A | A |
| 86 | B | C | B | B |
| 87 | A | B | B | B |
| 88 | B | B | B | B |

The invention claimed is:

1. A compound of formula (IA) or a salt or N-oxide thereof:

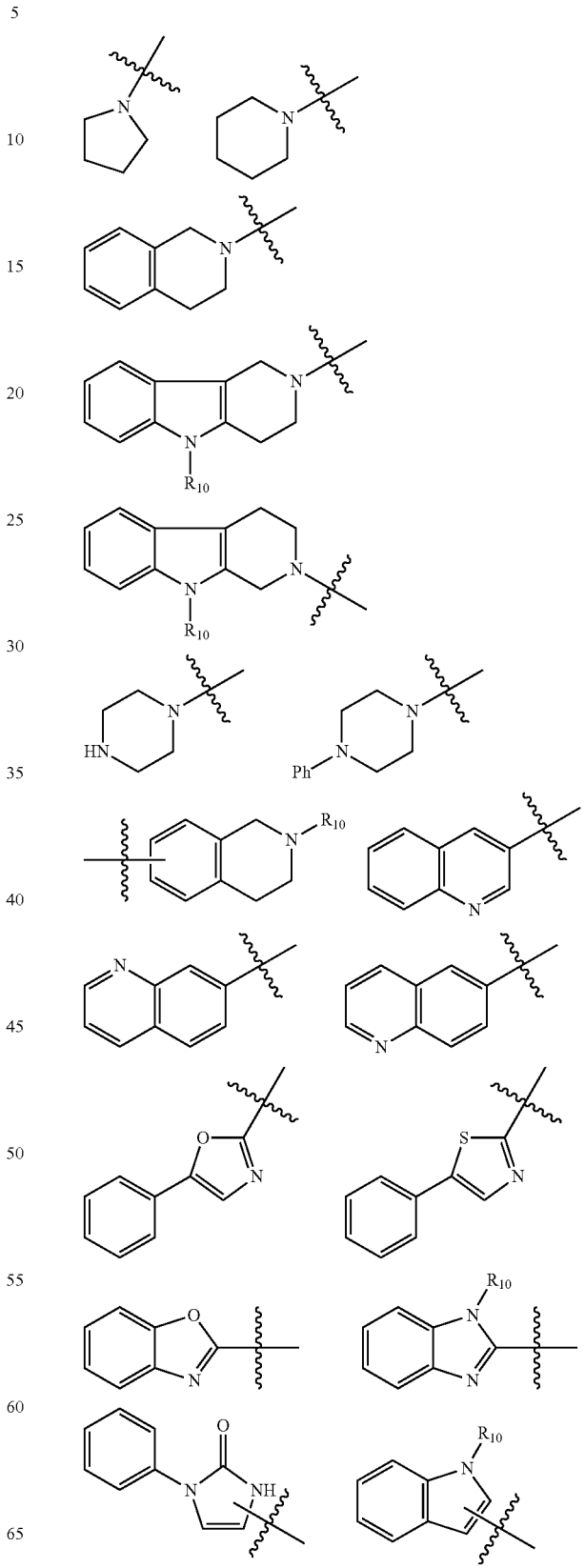

(IA)

wherein T is —S(=O)$_2$—, —C(=O)— or —CH$_2$—, and A is one of the following ring systems, optionally substituted:

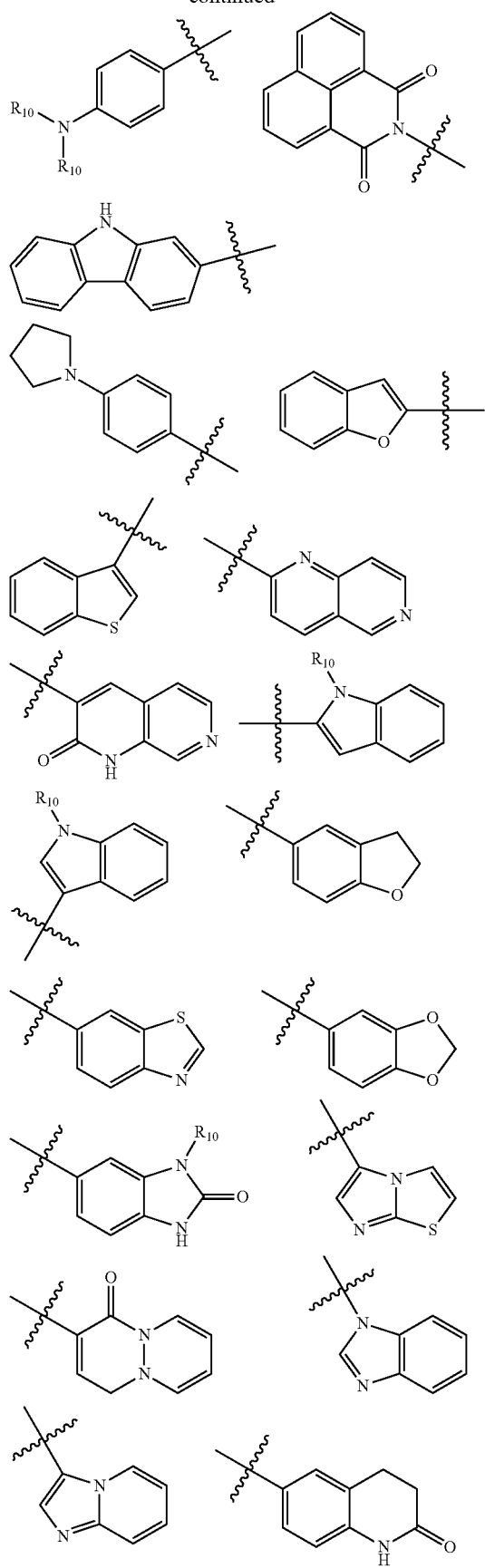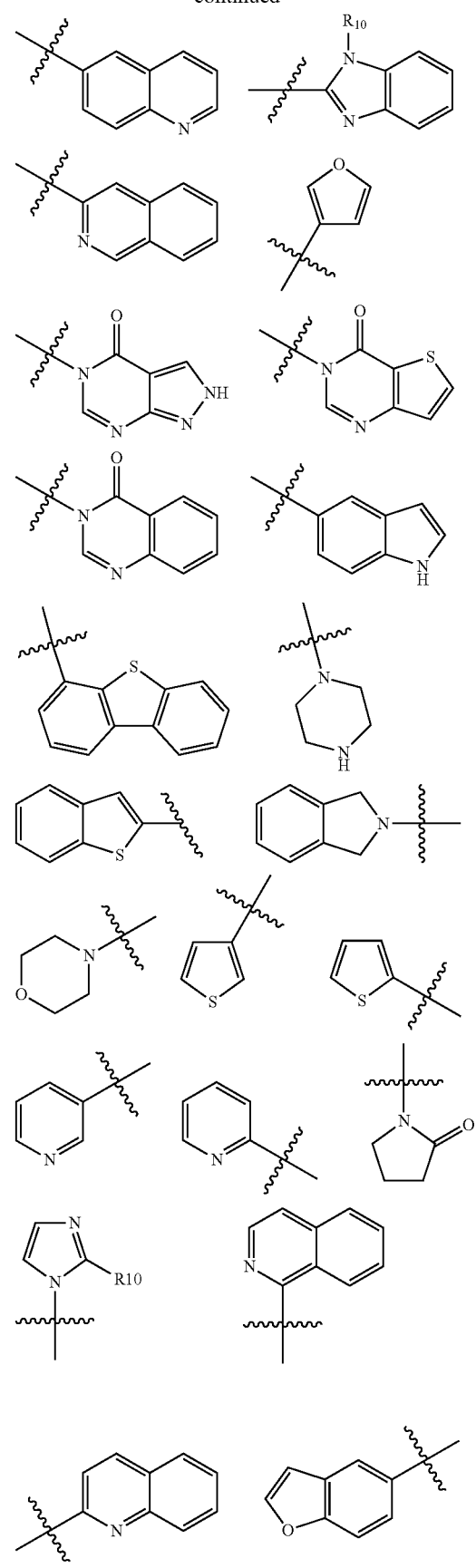

-continued

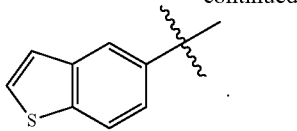

2. A compound as claimed in claim 1 wherein ring A is optionally substituted quinolin-2-yl, or 1,3-dihydro-isoindol-2-yl.

3. A compound as claimed in claim 2 wherein optional substituents in ring A are selected from fluoro and chloro.

4. A compound as claimed in claim 1 which is selected from the group consisting of the following:

N-Hydroxy 2-{6-[(6-fluoro-quinolin-2-ylmethyl)-amino]-3-aza-bicyclo[3.1.0]hex-3-yl}pyrimidine-5-carboxamide, and N-Hydroxy 2-{6-[(quinolin-2-ylmethyl)-amino]-3-aza-bicyclo[3.1.0]hex-3-yl}pyrimidine-5-carboxamide, and their N-oxides or salts, hydrates and solvates.

5. A pharmaceutical composition comprising a compound as claimed in claim 1, together with a pharmaceutically acceptable carrier.

6. A pharmaceutical composition as claimed in claim 5 wherein the said compound is selected from the group consisting of the following:

N-Hydroxy 2-{6-[(6-fluoro-quinolin-2-ylmethyl)-amino]-3-aza-bicyclo[3.1.0]hex-3-yl}pyrimidine-5-carboxamide, and N-Hydroxy 2-{6-[(quinolin-2-ylmethyl)-amino]-3-aza-bicyclo[3.1.0]hex-3-yl}pyrimidine-5-carboxamide, and their N-oxides or salts.

* * * * *

UNITED STATES PATENT AND TRADEMARK OFFICE
CERTIFICATE OF CORRECTION

| | | |
|---|---|---|
| PATENT NO. | : 7,932,246 B2 | Page 1 of 1 |
| APPLICATION NO. | : 11/918237 | |
| DATED | : April 26, 2011 | |
| INVENTOR(S) | : David Festus Charles Moffat et al. | |

It is certified that error appears in the above-identified patent and that said Letters Patent is hereby corrected as shown below:

Column 100, Claim 4, Line 3:
Please delete ", hydrates and solvates"

Signed and Sealed this
Tenth Day of January, 2012

David J. Kappos
*Director of the United States Patent and Trademark Office*